US009809537B2

(12) United States Patent
McEachern et al.

(10) Patent No.: US 9,809,537 B2
(45) Date of Patent: Nov. 7, 2017

(54) GLYCOSIDASE INHIBITORS AND USES THEREOF

(71) Applicants: Alectos Therapeutics Inc., Burnaby (CA); Merck Sharp & Dohme Corp., Rahway, NJ (US)

(72) Inventors: Ernest J. McEachern, Vancouver (CA); Jianyu Sun, Burnaby (CA); David J. Vocadlo, Burnaby (CA); Yuanxi Zhou, Burnaby (CA); Yongbao Zhu, Burnaby (CA); Harold G. Selnick, West Point, PA (US)

(73) Assignees: Alectos Therapeutics Inc., Burnaby (CA); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/424,873

(22) PCT Filed: Aug. 29, 2013

(86) PCT No.: PCT/CA2013/050672
§ 371 (c)(1),
(2) Date: Feb. 27, 2015

(87) PCT Pub. No.: WO2014/032188
PCT Pub. Date: Mar. 6, 2014

(65) Prior Publication Data
US 2015/0274656 A1    Oct. 1, 2015

Related U.S. Application Data

(60) Provisional application No. 61/695,987, filed on Aug. 31, 2012.

(51) Int. Cl.
| | | |
|---|---|---|
| C07D 207/12 | (2006.01) | |
| A61K 31/40 | (2006.01) | |
| A61K 31/428 | (2006.01) | |
| A61K 31/4439 | (2006.01) | |
| C07D 401/06 | (2006.01) | |
| C07D 417/06 | (2006.01) | |
| C12N 9/99 | (2006.01) | |
| C07D 207/16 | (2006.01) | |

(52) U.S. Cl.
CPC ............ *C07D 207/12* (2013.01); *A61K 31/40* (2013.01); *A61K 31/428* (2013.01); *A61K 31/4439* (2013.01); *C07D 207/16* (2013.01); *C07D 401/06* (2013.01); *C07D 417/06* (2013.01); *C12N 9/99* (2013.01); *C12Y 302/01169* (2013.01)

(58) Field of Classification Search
CPC .......................... C07D 2017/12; C07D 207/12
USPC .......................................... 548/556; 514/424
See application file for complete search history.

(56) References Cited

U.S. PATENT DOCUMENTS

| | | |
|---|---|---|
| 4,871,747 A | 10/1989 | Kinast et al. |
| 5,079,254 A | 1/1992 | Liu et al. |
| 5,276,120 A | 1/1994 | Wong et al. |
| 5,451,679 A | 9/1995 | Barta et al. |
| 6,291,657 B1 | 9/2001 | Platt et al. |
| 6,451,836 B1 | 9/2002 | Lundgren et al. |
| 6,774,140 B1 | 8/2004 | Wong et al. |
| 7,105,320 B2 | 9/2006 | Kobayashi et al. |
| 7,135,578 B2 * | 11/2006 | Wong ..................... A61K 31/40 |
| | | 548/556 |
| 8,334,310 B2 | 12/2012 | Vocadlo et al. |
| 8,541,441 B2 | 9/2013 | Vocadlo et al. |
| 8,927,507 B2 | 1/2015 | McEachern et al. |
| 8,933,040 B2 | 1/2015 | Coburn et al. |
| 8,962,664 B2 | 2/2015 | Vocadlo et al. |
| 9,243,020 B2 | 1/2016 | Kaul et al. |
| 2001/0027195 A1 | 10/2001 | Nugiel et al. |
| 2004/0083559 A1 | 5/2004 | Sabelle et al. |
| 2004/0132142 A1 | 7/2004 | Kobayashi et al. |
| 2004/0147591 A1 | 7/2004 | Kanie et al. |
| 2004/0198722 A1 | 10/2004 | Thurston et al. |
| 2007/0167440 A1 | 7/2007 | Moritani et al. |
| 2007/0197471 A1 | 8/2007 | Ichikawa |
| 2008/0085920 A1 | 4/2008 | Donello et al. |
| 2008/0096932 A1 | 4/2008 | Mansfield et al. |
| 2008/0166323 A1 | 7/2008 | Marchase et al. |
| 2008/0287375 A1 | 11/2008 | Vocadlo et al. |
| 2009/0068120 A1 | 3/2009 | Suga et al. |
| 2010/0016386 A1 | 1/2010 | Vocadlo et al. |

(Continued)

FOREIGN PATENT DOCUMENTS

| | | |
|---|---|---|
| AT | 507745 A1 | 7/2010 |
| AU | 507745 B2 | 2/1980 |

(Continued)

OTHER PUBLICATIONS

Liu et al., "Synthesis and, etc.," J. Org. Chem. 2004, 69, 6273-6283.*
Shih et al., "Combinatorial approach, etc.," Org. Biomol. Chem., 2010, 8, 2586-2593.*
Liang et al., "Novel Five, etc.," ChemBioChem 2006, 7, 165-173.*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burgers Medicinal Chemistry and Drug Discovery. 5th ed. vol. 1: Principles and Practice. pp. 949-982, 1996.*

(Continued)

*Primary Examiner* — Patricia L Morris
(74) *Attorney, Agent, or Firm* — Clark & Elbing LLP

(57) ABSTRACT

The invention provides compounds for inhibiting glycosidases, prodrugs of the compounds, and pharmaceutical compositions including the compounds or prodrugs of the compounds. The invention also provides methods of treating diseases and disorders related to deficiency or overexpression of O-GlcNAcase, accumulation or deficiency of O-GlcNAc.

6 Claims, No Drawings

(56) References Cited

U.S. PATENT DOCUMENTS

| | | | |
|---|---|---|---|
| 2011/0195929 A1* | 8/2011 | De Moor | A61K 31/40 514/63 |
| 2011/0237538 A1 | 9/2011 | De Moor et al. | |
| 2011/0237631 A1 | 9/2011 | Vocadlo et al. | |
| 2011/0301217 A1 | 12/2011 | Vocadlo et al. | |
| 2012/0095033 A1 | 4/2012 | Vocadlo et al. | |
| 2012/0316207 A1 | 12/2012 | Vocadlo et al. | |
| 2013/0131044 A1 | 5/2013 | Li et al. | |
| 2013/0296301 A1 | 11/2013 | Chang et al. | |
| 2014/0005191 A1 | 1/2014 | Coburn et al. | |
| 2014/0018309 A1 | 1/2014 | Kaul et al. | |
| 2014/0051719 A1 | 2/2014 | Vocadlo et al. | |
| 2014/0088028 A1 | 3/2014 | Kaul et al. | |
| 2014/0107044 A1 | 4/2014 | McEachern et al. | |
| 2014/0206665 A1 | 7/2014 | Selnick et al. | |
| 2014/0243370 A1 | 8/2014 | Donnelly et al. | |
| 2014/0275022 A1 | 9/2014 | Li et al. | |
| 2014/0296205 A1 | 10/2014 | Li et al. | |
| 2015/0045346 A1 | 2/2015 | Li et al. | |
| 2015/0218147 A1 | 8/2015 | McEachern et al. | |
| 2016/0096858 A1 | 4/2016 | Kaul et al. | |

FOREIGN PATENT DOCUMENTS

| | | |
|---|---|---|
| CA | 2045539 A1 | 7/1990 |
| CA | 2163503 A1 | 5/1996 |
| CA | 2235415 A1 | 3/1997 |
| CA | 2599843 A1 | 9/2006 |
| CA | 2661582 A1 | 3/2008 |
| CA | 2737267 A1 | 4/2010 |
| CA | 2816798 A1 | 5/2012 |
| CA | 2822493 A1 | 6/2012 |
| CA | 2890115 A1 | 5/2014 |
| CN | 101595111 A | 12/2009 |
| EP | 0243686 A2 | 11/1987 |
| EP | 0304731 A1 | 3/1989 |
| EP | 1371733 A1 | 12/2003 |
| JP | 01-180894 A | 7/1989 |
| JP | 07-316178 A | 12/1995 |
| JP | 09-132585 A | 5/1997 |
| JP | 11-349541 A | 12/1999 |
| JP | 2002-338532 A | 11/2002 |
| JP | 2003-012683 A | 1/2003 |
| JP | 42-3500 | 10/2008 |
| SU | 1 441 749 A1 | 1/1996 |
| WO | WO-91/18598 A1 | 12/1991 |
| WO | WO-92/03415 A1 | 3/1992 |
| WO | WO-97/09040 A1 | 3/1997 |
| WO | WO-00/68194 A1 | 11/2000 |
| WO | WO-02/072860 A1 | 9/2002 |
| WO | WO-03/009808 A2 | 2/2003 |
| WO | WO-2004/103368 A1 | 12/2004 |
| WO | WO-2004/103386 A1 | 12/2004 |
| WO | WO-2005/026156 A1 | 3/2005 |
| WO | WO-2005/072268 A2 | 8/2005 |
| WO | WO-2005/115977 A1 | 12/2005 |
| WO | WO-2006/016904 A2 | 2/2006 |
| WO | WO-2006/031852 A1 | 3/2006 |
| WO | WO-2006/037069 A1 | 4/2006 |
| WO | WO-2006/092049 A1 | 9/2006 |
| WO | WO-2006/100586 A1 | 9/2006 |
| WO | WO-2006/114401 A2 | 11/2006 |
| WO | WO-2007/048802 A1 | 5/2007 |
| WO | WO-2007/067515 A2 | 6/2007 |
| WO | WO-2008/025170 A1 | 3/2008 |
| WO | WO-2010/012106 A1 | 2/2010 |
| WO | WO-2010/012107 A1 | 2/2010 |
| WO | WO-2010/015815 A2 | 2/2010 |
| WO | WO-2010/015816 A2 | 2/2010 |
| WO | WO-2010/029313 A1 | 3/2010 |
| WO | WO-2010/037207 A1 | 4/2010 |
| WO | WO-2010/049678 A2 | 5/2010 |
| WO | WO-2011/060397 A1 | 5/2011 |
| WO | WO-2011/140640 A1 | 11/2011 |
| WO | WO-2012/061927 A1 | 5/2012 |
| WO | WO-2012/061971 A1 | 5/2012 |
| WO | WO-2012/061972 A1 | 5/2012 |
| WO | WO-2012/062157 A1 | 5/2012 |
| WO | WO-2012/064680 A1 | 5/2012 |
| WO | WO-2012/083435 A1 | 6/2012 |
| WO | WO-2012/117219 A1 | 9/2012 |
| WO | WO-2012/126091 A1 | 9/2012 |
| WO | WO-2012/127506 A1 | 9/2012 |
| WO | WO-2012/129651 A1 | 10/2012 |
| WO | WO-2012/129802 A1 | 10/2012 |
| WO | WO-2013/000084 A1 | 1/2013 |
| WO | WO-2013/000085 A1 | 1/2013 |
| WO | WO-2013/000086 A1 | 1/2013 |
| WO | WO-2013/025452 A1 | 2/2013 |
| WO | WO-2013/028715 A1 | 2/2013 |
| WO | WO-2013/169576 A1 | 11/2013 |
| WO | WO-2014/032184 A1 | 3/2014 |
| WO | WO-2014/032185 A1 | 3/2014 |
| WO | WO-2014/032187 A1 | 3/2014 |
| WO | WO-2014/032188 A1 | 3/2014 |
| WO | WO-2014/067003 A1 | 5/2014 |
| WO | WO-2014/105662 A1 | 7/2014 |

OTHER PUBLICATIONS

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Layzer, Degenerative Diseases of the Nervous System, Cecil Textbook of Medicine, 20th Edition, vol. 2, pp. 2050-2057 (1996).*

Damasio, Alzheimer's Disease and Related Dementias, Cecil Textbook of Medicine, 20th Edition, vol. 2, pp. 1992-1996 (1996).*

Ouaissi et al., "Rationale for Possible, etc.," Journal of Biomedicine and Biotechnology, 2011, Article: ID 315939, 1-8.*

Golub et al, Science, vol. 286, Oct. 15, 1999, pp. 531-537.*

Robinson' "Medical Therapy, etc.," Eur. J. Sirg. 1998: Suppl 582:90-98.*

Tauopathy—Wikpedia encyclopedia printed on Dec. 15, 2016, pp. 1-4.*

International Search Report and Written Opinion for International Patent Application No. PCT/CA2013/050672, mailed Oct. 21, 2013 (12 pages).

Marotta et al., "O-GlcNAc modification prevents peptide-dependent acceleration of alpha-synuclein aggregation," Chembiochem. 13(18):2665-70 (2012).

Alfaro et al., "Tandem mass spectrometry identifies many mouse brain O-GlcNAcylated proteins including EGF domain-specific O-GlcNAc transferase targets," Proc Natl Acad Sci U S A. 109(19):7280-5 (2012).

Wang et al., "Enrichment and site mapping of O-linked N-acetylglucosamine by a combination of chemical/enzymatic tagging, photochemical cleavage, and electron transfer dissociation mass spectrometry," Mol Cell Proteomics. 9(1):153-60 (2010).

Alafuzoff et al., "Histopathological criteria for progressive dementia disorders: clinical-pathological correlation and classification by multivariate data analysis," Acta Neuropathol. 74(3):209-25 (1987).

Alonso et al., "Promotion of Hyperphosphorylation by Frontotemporal Dementia Tau Mutations," J Biol Chem 279(33):34873-34881 (2004).

Arias et al., "Prolonged incubation in PUGNAc results in increased protein O-Linked glycosylation and insulin resistance in rat skeletal muscle," Diabetes. 53(4):921-30 (2004).

Arnold et al., "The microtubule-associated protein tau is extensively modified with O-linked N-acetylglucosamine," 271(46):28741-28744 (1996).

Arriagada et al., "Neurofibrillary tangles but not senile plaques parallel duration and severity of Alzheimer's disease," Neurology. 42(3 Pt 1):631-9 (1992).

(56) References Cited

OTHER PUBLICATIONS

Avalos et al., "Condensation of 2-amino-2-deoxysugars with isothiocyanates. Synthesis of cis-1,2-fused glycopyrano heterocycles," Tetrahedron 50(10):3273-3296 (1994).
Avalos Gonzalez et al., "Sintesis de hidrobromuros de glucopirano[2,1-d]-2-tiazo-linas," Anales de Quimica 84(1):5-11 (1988) (English abstract included).
Balant ed in Wolff et al., "Burger's Medicinal Chemistry and Drug Discovery", 5th Edition, vol. 1: Principles and Practice. pp. 949-982, 1996.
Bastin et al., "Salt selection and optimisation procedures for pharmaceutical new chemical entities," Org. Process Res. Dev. 4(5):427-35 (2000).
Baxter et al., "Expeditious Synthesis of Azasugars by the Double Reductive Amination of Dicarbonyl Sugars," J. Org. Chem. 59(11):3175-85 (1994).
Bedi et al., "A convenient synthesis of p-nitrophenyl 2-deoxy-2-(thio-acetamido)-beta-d-glucopyranoside, -galactopyranoside, and their 1-thio analogs as inhibitors of 2-acetamido-2-deoxy-beta-d-glucosidase," Carbohydr. Res. 62(2):253-9 (1978).
Bennett et al., "Alkylation of DNA in rat tissues following administration of streptozotocin," Cancer Res. 41(7):2786-90 (1981).
Bergmann et al., "Synthesen mit Glucosamin," Ber. Dtsch Chem. Ges., 64B:975-980 (1999).
Bertram et al., "Evidence for genetic linkage of Alzheimer's disease to chromosome 10q," Science. 290(5500):2302-3 (2000).
Blattner et al., "Syntheses of the Fungicidal and Insecticidal Allosamidin and a Structural Isomer", Journal of the Chemical Society, Perkin Trans 1., vo. 23, 1994, pp. 3411-3421.
Boullanger et al., "The use of N-alkoxycarbonyl derivatives of 2-amino-2-deoxy-D-glucose as donors in glycosylation reactions," Carbohydr Res. 202:151-64 (1990).
Bounelis et al., "Glucosamine provides protection from ischemia/reperfusion injury and calcium overload in isolated hearts and leads to an increase in O-linked glycosylation," Shock. 21(Suppl 2):58, Abstract 170 (2004).
Bovin et al., "Synthesis and study of D-glucose thiazoline derivatives," Izvestiya Akademii Nauk SSSR, Seriya Khimicheskaya, (2): 441-3 (1981) (4 pages).
Boyd et al., "Pharmacological chaperones as therapeutics for lysosomal storage diseases," J Med Chem 56(7):2705-2725 (2013).
Braidman et al., "Separation and properties of human brain hexosaminidase C," Biochem J. 143(2):295-301 (1974).
Bras et al., Glycosidase inhibitors: a patent review (2008-2013), Expert Opinion on Therapeutic Patents, vol. 24, No. 8, pp. 857-874, Aug. 1, 2014.
Brickley et al., "GRIF-1 and OIP106, members of a novel gene family of coiled-coil domain proteins: association in vivo and in vitro with kinesin," J Biol Chem. 280(15):14723-32 (2005).
Burger et al., "N-pyridingyl . . . " CA151: 358734 (2009).
Burkart et al., "Mice lacking the poly(ADP-ribose) polymerase gene are resistant to pancreatic beta-cell destruction and diabetes development induced by streptozocin," Nat Med. 5(3):314-9 (1999).
Cantarel et al., "The Carbohydrate-Active EnZymes database (CAZy): an expert resource for Glycogenomics," 37:D233-D238 (2009).
Champattanachai et al., "Glucosamine protects neonatal cardiomyocytes from ischemia-reperfusion injury via increased protein O-GlcNAc and increased mitochondrial Bcl-2," Am J Physiol Cell Physiol. 294(6):C1509-20 (2008).
Champattanachai et al., "Glucosamine protects neonatal cardiomyocytes from ischemia-reperfusion injury via increased protein-associated O-GlcNAc," Am J Physiol Cell Physiol. 292(1):C178-87 (2007).
Cheng et al., "Alternative O-glycosylation/O-phosphorylation of serine-16 in murine estrogen receptor beta: post-translational regulation of turnover and transactivation activity," J Biol Chem. 276(13):10570-5 (2001).
Cheng et al., "Alternative O-glycosylation/O-phosphorylation of the murine estrogen receptor beta," Biochemistry. 39(38):11609-20 (2000).
Chou et al., "c-Myc is glycosylated at threonine 58, a known phosphorylation site and a mutational hot spot in lymphomas," J Biol Chem. 270(32):18961-5 (1995).
Chou et al., "O-linked N-acetylglucosamine and cancer: messages from the glycosylation of c-Myc," Adv Exp Med Biol. 491:413-8 (2001).
Choubdar et al., "Synthesis of 2-amido, 2-amino, and 2-azido derivatives of the nitrogen analogue of the naturally occurring glycosidase inhibitor salacinol and their inhibitory activities against O-GlcNAcase and agZ enzymes", Carbohydrate Research, Pergamon, vol. 343, No. 10-11, pp. 1766-1777, Jul. 21, 2008.
Cole et al., "Glycosylation sites flank phosphorylation sites on synapsin I: O-linked N-acetylglucosamine residues are localized within domains mediating synapsin I interactions," J Neurochem. 73(1):418-28 (1999).
Corbett et al., "The synthesis of pseudo-sugars related to allosamizoline," Tetrahedron Lett 34(9):1525-28 (1993).
Cresswell et al., "Diastereodivergent hydroxyfluorination of cyclic and acyclic allylic amines: synthesis of 4-deoxy-4-fluorophytosphingosines," J Org Chem 77(17):7262-81 (2012).
Cunha et al., "Use of protecting groups in carbohydrate chemistry. An advanced organic synthesis experiment," J Chem Ed 76(1):79-80 (1999).
De La Fuente A. et al., Stereoselective synthesis of 2-acetamido-1,2-dideoxynojirimycin (DNJNAc) and ureido-DNHNAc derivatives as new hexosaminidase inhibitors. Org Biomol Chem 2015;13(23):6500-10.
de la Monte et al., "Review of insulin and insulin-like growth factor expression, signaling, and malfunction in the central nervous system: relevance to Alzheimer's disease," J Alzheimers Dis. 7(1):45-61 (2005).
de la Torre, "Alzheimer's disease is a vasocognopathy: a new term to describe its nature," Neurol Res. 26(5):517-24 (2004).
Deng et al., "Regulation between O-GlcNAcylation and phosphorylation of neurofilament-M and their dysregulation in Alzheimer disease," FASEB J. 22(1):138-45 (2008).
Dennis et al., "Structure and mechanism of a bacterial b-glucosaminidase having O-GlcNAcase activity," Nat Struct Mol Bio 13(4):365-371 (2006).
Desnick et al., "Schindler disease: an inherited neuroaxonal dystrophy due to alpha-N-acetylgalactosaminidase deficiency," J Inherit Metab Dis. 13(4):549-59 (1990).
Dong et al., "Purification and characterization of an O-GlcNAc selective N-acetyl-beta-D-glucosaminidase from rat spleen cytosol," J Biol Chem. 269(30):19321-30 (1994).
Donohoe et al., "A Concise and Efficient Synthesis of (-)-Allosamizoline", Org. Lett., 2007, vol. 9, No. 26, pp. 5509-5511.
Dorfmueller et al., "GlcNAcstatin: a picomolar, selective 0-GlcNAcase inhibitor that modulates intracellular O-GlcNAcylation Levels," J Am Chem Soc 128(51):16484-16485 (2006).
Dorfmueller et al., "Screening-based discovery of drug-like O-GlcNAcase inhibitor scaffolds," FEBS Lett 584(4):694-700 (2010).
Drouillard et al., "Serratia marcescens chitobiase is a retaining glycosidase utilizing substrate acetamido group participation," Biochem J 328(3):945-949 (1997).
Extended European Search Report issued in corresponding European Patent Application No. 13834204.3 dated Dec. 15, 2015.
Fadel et al., "An efficient synthesis of enantiomerically pure (R)-pipecolic acid, (S)-proline, and their N-alkylated derivatives," J Org Chem 72(5):1780-4 (2007).
Falentin C., et al., New approach to (-)-polyoxamic acid and 3,4-diepipolyoxamic acid from D-lyxono-1,4-lactone. Tetrahedron 2008;64(42):9989-9991.
Fan et al., "Ester prodrugs of ampicillin tailored for intracellular accumulation," Bioorg Med Chem Lett. 7(24):3107-12 (1997).
Feng et al., "Synthesis of enantio-enriched chiral building blocks from L-glutamic acid", Tetrahedron, vol. 62, No. 31, pp. 7459-7465, Jul. 31, 2006.

(56) References Cited

OTHER PUBLICATIONS

Friedhoff et al., "Rapid assembly of Alzheimer-like paired helical filaments from microtubule-associated protein tau monitored by fluorescence in solution," Biochemistry. 37(28):10223-30 (1998).
Frölich et al., "Brain insulin and insulin receptors in aging and sporadic Alzheimer's disease," J Neural Transm. 105(4-5):423-38 (1998).
Fulop et al., "Diabetes, the hexosamine biosynthesis pathway and protein O-glycsoylation in the heart," J Mol Cell Cardiol. 37:286-7 Abstract C86 (2004).
Fulop et al., "Effects of glucosamine on the isolated rat heart," FASEB J. 19:A689-90 Abstract 386.6 (2005).
Fulop et al., "Glucosamine-induced cardioprotection mediated by the hexosamine biosynthesis pathway and increased levels of O-linked N-acetylglucosamine on nucleocytoplasmic proteins," available in PMC Apr. 3, 2010, published in final edited form as: Circ Res. 97:e28 Abstract 104 (2005).
Fulop et al., "Role of protein O-linked N-acetyl-glucosamine in mediating cell function and survival in the cardiovascular system," Cardiovasc Res. 73(2): 288-297 (2007) (17 pages).
Furneaux et al., "2-acetamido-1, 2-dideoxynojirimycin: an improved synthesis," Tetraheron 49(42):9605-9612 (1993).
Furneaux et al., The Chemistry of Castanospermine, Part I: Synthetic Modifications as C-6; Tetrahedron (1994), 50(7), 2131-60.
Gao et al., "Dynamic O-glycosylation of nuclear and cytosolic proteins: cloning and characterization of a neutral, cytosolic beta-N-acetylglucosaminidase from human brain," J Biol Chem. 276(13):9838-45 (2001).
Gao et al., "Streptozotocin-induced beta-cell death is independent of its inhibition of O-GlcNAcase in pancreatic Min6 cells," Arch Biochem Biophys. 383(2):296-302 (2000).
Garneau et al., "Synthesis of mono- and disaccharide analogs of moenomycin and lipid II for inhibition of transglycosylase activity of penicillin-binding protein 1b," Bioorg Med Chem 12(24):6473-6494 (2004).
Glawar et al., "Scalable syntheses of both enantiomers of DNJNAc and DGJNAc from glucuronolactone: the effect of N-alkylation on hexosaminidase inhibition," Chem Eur J. 18:9341-59 (2012).
Gloster et al., "Mechanism, Structure, and Inhibition of O-GlcNAc Processing Enzymes," available in PMC Apr. 14, 2010, published in final edited form as: Curr Signal Transduct Ther. 5(1):74-91 (2010) (33 pages).
Gmelin, "Piperidine," Handbook of Chemistry 10:446-9 (1856).
Godskesen et al "Synthesis and Evaluation of 5-membered Isoimiosugar as Glycosidase Inhibitor", Tetrahedron Letters 39, 1998 5841-5844.
Goedert et al., "Multiple isoforms of human microtubule-associated protein tau: sequences and localization in neurofibrillary tangles of Alzheimer's disease," Neuron. 3(4):519-26 (1989).
Goedert et al., "Tau proteins of Alzheimer paired helical filaments: abnormal phosphorylation of all six brain isoforms," Neuron. 8(1):159-68 (1992).
Goeminne et al., "N-Arylmethyl substituted iminoribitol derivatives as inhibitors of a purine specific nucleoside hydrolase," Bioorg Med Chem. 16(14):6752-63 (2008).
Goering et al,. "Total synthesis of (±)-allosamizoline from a symmetric trisubstituted cyclopentene," Tetrahedron Lett. 35(38):6997-7000 (1994).
Gong et al., "Impaired brain glucose metabolism leads to Alzheimer neurofibrillary degeneration through a decrease in tau O-GlcNAcylation," J Alzheimers Dis. 9(1):1-12 (2006).
Gong et al., "Post-translational modifications of tau protein in Alzheimer's disease," J Neural Transm. 112(6):813-38 (2005).
Gonzalez et al., "Synthesis of 1, 3, 4, 6-tetra-O-acetyl-2-[3-alkyl(aryl)-thioureido]-2-deoxy-a-D-glucopyranoses and their transformation into 2-alkyl(aryl)amino-1,2-dideoxy-a-D-glucopyrano)[2, 1-d]-2-thiazolines," Carbohydrate Research 154:49-62 (1986).
Greene, "Protection for the Amino Group." Protective Groups in Organic Synthesis. John Wiley & Sons, 218-220, 224, 251 (1982).

Griffith et al., "O-linked N-acetylglucosamine is upregulated in Alzheimer brains," Biochem Biophys Res Commun. 213(2):424-31 (1995).
Griffith et al., "O-linked N-acetylglucosamine levels in cerebellar neurons respond reciprocally to pertubations of phosphorylation," Eur J Biochem. 262(3):824-31 (1999).
Griffith et al., "The total synthesis of Allosamidin. Expansions of the methodology of azaglycosylation pursuant to the total synthesis of Allosamidin. A surprising enantiotopic sense for a Lipase-induced deacetylation", J. Am. Chem. Soc, 1996, vol. 118, pp. 9526-9538.
Griffith et al., J. Am. Chem. Soc. 1991, 113, 5863-5864.
Grolla et al., "Synthesis, biological evaluation, and molecular docking of Ugi products containing a zinc-chelating moiety as novel inhibitors of histone deacetylases," J Med Chem. 52(9):2776-85 (2009).
Haltiwanger et al., "Enzymatic addition of O-GlcNAc to nuclear and cytoplasmic proteins. Identification of a uridine diphospho-N-acetylglucosamine:peptide beta-N-acetylglucosaminyltransferase," J Biol Chem. 265(5):2563-8 (1990).
Haltiwanger et al., "Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene)amino-N-phenylcarbamate," J Biol Chem. 273(6):3611-7 (1998).
Hanover et al., "Elevated O-linked N-acetylglucosamine metabolism in pancreatic beta-cells," Arch Biochem Biophys. 362(1):38-45 (1999).
Hanover, "Glycan-dependent signaling: O-linked N-acetylglucosamine," FASEB J. 15(11):1865-76 (2001).
Heightman et al., "Recent Insights into Inhibition, Structure, and Mechanism of Configuration-Retaining Retaining Glycosidases," *Angew Chem Int Ed.* 38:750-70 (1999).
Henrissat et al., "New families in the classification of glycosyl hydrolases based on amino acid sequence similarities," Biochem J. 293(Pt 3):781-8 (1993).
Henrissat et al., "Updating the sequence-based classification of glycosyl hydrolases," Biochem J. 316(Pt 2):695-6 (1996).
Horig et al., "From bench to clinic and back: Perspective on the 1st IQPC Translational Research conference," J Trans Med 2(44) (2004).
Horsch et al., "N-acetylglucosaminono-1,5-lactone oxime and the corresponding (phenylcarbamoyl)oxime. Novel and potent inhibitors of beta-N-acetylglucosaminidase," Eur J Biochem. 197(3):815-8 (1991).
Hoyer, "Brain glucose and energy metabolism abnormalities in sporadic Alzheimer disease. Causes and consequences: an update," Exp Gerontol. 35(9-10)1 363-72 (2000).
Hoyer, "Causes and consequences of disturbances of cerebral glucose metabolism in sporadic Alzheimer disease: therapeutic implications," Adv Exp Med Biol. 541:135-52 (2004).
Huang et al., "The hexosamine biosynthesis pathway negatively regulates IL-2 production by Jurkat T cells," available in PMC Sep. 22, 2011, published in final edited form as: Cell Immunol. 245(1):1-6 (2007) (10 pages).
Inglese et al., "High-throughput screening assays for the identification of chemical probes", Nature Chemical Biology, 2007, 3, 466-479.
International Preliminary Report on Patentabiilty issued in corresponding International Application No. PCT/CA2013/050672 dated Mar. 15, 2015.
International Search Report and Written Opinion issued in corresponding International Application No. PCT/CA2013/050672 dated Oct. 21, 2013.
Iqbal et al., "Alzheimer neurofibrillary degeneration: therapeutic targets and high-throughput assays," J Mol Neurosci. 20(3):425-9 (2003).
Iqbal et al., "Pharmacological targets to inhibit Alzheimer neurofibrillary degeneration," J Neural Transm Suppl. (62):309-19 (2002).
Iqbal et al., "Tau pathology in Alzheimer disease and other tauopathies," Biochim Biophys Acta. 1739(2-3):198-210 (2005).

(56) References Cited

OTHER PUBLICATIONS

Isac-Garcia et al., Reactivity of 2-deoxy-2-iodoglycosyl isothiocyanates with O-, S-, and N-nucleophils. Synthesis of Glycopyranoso-Fused Thiazoles, J Org Chem 69(1):202-205 (2004).

Ito et al., "A medium-term rat liver bioassay for rapid in vivo detection of carcinogenic potential of chemicals," Cancer Sci 94(1):3-8 (2003).

Iyer et al., "Identification and cloning of a novel family of coiled-coil domain proteins that interact with O-GlcNAc transferase," J Biol Chem. 278(7):5399-409 (2003).

Iyer et al., "Roles of the tetratricopeptide repeat domain in O-GlcNAc transferase targeting and protein substrate specificity," J Biol Chem. 278(27):24608-16 (2003).

Jackson et al., "O-glycosylation of eukaryotic transcription factors: implications for mechanisms of transcriptional regulation," Cell. 55(1):125-33 (1988).

Jagust et al., "Diminished glucose transport in Alzheimer's disease: dynamic PET studies," J Cereb Blood Flow Metab. 11(2):323-30 (1991).

Jeyakumar et al., "Storage solutions: treating lysosomal disorders of the brain," Nat Rev Neurosci. 6(9):713-25 (2005) (12 pages).

Jinek et al., "The superhelical TPR-repeat domain of O-linked GlcNAc transferase exhibits structural similarities to importin alpha," Nat Struct Mol Biol. 11(10): 1001-7 (2004).

Jochims et al., "Isocyanato- und isothiocyanato-derivate des d-glucosamins," Tetrahedron. 21:2611-6 (1965).

Johnstone, "Existence of a volatile alkaloid in pepper," Chemical News and Journal of Industrial Science. 58(1512):235 (1888).

Jones et al., "Purification, properties, kinetics, and mechanism of beta-N-acetylglucosamidase from Aspergillus niger," J Biol Chem. 255(24):11861-9 (1980).

Junod et al., "Studies of the diabetogenic action of streptozotocin," Proc Soc Exp Biol Med. 126(1):201-5 (1967).

Kajimoto et al., "Enzyme-catalyzed aldol condensation for asymmetric synthesis of azasugars: synthesis, evaluation, and modeling of glycosidase inhibitors," J Am Chem Soc. 113(16):6187-96 (1991).

Kalaria et al., "Reduced glucose transporter at the blood-brain barrier and in cerebral cortex in Alzheimer disease," J Neurochem. 53(4):1083-8 (1989).

Kalow et al., "Mechanistic investigations of cooperative catalysis in the enantioselective fluorination of epoxides," J Am Chem Soc. 133(40):16001-12 (2011).

Kamemura et al., "Dynamic interplay between O-glycosylation and O-phosphorylation of nucleocytoplasmic proteins: a new paradigm for metabolic control of signal transduction and transcription," Prog Nucleic Acid Res Mol Biol. 73:107-36 (2003).

Kamemura et al., "Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens," J Biol Chem. 277(21):19229-35 (2002).

Katsuhiko et al., "3,4-Dihydroxypyrrolidine as Glycosidase Inhibitor 11", Current Topics in Medicinal Chemistry, vol. 9, No. 1, 34-57 (2009).

Kelly et al., "RNA polymerase II is a glycoprotein. Modification of the COOH-terminal domain by O-GlcNAc," J Biol Chem. 268(14):10416-24 (1993).

Khlistunova et al., "Inhibition of tau aggregation in cell models of tauopathy," Curr Alzheimer Res. 4(5):544-6 (2007).

Kinoshita et al., "Preparation of N-Monoalkyl and O-Acyl Derivatives of Allosamidin, and Their Chitinase Inhibitory Activities," Biosci Biotechnol Biochem. 57(10):1699-703 (1993).

Kitahara et al., "Synthesis of (-)-Allosamizoline, the Pseudoaminosugar Moiety of Allosamidin, a Chitinase Inhibitor," Biosci Biotechnol Biochem. 57(11):1906-9 (1993).

Knapp et al., "Addition of trialkylaluminum reagents to glyconolactones. Synthesis of 1-C-methyl GlcNAc oxazoline and thiazoline," Tetrahedron Letters 43:7101-4 (2002).

Knapp et al., "Alpha-GlcNAc thioconjugates," J Org Chem. 66(10):3636-8 (2001).

Knapp et al., "An allosamizoline/glucosamine hybrid NAGase inhibitor," Synlett. 435-6 (1997).

Knapp et al., "NAG-thiazoline, an N-acetyl-beta-hexosaminidase inhibitor that implicates acetamido participation," J Am Chem Soc. 118:6804-5 (1996).

Knapp et al., "New glycomimetics: anomeric sulfonates, sulfenamides, and sulfonamides," J Org Chem. 71(4):1380-9 (2006).

Knapp et al., "Shortcut to mycothiol analogues," Org Lett. 4(24):4337-9 (2002).

Knapp et al., "Synthesis of alpha-GalNAc thioconjugates from an alpha-GalNAc mercaptan," J Org Chem. 67(9):2995-9 (2002).

Knapp et al., "Tautomeric modification of GlcNAc-thiazoline," Org Lett. 9(12):2321-4 (2007).

Knapp et al., "The Surprise Synthesis of alpha-GlcNAc 1-C-Sulfonates," Tetrahedron Lett. 43: 6075-8 (2002).

Kobayashi et al., "Enzymatic synthesis of chondroitin and its derivatives catalyzed by hyaluronidase," J Am Chem Soc. 125(47):14357-69 (2003).

Konrad et al., "The potential mechanism of the diabetogenic action of streptozotocin: inhibition of pancreatic beta-cell O-GlcNAc-selective N-acetyl-beta-D-glucosaminidase," Biochem J. 356(Pt 1):31-41 (2001).

Kopke E., et al., Microtubule-associated protein tau. Abnormal phosphorylation of a non-paired helical filament pool in Alzheimer disease. J Biol Chem 1993;268(32):24374-84.

Kreppel et al., "Dynamic glycosylation of nuclear and cytosolic proteins. Cloning and characterization of a unique O-GlcNAc transferase with multiple tetratricopeptide repeats," J Biol Chem. 272(14):9308-15 (1997).

Kreppel et al., "Regulation of a cytosolic and nuclear O-GlcNAc transferase. Role of the tetratricopeptide repeats," J Biol Chem. 274(45):32015-22 (1999).

Kröncke et al., "Nitric oxide generation during cellular metabolization of the diabetogenic N-methyl-N-nitroso-urea streptozotozin contributes to islet cell DNA damage," Biol Chem Hoppe Seyler. 376(3):179-85 (1995).

Ksiezak-Reding et al., "Phosphate analysis and dephosphorylation of modified tau associated with paired helical filaments," Brain Res. 597(2):209-19 (1992).

Kuroki et al., "Structural basis of the conversion of T4 lysozyme into a transglycosidase by reengineering the active site," Proc Natl Acad Sci USA. 96(16):8949-54 (1999).

Lamarre-Vincent et al., "Dynamic glycosylation of the transcription factor CREB: a potential role in gene regulation," J Am Chem Soc. 125(22):6612-3 (2003).

Lameira et al., "Enzyme molecular mechanism as a starting point to design new inhibitors: a theoretical study of O-GlcNAcase," J Phys Chem B. 115(20):6764-75 (2011).

Lau et al., "Tau protein phosphorylation as a therapeutic target in Alzheimer's disease," Curr Top Med Chem. 2(4):395-415 (2002).

Le Corre et al., "An inhibitor of tau hyperphosphorylation prevents severe motor impairments in tau transgenic mice," Proc Natl Acad Sci U.S.A. 103(25):9673-8 (2006).

Le Huerou et al., "Preparation of pyrrolopyridines as checkpoint kinase CHK1 and/or CHK2 inhibitors," CA151:550551 (2009) (2 pages).

Lee et al., "Probing the Abilities of Synthetically Useful Serine Proteases to Discriminate between the Configurations of Remote Stereocenters Using Chiral Aldehyde Inhibitors," J Am Chem Soc. 118(3):502-8 (1996).

Lefebvre et al., "Does O-GlcNAc play a role in neurodegenerative diseases?," Expert Rev Proteomics. 2(2):265-75 (2005).

Legler et al., "Bovine N-acetyl-beta-D-glucosaminidase: affinity purification and characterization of its active site with nitrogen containing analogs of N-acetylglucosamine," Biochim Biophys Acta. 1080(2):89-95 (1991).

Lemieux et al., "Crystallographic structure of human beta-hexosaminidase A: interpretation of Tay-Sachs mutations and loss of GM2 ganglioside hydrolysis," J Mol Biol. 359(4):913-29 (2006).

(56) References Cited

OTHER PUBLICATIONS

Li et al., "Casein kinase 1 delta phosphorylates tau and disrupts its binding to microtubules," J Biol Chem. 279(16):15938-45 (2004).
Lillelund et al., "Recent developments of transition-state analogue glycosidase inhibitors of non-natural product origin," Chem Rev. 102(2):515-53 (2002).
Liu et al., "A potent inhibitor of beta-N-acetylglucosaminidases: 6-acetamido-6-deoxycastanospermine," Tetrahedron Lett. 32(6):719-20 (1991).
Liu et al., "Accumulation of protein O-GlcNAc modification inhibits proteasomes in the brain and coincides with neuronal apoptosis in brain areas with high O-GlcNAc metabolism," J Neurochem. 89(4):1044-55 (2004).
Liu et al., "C2-amidoglycosylation. Scope and mechanism of nitrogen transfer," J Am Chem Soc. 124(33):9789-97 (2002).
Liu et al., "Glutamine protects isolated rat heart from ischemia/ reperfusion injury through the hexosamine biosynthesis pathway," FASEB J. 20:A317 Abstract only (2006).
Liu et al., "Glutamine-induced protection of isolated rat heart from ischemia/reperfusion injury is mediated via the hexosamine biosynthesis pathway and increased protein O-GlcNAc levels," availble in PMC Jan. 1, 2008, published in final edited form as: J Mol Cell Cardiol. 42(1):177-185 (2007) (17 pages).
Liu et al., "Hexosaminidase inhibitors as new drug candidates for the therapy of osteoarthritis," Chem Biol. 8(7):701-11 (2001).
Liu et al., "Increased hexosamine biosynthesis and protein O-GlcNAc levels associated with myocardial protection against calcium paradox and ischemia," J Mol Cell Cardiol. 40(2):303-12 (2006).
Liu et al., "O-GlcNAcylation regulates phosphorylation of tau: a mechanism involved in Alzheimer's disease," Proc Natl Acad Sci USA. 101(29):10804-9 (2004).
Liu et al., "O-linked N-acetylglucosamine modification of proteins protect isolated perfused rat heart from ischemia/reperfusion injury," FASEB J. 19:A691 Abstract 386.11 (2005).
Liu et al., "Streptozotocin, an O-GlcNAcase inhibitor, blunts insulin and growth hormone secretion," Mol Cell Endocrinol. 194(1-2):135-46 (2002).
Liu et al., "Tau becomes a more favorable substrate for GSK-3 when it is prephosphorylated by PKA in rat brain," J Biol Chem. 279(48):50078-88 (2004).
Lubas et al., "Analysis of nuclear pore protein p62 glycosylation," Biochemistry. 34(5):1686-94 (1995).
Lubas et al., "Functional expression of O-linked GlcNAc transferase. Domain structure and substrate specificity," J Biol Chem. 275(15):10983-8 (2000).
Lubas et al., "O-Linked GlcNAc transferase is a conserved nucleocytoplasmic protein containing tetratricopeptide repeats," J Biol Chem. 272(14):9316-24 (1997).
Macauley et al., "Enzymatic characterization and inhibition of the nuclear variant of human O-GlcNAcase," Carbohydr Res. 344(9):1079-84 (2009).
Macauley et al., "Increasing O-GlcNAc levels: An overview of small-molecule inhibitors of O-GlcNAcase," Biochim Biophys Acta. 1800(2):107-21 (2010).
Macauley et al., "O-GlcNAcase catalyzes cleavage of thioglycosides without general acid catalysis," J Am Chem Soc. 127(49):17202-3 (2005).
Macauley et al., "O-GlcNAcase uses substrate-assisted catalysis: kinetic analysis and development of highly selective mechanism-inspired inhibitors," J Biol Chem. 280(27):25313-22 (2005).
Maier et al., "The X-ray crystal structure of human beta-hexosaminidase B provides new insights into Sandhoff disease," J Mol Biol. 328(3):669-81 (2003).
Marchase et al., "Protection from ischemic and hypovolemic injury by hyperglycemia is transduced by hexosamine biosynthesis and O-linked N-acetylglucosamine on cytoplasmic proteins," Circulation. 110:III-1099 Abstract only (2004).
Mark et al., "Anchimeric assistance in hexosaminidases," Can J Chem. 80(8):1064-74 (2002).
Mark et al., "Crystal structure of human beta-hexosaminidase B: understanding the molecular basis of Sandhoff and Tay-Sachs disease," J Mol Biol. 327(5):1093-109 (2003).
Mark et al., "Crystallographic evidence for substrate-assisted catalysis in a bacterial beta-hexosaminidase," J Biol Chem. 276(13):10330-7 (2001).
Markovic-Housley et al., "Crystal structure of hyaluronidase, a major allergen of bee venom," Structure. 8(10):1025-35 (2000).
Marshall et al., "New insights into the metabolic regulation of insulin action and insulin resistance: role of glucose and amino acids," FASEB J. 5(15):3031-6 (1991).
Mazanetz et al., "Untangling tau hyperphosphorylation in drug design for neurodegenerative diseases," Nat Rev Drug Discov. 6(6):464-79 (2007).
McClain et al., "Altered glycan-dependent signaling induces insulin resistance and hyperleptinemia," Proc Natl Acad Sci USA. 99(16):10695-9 (2002).
McCort et al., "Synthesis and evaluation as glycosidase inhibitors of 2,5-imino-D-glucitol and 1,5-imino-D-mannitol related derivatives," Bioorg Med Chem. 8(1):135-43 (2000).
Miller et al., "Sperm require beta-N-acetylglucosaminidase to penetrate through the egg zona pellucida," Development. 118(4):1279-89 (1993).
Mohan et al., "An Improved Synthesis of 2-Acetamido-2-deoxy-D-gluconohydroximolactone (PUGNAc), a Strong Inhibitor of beta-N-Acetylglucosaminidases," Hely Chim Acta. 83(1): 114-8 (2000).
Myszka et al., "Synthesis and induction of apoptosis in B cell chronic leukemia by diosgenyl 2-amino-2-deoxy-beta-D-glucopyranoside hydrochloride and its derivatives," Carbohydr Res. 338(2):133-41 (2003).
Nagy et al., "Glucosamine inhibits angiotensin II-induced cytoplasmic Ca2+ elevation in neonatal cardiomyocytes via protein-associated O-linked N-acetylglucosamine," Am J Physiol Cell Physiol. 290(1):C57-65 (2006).
Nakata et al., "Enantiospecific total synthesis of (-)-allosamizoline, an aminocyclitol moiety of the insect chitinase inhibitor allosamidin," Tetrahedron Lett. 32(39): 5363-6 (1991).
Ninkovic et al., "Preparation of heterocyclylaminopyrazine derivatives for use as CHK-1 inhibitors," CA152:262750 (2010) (2 pages).
Noble et al., "Inhibition of glycogen synthase kinase-3 by lithium correlates with reduced tauopathy and degeneration in vivo," Proc Natl Acad Sci USA. 102(19):6990-5 (2005).
Noto et al., "Simple, rapid spectrophotometry of urinary N-acetyl-beta-D-glucosaminidase, with use of a new chromogenic substrate," Clin Chem. 29(10):1713-6 (1983).
Nöt et al., "Glucosamine administration improves survival following trauma-hemorrhage in rats," FASEB J. 20:A1471 Abstract only (2006).
Office Action issued in corresponding European Patent Application No. 13834204.3 dated Oct. 12, 2016.
Ogawa et al., "Synthesis of a carba-sugar analog of trehalosamine, [(1S)-(1,2,4/3,5)-2-amino-3,4-dihydroxy-5-hydroxymethyl-1-cyclohexyl] alpha-D-glucopyranoside, and a revised synthesis of its beta anomer," Carbohydr Res. 206(2):352-60 (1990).
Ogawa et al., "Synthesis of an ether-linked alkyl 5a-carba-beta-D-glucoside, a 5a-carba-beta-D-galactoside, a 2-acetamido-2-deoxy-5a-carba-beta-D-glucoside, and an alkyl 5a'-carba-beta-lactoside," Carbohydr Res. 337(21-23):1979-92 (2002).
Ogawa et al., "Synthesis of DL-2-amino-2-deoxyvalidamine and its three diastereoisomers," Carbohydr Res. 204:51-64 (1990).
Okuyama et al., "Cytosolic O-GlcNAc accumulation is not involved in beta-cell death in HIT-T15 or Min6," Biochem Biophys Res Commun. 287(2):366-71 (2001).
Overkleeft et al., "A facile transformation of sugar lactones to azasugars," Tetrahedron. 50(14):4215-24 (1994).
Pajouhesh et al., "Medicinal chemical properties of successful central nervous system drugs," NeuroRx. 2(4):541-53 (2005).
Parker et al., "Hyperglycemia and inhibition of glycogen synthase in streptozotocin-treated mice: role of O-linked N-acetylglucosamine," J Biol Chem. 279(20):20636-42 (2004).

(56) References Cited

OTHER PUBLICATIONS

Pickhardt et al., "Anthraquinones inhibit tau aggregation and dissolve Alzheimer's paired helical filaments in vitro and in cells," J Biol Chem. 280(5):3628-35 (2005).
Popowycz et al., "Syntheses and glycosidase inhibitory activities of 2-(aminomethyl)-5-(hydroxymethyl)pyrrolidine-3,4-diol derivatives," Helvetica Chimica Acta. 87(4):800-10 (2004).
Rao et al., "Structural insights into the mechanism and inhibition of eukaryotic O-GlcNAc hydrolysis," EMBO J. 25(7):1569-78 (2006).
Rautio et al., "Prodrugs: design and clinical applications," Nat Rev Drug Discov. 7(3):255-70 (2008).
Reid et al., "Inhibition of membrane-bound lytic transglycosylase B by NAG-thiazoline," FEBS Lett. 574(1-3):73-9 (2004).
Reid et al., "The effect of NAG-thiazoline on morphology and surface hydrophobicity of *Escherichia coli*," FEMS Microbiol Lett. 234(2):343-8 (2004).
Rejman et al., "The synthesis and conformation of dihydroxypiperidinyl derivates of nucleobases as novel iminosugar nucleoside analogs," Eur J Org Chem. 2011(11):2172-87 (2011).
Rempel et al., "Covalent inhibitors of glycosidases and their applications in biochemistry and biology," Glycobiology. 18(8):570-86 (2008).
Riley et al., "Alzheimer's neurofibrillary pathology and the spectrum of cognitive function: findings from the Nun Study," Ann Neurol. 51(5):567-77 (2002).
Ritter et al., "Synthesis of N-acetylglucosamine thiazoline/lipid II hybrids," Tetrahedron Letters. 42:615-8 (2001).
Roeser et al., "Role of sugar hydroxyl groups in glycoside hydrolysis. Cleavage mechanism of deoxyglucosides and related substrates by beta-glucosidase A3 from Aspergillus wentii," Biochim Biophys Acta. 657(2):321-33 (1981).
Roos et al., "O glycosylation of an Sp1-derived peptide blocks known Sp1 protein interactions," Mol Cell Biol. 17(11):6472-80 (1997).
Roos et al., "Streptozotocin, an analog of N-acetylglucosamine, blocks the removal of O-GlcNAc from intracellular proteins," Proc Assoc Am Physicians. 110(5):422-32 (1998).
Roquemore et al., "Dynamic O-GlcNAcylation of the small heat shock protein alpha B-crystallin," Biochemistry. 35(11):3578-86 (1996).
Rosen et al., "Asymmetric synthesis and properties of the enantiomers of the antibacterial agent 7-(3-aminopyrrolidin-1-yl)-1-(2,4-difluorophenyl)-1,4-dihydro-6-fluoro-4-oxo-1,8-naphthyridine-3-carboxylic acid hydrochloride," J Med Chem. 31(8):1586-90 (1988).
Rosen et al., "Design, synthesis, and properties of (4S)-7-(4-amino-2-substituted-pyrrolidin-1-yl)quinolone-3-carboxylic acids," J Med Chem. 31(8):1598-1611 (1988).
Rountree et al., "Design, synthesis, and biological evaluation of enantiomeric beta-N-acetylhexosaminidase inhibitors LABNAc and DABNAc as potential agents against Tay-Sachs and Sandhoff disease," ChemMedChem. 4(3):378-92 (2009).
Rountree et al., "Efficient synthesis from d-lyxonolactone of 2-acetamido-1,4-imino-1,2,4-trideoxy-l-arabinitol LABNAc, a potent pyrrolidine inhibitor of hexosaminidases," Tetrahedron Letters. 48(24):4287-91 (2007).
Sakuda et al., "Absolute configuration of allosamizoline, an aminocyclitol derivative of the chitinase inhibitor allosamidin," Agric Biol Chem. 52(6):1615-17 (1988).
Sakuda et al., "Structures of Allosamidins, Novel Insect Chitinase Inhibitors, Produced by Actinomycetes," Agric Bio Chem. 51(12):3251-59 (1987).
Schafer et al., "Failure is an option: learning from unsuccessful proof-of-concept trials," Drug Discov Today. 13(21-22):913-6 (2008).
Sennhauser et al., "Fungal Beta-N-Acetylhexosaminidase. A test system for new Antimicrobials", Advances in Chitin Science. 1:114-9 (1996) (1 page).

Sheldon et al., "Functional analysis of a group A streptococcal glycoside hydrolase Spy1600 from family 84 reveals it is a beta-N-acetylglucosaminidase and not a hyaluronidase," Biochem J. 399(2):241-7 (2006).
Shilvock et al., "Intermediates for incorporation of tetrahydroxypipecolic acid analogues of alpha- and beta-d-mannopyranose into combinatorial libraries: unexpected nanomolar-range hexosaminidase inhibitors. Synthesis of alpha- and beta-homomannojirimycin," Tetrahedron: Asymmetry. 9(19):3505-16 (1998).
Shirai et al., "Preparation of pyrazinylhydroxyacrylamides as histone deacetylase(HDAC) inhibitors," CA147:277638 (2007) (2 pages).
Shitara et al., "A facile synthesis of D-glucose-type gem-diamine 1-N-iminosugars: a new family of glucosidase inhibitors," Bioorg Med Chem. 7(6):1241-6 (1999).
Simpkins et al., "An enantiospecific total synthesis of allosamizoline," Tetrahedron Letters. 33(6):793-6 (1992).
Simpson et al., "Decreased concentrations of GLUT1 and GLUT3 glucose transporters in the brains of patients with Alzheimer's disease," Ann Neurol. 35(5):546-51 (1994).
So et al., "Evaluation of designed ligands by a multiple screening method: application to glycogen phosphorylase inhibitors constructed with a variety of approaches," J Comput Aided Mol Des. 15(7):613-47 (2001).
Steiner et al., Biorg. Med. Chem. Letters, 2008, 18 pp. 1922-1925.
Stubbs et al., "A divergent synthesis of 2-acyl derivatives of PUGNAc yields selective inhibitors of O-GlcNAcase," Org Biomol Chem. 4(5):839-45 (2006).
Tahar et al., "A Flexible Route Towards Five-Membered Ring Imino Sugars and Their Novel 2-Deoxy-2-fluoro Analogues", European Journal of Organic Chemistry, vol. 2003, No. 15, 2903-2910 (2003).
Takahashi et al., "Synthesis of a novel azapseudodisaccharide related to allosamidin employing N,N'-diacetylchitobiose as a key starting material," Tetrahedron. 55(52):14871-84 (1999).
Takahashi et al., "Synthesis of demethylallosamidin, a yeast chitinase inhibitor; use of disaccharide glycosyl donor carrying novel neighboring group," Tetrahedron Letters. 35(24):4149-52 (1994).
Takaoka et al., "Inhibition of N-acetylglucosaminyltransfer enzymes: chemical-enzymatic synthesis of new five-membered acetamido azasugars," J Org Chem. 58(18):4809-12 (1993).
Takebayashi et al., "A Versatile Synthetic Strategy for the Preparation and Discovery of New Iminocyclitols as Inhibitors of Glycosidases," J Org Chem. 64(14):5280-91 (1999).
Terwisscha van Scheltinga et al., "Stereochemistry of chitin hydrolysis by a plant chitinase/lysozyme and x-ray structure of a complex with allosamidin: evidence for substrate assisted catalysis," Biochemistry. 34(48):15619-23 (1995).
Tews et al., "Bacterial chitobiase structure provides insight into catalytic mechanism and the basis of tay-sachs disease," Nat. Struct. Biol. 3(7):638-48 (1996).
Toleman et al., "Characterization of the histone acetyltransferase (HAT) domain of a bifunctional protein with activable O-GlcNAcase and HAT activities," J Biol Chem. 279(51):53665-73 (2004).
Torres et al., "Topography and polypeptide distribution of terminal N-acetylglucosamine residues on the surfaces of intact lymphocytes. Evidence for O-linked GlcNAc," J Biol Chem. 259(5):3308-17 (1984).
Triggs-Raine et al., "Naturally occurring mutations in GM2 gangliosidosis: a compendium," Adv Genet. 44:199-224 (2001).
Tropak et al., "Pharmacological enhancement of beta-hexosaminidase activity in fibroblasts from adult Tay-Sachs and Sandhoff Patients," J Biol Chem. 279(14):13478-87 (2004).
Trost et al., "A general synthetic strategy toward aminocyclopentitol glycosidase inhibitors. Application of palladium catalysis to the synthesis of allosamizoline and mannostatin A," J Am Chem Soc. 115(2):444-58 (1993).
Trost et al., "Template-directed synthesis of (±)-allosamizoline and its 3,4-epimers." J Am Chem Soc. 112(3):1261-3 (1990).

(56) References Cited

OTHER PUBLICATIONS

Tsou et al., "A convenient approach toward the synthesis of enantiopure isomers of DMDP and ADMDP," Tetrahedron. 65(1):93-100 (2009).
Tsuruoka et al., "Inhibition of mouse tumor metastasis with nojirimycin-related compounds," J Antibiot (Tokyo). 49(2):155-61 (1996).
Uchida et al., "Synthesis and biological evaluation of potent glycosidase inhibitors: N-phenyl cyclic isourea derivatives of 5-amino- and 5-amino-C-(hydroxymethyl)-1,2,3,4-cyclopentanetetraols," Bioorg Med Chem. 5(5):921-39 (1997).
Ueno et al., "Purification and properties of neutral beta-N-acetylglucosaminidase from carp blood," Biochim Biophys Acta. 1074(1):79-84 (1991).
Valstar et al., "Mucopolysaccharidosis type IIIB may predominantly present with an attenuated clinical phenotype," J Inherit Metab Dis. 33(6):759-67 (2010).
Van Den Berg et al., "Design and synthesis of 2-acetamidomethyl derivatives of isofagomine as potential inhibitors of human lysosomal beta-hexosaminidases," Bioorg Med Chem. 12(5):891-902 (2004).
Vocadlo et al., "Catalysis by hen egg-white lysozyme proceeds via a covalent intermediate," Nature. 412(6849):835-8 (2001).
Vocadlo et al., "Detailed comparative analysis of the catalytic mechanisms of beta-N-acetylglucosaminidases from families 3 and 20 of glycoside hydrolases," Biochemistry. 44(38):12809-18 (2005).
Vocadlo et al., "Mechanism of action and identification of Asp242 as the catalytic nucleophile of Vibrio furnisii N-acetyl-beta-D-glucosaminidase using 2-acetamido-2-deoxy-5-fluoro-alpha-L-idopyranosyl fluoride," Biochemistry. 39(1):117-26 (2000).
Volpe, "Application of method suitability for drug permeability classification," AAPS J. 12(4):670-8 (2010).
Vosseller et al., "Elevated nucleocytoplasmic glycosylation by O-GlcNAc results in insulin resistance associated with defects in Akt activation in 3T3-L1 adipocytes," Proc Natl Acad Sci USA. 99(8):5313-8 (2002).
Wakabayashi et al., "Preparation of 3,6-di-O-benzylallosamizoline from natural allosamidin," Tetrahedron: Asymmetry. 11(10):2083-91 (2000).
Wells et al., "Dynamic O-glycosylation of nuclear and cytosolic proteins: further characterization of the nucleocytoplasmic beta-N-acetylglucosaminidase, O-GlcNAcase," J Biol Chem. 277(3):1755-61 (2002).
Wells et al., "Glycosylation of nucleocytoplasmic proteins: signal transduction and O-GlcNAc," Science. 291(5512):2376-8 (2001).
Wells et al., "O-GlcNAc transferase is in a functional complex with protein phosphatase 1 catalytic subunits," J Biol Chem. 279(37):38466-70 (2004).
Wennekes et al., "The development of an aza-c-glycoside library based on a tandem staudinger/aza-wittig/ugi three-component reaction," Eur J Org Chem. 2012(32):6420-54 (2012).
Whitworth et al., "Analysis of PUGNAc and NAG-thiazoline as transition state analogues for human O-GlcNAcase: mechanistic and structural insights into inhibitor selectivity and transition state poise," J Am Chem Soc. 129(3):635-44 (2007).
Williams et al., "Tauopathies: classification and clinical update on neurodegenerative diseases associated with microtubule-associated protein tau," Intern Med J. 36(10):652-60 (2006).
Win-Mason et al., "Stereoselective total synthesis of aminoiminohexitols via carbamate annulation," J Org Chem. 76(23):9611-21 (2011).
Wrodnigg et al., "Biologically active 1-aminodeoxy and 1-o-alkyl derivatives of the powerful d-glucosidase inhibitor 2,5-dideoxy-2,5-imino-d-mannitol," J Carb Chem. 19(8):975-90 (2000).
Wrodnigg et al., "Synthesis of 1-amino-1,2,5-trideoxy-2,5-imino-D-mannitol, a novel analogue of the powerful glucosidase inhibitor 2,5-dideoxy-2,5-imino-D-mannitol, via an amadori rearrangement of 5-azido-5-deoxy-D-glucofuranose," Tetrahedron Lett. 38(31):5463-6 (1997).
Yamada et al., "Preventive and therapeutic effects of large-dose nicotinamide injections on diabetes associated with insulitis. An observation in nonobese diabetic (NOD) mice," Diabetes. 31(9):749-53 (1982).
Yamamoto et al., "Streptozotocin and alloxan induce DNA strand breaks and poly(ADP-ribose) synthetase in pancreatic islets," Nature. 294(5838):284-6 (1981).
Yang et al., "Glucosamine administration during resuscitation improves organ function after trauma hemorrhage," Shock. 25(6):600-7 (2006).
Yang et al., "Modification of p53 with O-linked N-acetylglucosamine regulates p53 activity and stability," Nat Cell Biol. 8(10):1074-83 (2006).
Yao et al., "Reduction of O-linked N-acetylglucosamine-modified assembly protein-3 in Alzheimer's disease," J Neurosci. 18(7):2399-411 (1998).
Yoshimura et al., "Synthesis of both enantiomers of hydroxypipecolic acid derivatives equivalent to 5-azapyranuronic acids and evaluation of their inhibitory activities against glycosidases," Bioorg Med Chem. 16(17):8273-86 (2008).
Yuzwa et al., "A potent mechanism-inspired O-GlcNAcase inhibitor that blocks phosphorylation of tau in vivo," Nat Chem Biol. 4(8):483-90 (2008).
Zachara et al., "Dynamic O-GlcNAc modification of nucleocytoplasmic proteins in response to stress. A survival response of mammalian cells," J Biol Chem. 279(29):30133-42 (2004).
Zachara et al., "Increased O-GlcNAc in response to stress, a survival response of mammals," Conference Abstracts of Joint Meeting of the Society for Glycobiology and the Japanese Society of Carbohydrate Research. 1170 Abstract 418 (2004).
Zechel et al., "Glycosidase mechanisms: Anatomy of a finely tuned catalyst," Acc. Chem. Res. 33(1):11-18 (2000).
Zhang et al., "O-GlcNAc modification is an endogenous inhibitor of the proteasome," Cell 115:715-725 (2003).
Zhou et al., "Lysosomal Glycosphingolipid Recognition by NKT Cells," Science 306(5702):1786-1789 (2004).
Zhu et al., "Insulin signaling, diabetes mellitus and risk of Alzheimer disease," J Alzheimers Dis. 7(1):81-4 (2005).
Zou et al., "Glucosamine improves recovery following trauma hemorrhage in rat," FASEB J 19: A1224 Abstract only (2005).
Zou et al., "Increasing protein O-GlcNAc levels by inhibition of O-GlcNAcase improves cardiac function following trauma hemorrhage and resuscitation in rat," FASEB J. 20:A1471 Abstract only (2006).
Zou et al., "The protective effects of pugnac on cardiac function after trauma-hemorrhage are mediated via increased protein O-GLcNAc levels," Shock 27(4):402-408 (2007).
Al-Rawi et al., "Synthesis and Biochemical Properties of Reversible Inhibitors of UDP-N-Acetylglucosamine 2-Epimerase," Angew. Chem. Int. Ed. 43:4366-4370 (2004).
Office Action issued in corresponding European Patent Application No. 13834204.3 dated May 18, 2017 (7 pages).
Limbach et al., "Synthesis of Beta3-Homophenylalanine-Derived Amino Acids and Peptides by Suzuki Coupling in Solution and on Solid Support," Helv. Chim. Acta 89: 1427-1441 (2006).
Góbi et al., "Is Beta-homo-proline a pseudo-gamma-turn forming element of beta-peptides? an IR and VCD spectroscopic study on Ac-beta-HPro-NHMe in cryogenic matrices and solutions," Phys. Chem. Chem. Phys. 12: 13603-13615 (2010).
Rabiczko et al., "Syntheses of pyrrolizidines and indolizidines from alpha,beta-unsaturated sugar delta-lactones via Dieckmann condensation," Tetrahedron 58: 1433-1441 (2002).

* cited by examiner

GLYCOSIDASE INHIBITORS AND USES THEREOF

FIELD OF THE INVENTION

This application relates to compounds which inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as glycoprotein 2-acetamido-2-deoxy-β-D-glucopyranosidase (O-GlcNAcase)[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the brain.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27-29] The precise causes of this hyperphosphorylation of tau remain elusive. Accordingly, considerable effort has been dedicated toward: a) elucidating the molecular physiological basis of tau hyperphosphorylation;[30] and b) identifying strategies that could limit tau hyperphosphorylation in the hope that these might halt, or even reverse, the progression of Alzheimer's disease[31-34] Thus far, several lines of evidence suggest that up-regulation of a number of kinases may be involved in hyperphosphorylation of tau,[21,35,36] although very recently, an alternative basis for this hyperphosphorylation has been advanced.[21]

In particular, it has emerged that phosphate levels of tau are regulated by the levels of O-GlcNAc on tau. The presence of O-GlcNAc on tau has stimulated studies that correlate 0-GlcNAc levels with tau phosphorylation levels. The interest in this field stems from the observation that O-GlcNAc modification has been found to occur on many proteins at amino acid residues that are also known to be phosphorylated.[37-39] Consistent with this observation, it has been found that increases in phosphorylation levels result in decreased O-GlcNAc levels and conversely, increased O-GlcNAc levels correlate with decreased phosphorylation levels.[40] This reciprocal relationship between O-GlcNAc and phosphorylation has been termed the "Yin-Yang hypothesis"[41] and has gained strong biochemical support by the discovery that the enzyme OGT[4] forms a functional complex with phosphatases that act to remove phosphate groups from proteins.[42] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,43] Hyperphosphorylated tau in human AD brains has markedly lower levels of O-GlcNAc than are found in healthy human brains.[21] It has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[44] Within the brains of AD patients marked decreases in glucose utilization occur and are thought to be a potential cause of neurodegeneration.[45] The basis for this decreased glucose supply in AD brain[46-48] is thought to stem from any of decreased glucose transport,[49,50] impaired insulin signaling,[51,52] and decreased blood flow.[53]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[54] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[55,56] and binding partners[42,57] through its tetratricopeptide repeat (TPR) domains.[58,59] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites,[10,38,39,60] including tau and neurofilaments.[61] Additionally, OGT shows unusual kinetic behaviour making it exquisitely sensitive to intracellular UDP-GlcNAc substrate concentrations and therefore glucose supply.[42]

Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[45] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[62] comes from recent studies showing that when transgenic mice harbouring human tau are treated with kinase inhibitors, they do not develop typical motor defects[34] and, in another case,[33] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[63]

Small-molecule O-GlcNAcase inhibitors, to limit tau hyperphosphorylation, have been considered for treatment of AD and related tauopathies.[64] Specifically, the O-GlcNAcase inhibitor thiamet-G has been implicated in the reduction of tau phosphorylation in cultured PC-12 cells at pathologically relevant sites.[64] Moreover, oral administration of thiamet-G to healthy Sprague-Dawley rats has been implicated in reduced phosphorylation of tau at Thr231, Ser396 and Ser422 in both rat cortex and hippocampus.[64]

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion,[65-71] trauma hemorrhage,[72-74] hypervolemic shock,[75] and calcium paradox.[65,76] Moreover, strong evidence indicates that these cardioprotective effects are mediated by elevated levels of protein O-GlcNAc modification.[65,66,68,71,73,76-79] There is also evidence that the O-GlcNAc modification plays a role in a variety of neurodegenerative diseases, including Parkinson's disease and Huntington's disease.[80]

Humans have three genes encoding enzymes that cleave terminal β-N-acetylglucosamine residues from glycoconjugates. The first of these encodes O-GlcNAcase. O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[81,82] O-GlcNAcase acts to hydrolyse O-GlcNAc off of serine and threonine residues of post-translationally modified proteins.[1,6,7,83,84] Consistent with the presence of O-GlcNAc on many intracellular proteins, the enzyme O-GlcNAcase appears to have a role in the etiology of several diseases including type II diabetes,[14,85] AD[16,21,86] and cancer.[22,87] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[88] These enzymatic deficiencies cause an accumulation of glycolipids and glycoconjugates in the lysosomes resulting in neurological impairment and deformation. The deleterious effects of accumulation of gangliosides at the organismal level are still being uncovered.[89]

As a result of the biological importance of these β-N-acetyl-glucosaminidases, small molecule inhibitors of glycosidases[90-93] have received a great deal of attention,[94] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, many compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenyl-carbamate (PUGNAc).[14,95-98]

STZ has long been used as a diabetogenic compound because it has a particularly detrimental effect on β-islet cells.[99] STZ exerts its cytotoxic effects through both the alkylation of cellular DNA[99,100] as well as the generation of radical species including nitric oxide.[101] The resulting DNA strand breakage promotes the activation of poly(ADP-ribose) polymerase (PARP)[102] with the net effect of depleting cellular NAD+ levels and, ultimately, leading to cell death.[103,104] Other investigators have proposed instead that STZ toxicity is a consequence of the irreversible inhibition of O-GlcNAcase, which is highly expressed within β-islet cells.[95,105] This hypothesis has, however, been brought into question by two independent research groups.[106,107] Because cellular O-GlcNAc levels on proteins increase in response to many forms of cellular stress[108] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[109] and although it has been proposed by others that STZ acts to irreversibly inhibit O-GlcNAcase,[110] there has been no clear demonstration of this mode of action. More recently, it has been shown that STZ does not irreversibly inhibit O-GlcNAcase.[111]

NAG-thiazoline has been found to be a potent inhibitor of family 20 hexosaminidases,[93,112] and more recently, the family 84 O-GlcNAcases.[111] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,113] and the family 20 human β-hexosaminidases.[114] This molecule, developed by Vasella and coworkers, was found to be a potent competitive inhibitor of the β-N-acetyl-glucosaminidases from *Canavalia ensiformis, Mucor rouxii*, and the β-hexosaminidase from bovine kidney.[91] It has been demonstrated that administration of PUGNAc in a rat model of trauma hemorrhage decreases circulating levels of the pro-inflammatory cytokines TNF-α and IL-6.[115] It has also been shown that administration of PUGNAc in a cell-based model of lymphocyte activation decreases production of the cytokine IL-2.[116] Subsequent studies have indicated that PUGNAc can be used in an animal model to reduce myocardial infarct size after left coronary artery occlusions.[117] Of particular significance is the fact that elevation of O-GlcNAc levels by administration of PUGNAc, an inhibitor of O-GlcNAcase, in a rat model of trauma hemorrhage improves cardiac function.[115,118] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[119]

More recently, it has been suggested that the selective O-GlcNAcase inhibitor NButGT exhibits protective activity in cell-based models of ischemia/reperfusion and cellular stresses, including oxidative stress.[120] This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar. 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; PCT/CA2009/001302, filed 16 Sep. 2009, published under WO 2010/037207 on 8 Apr. 2010; PCT/CA2011/000548, filed 10 May 2011, published under No. WO 2011/140640 on 17 Nov. 2011; PCT/CA/2011/001241, filed 8 Nov. 2011, published under WO 2012/061927 on 18 May 2012; PCT/US2011/059668, filed 8 Nov. 2011, published under WO 2012/064680 on 18 May 2012; and PCT/CA2011/001397, filed 21 Dec. 2011, published under WO 2012/083435 on 28 Jun. 2012, describe selective inhibitors of O-GlcNAcase.

SUMMARY OF THE INVENTION

The invention provides, in part, compounds for inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, and/or accumulation or deficiency of O-GlcNAc.

In one aspect, the invention provides a compound of Formula (I) or a pharmaceutically acceptable salt thereof:

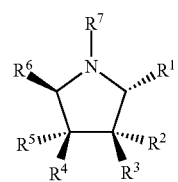

(I)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (I) in which at least one of $R^2$, $R^3$, $R^4$, or $R^5$ may be OH; or $R^1$ may be $CH_2OH$; or $R^6$ may be $CH_2OH$.

In alternative embodiments, the invention provides a compound of Formula (I) in which at least one of $R^2$, $R^3$, $R^4$, or $R^5$ may be F; or $R^1$ may be $CH_2F$ or $CHF_2$; or $R^6$ may be $CH_2F$ or $CHF_2$.

In alternative embodiments, the invention provides a compound of Formula (I) in which $R^1$ may be $CH_3$; or $R^2$ and $R^3$ may be H; or $R^4$ and $R^5$ may be H; or $R^6$ may be $CH_3$.

In alternative embodiments, the invention provides a compound of Formula (I) in which $R^1$ or $R^6$ may be independently H.

In alternative embodiments, the invention provides a compound of Formula (I) in which at least one of $R^1$ or $R^6$ may be other than H.

In alternative embodiments, the invention provides a compound of Formula (I) in which $R^1$ may be other than H.

In alternative embodiments, the invention provides a compound of Formula (I) in which $R^6$ may be other than H.

In alternative embodiments, the invention provides a compound of Formula (I) in which $R^1$ and $R^6$ may be other than H.

In alternative embodiments, the invention provides a compound of Formula (I) in which at least one of $R^2$ or $R^3$ may be other than H.

In alternative embodiments, the invention provides a compound of Formula (I) in which at least one of $R^4$ or $R^5$ may be other than H.

In alternative embodiments, the invention provides a compound of Formula (I) in which at least one of $R^2$, $R^3$, $R^4$, or $R^5$ may be other than H.

In alternative embodiments, the invention provides a compound of Formula (I) in which at least one of $R^1$, $R^2$, $R^3$, $R^4$, $R^5$, or $R^6$ may be other than H.

In alternative embodiments, the invention provides a compound of Formula (I) in which at least one of $R^1$ or $R^6$ may be other than $CH_3$.

In alternative embodiments, the invention provides a compound of Formula (I) in which $R^7$ may be other than H.

In alternative embodiments, the invention provides a compound of Formula (Ia) or a pharmaceutically acceptable salt thereof:

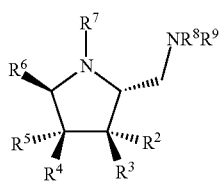

(Ia)

where $R^8$ may be H or $C_{1-6}$ alkyl; $R^9$ may be $C_{1-6}$ acyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ib) or a pharmaceutically acceptable salt thereof:

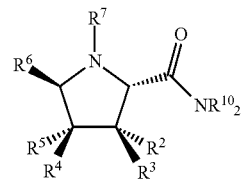

(Ib)

where each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ic) or a pharmaceutically acceptable salt thereof:

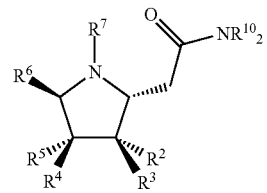

(Ic)

where each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Id) or a pharmaceutically acceptable salt thereof:

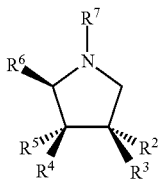

(Id)

where $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of H, $CH_3$, $CH_2F$, $CHF_2$, and $CH_2OH$; and $R^7$ may be selected from the group consisting of H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ie) or a pharmaceutically acceptable salt thereof:

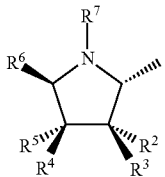

(Ie)

where $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of H, $CH_3$, $CH_2F$, $CHF_2$, and $CH_2OH$; and $R^7$ may be selected from the group consisting of H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (If) or a pharmaceutically acceptable salt thereof:

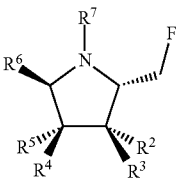

(If)

where $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ig) or a pharmaceutically acceptable salt thereof:

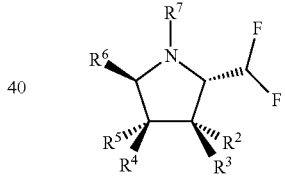

(Ig)

where $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ih) or a pharmaceutically acceptable salt thereof:

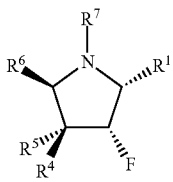

(Ih)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ii) or a pharmaceutically acceptable salt thereof:

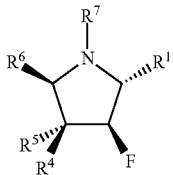

(Ii)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ij) or a pharmaceutically acceptable salt thereof:

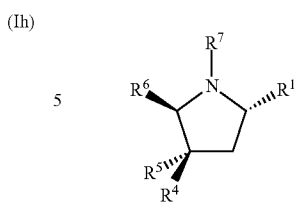

(Ij)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ik) or a pharmaceutically acceptable salt thereof:

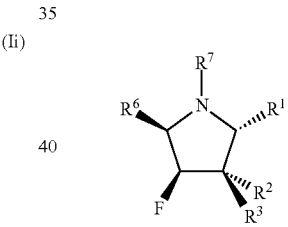

(Ik)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Il) or a pharmaceutically acceptable salt thereof:

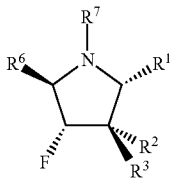

(II)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Im) or a pharmaceutically acceptable salt thereof:

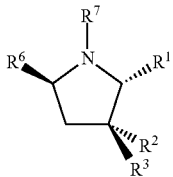

(Im)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (In) or a pharmaceutically acceptable salt thereof:

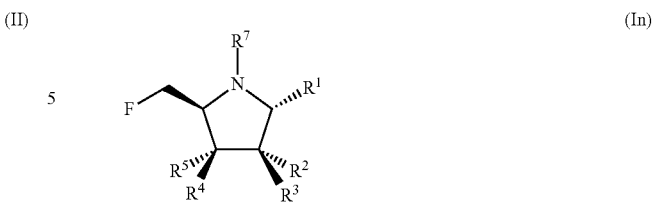

(In)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Io) or a pharmaceutically acceptable salt thereof:

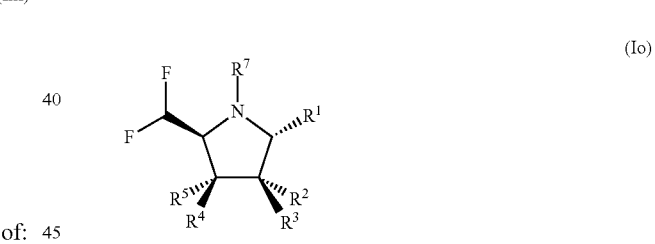

(Io)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ip) or a pharmaceutically acceptable salt thereof:

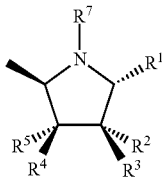

(Ip)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Iq) or a pharmaceutically acceptable salt thereof:

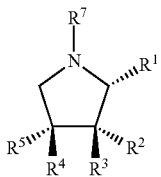

(Iq)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (II) or a pharmaceutically acceptable salt thereof:

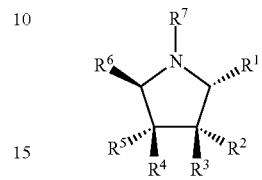

(II)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl; with the proviso that $R^7$ excludes benzyl, 4-hydroxybenzyl, 4-(pyridin-2-yl)benzyl, $(CH_2)_2$phenyl, $C(O)CH_3$, [1,1'-biphenyl]-4-ylmethyl, (R)-1-phenylethyl, (S)-1-phenylethyl, $CH(phenyl)_2$, and 4-fluorophenethyl.

In alternative embodiments, the compound may be a prodrug; the compound may selectively inhibit an O-glycoprotein 2-acetamido-2-deoxy-β-D-glucopyranosidase (0-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative embodiments, a compound according to Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (In), Formula (Io), Formula (Ip), or Formula (Iq) may have enhanced permeability.

In alternative embodiments, a compound according to Formula (Ia), Formula (Ib), or Formula (Ic) may have enhanced selectivity.

In alternative embodiments, a compound according to Formula (If), Formula (Ig), Formula (Ih), Formula (Ii), Formula (Ik), Formula (Il), Formula (In), or Formula (Io) may have enhanced permeability.

In alternative embodiments, a compound according to Formula (Id), Formula (Ie), Formula (Ij), Formula (Im), Formula (Ip), or Formula (Iq) may have enhanced permeability.

In alternative aspects, the invention provides a pharmaceutical composition including a compound according to the invention, in combination with a pharmaceutically acceptable carrier.

In alternative aspects, the invention provides methods of selectively inhibiting an O-GlcNAcase, or of inhibiting an O-GlcNAcase in a subject in need thereof, or of increasing the level of O-GlcNAc, or of treating a neurodegenerative disease, a tauopathy, cancer or stress, in a subject in need thereof, by administering to the subject an effective amount of a compound of Formula (I) or a pharmaceutically acceptable salt thereof:

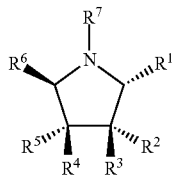

(I)

where $R^1$ may be selected from the group consisting of: $CH_2NR^8R^9$, $(CH_2)_nC(O)NR^{10}{}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. The condition may be Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Parkinson's disease, Schizophrenia, Mild Cognitive Impairment (MCI), Neuropathy (including peripheral neuropathy, autonomic neuropathy, neuritis, and diabetic neuropathy), or Glaucoma. The stress may be a cardiac disorder, e.g., ischemia; hemorrhage; hypovolemic shock; myocardial infarction; an interventional cardiology procedure; cardiac bypass surgery; fibrinolytic therapy; angioplasty; or stent placement.

In alternative aspects, the invention provides a method of treating an O-GlcNAcase-mediated condition that excludes a neurodegenerative disease, a tauopathy, cancer or stress, in a subject in need thereof, by administering to the subject an effective amount of a compound of Formula (I) or a pharmaceutically acceptable salt thereof:

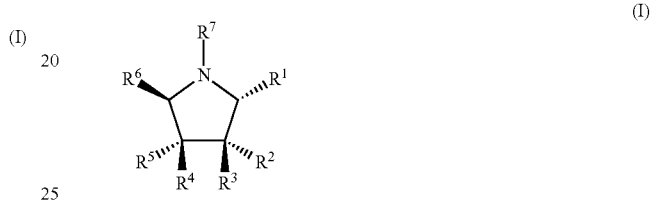

(I)

where $R^1$ may be selected from the group consisting of: $CH_2NR^8R^9$, $(CH_2)C(O)NR^{10}{}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. In some embodiments, the condition may be inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, and eosiniphilic fasciitis; graft rejection, in particular but not limited to solid organ transplants, such as heart, lung, liver, kidney, and pancreas transplants (e.g. kidney and lung allografts); epilepsy; pain; fibromyalgia; stroke, e.g., neuroprotection following a stroke.

In alternative embodiments, the administering may increase the level of O-GlcNAc in the subject. The subject may be a human.

In alternative aspects, the invention provides use of a compound of an effective amount of a compound of Formula (I) or a pharmaceutically acceptable salt thereof:

(I)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl, in the preparation of a medicament. The medicament may be for selectively inhibiting an O-GlcNAcase, for increasing the level of O-GlcNAc, for treating a condition modulated by an O-GlcNAcase, for treating a neurodegenerative disease, a tauopathy, a cancer, or stress.

In alternative aspects, the invention provides a method for screening for a selective inhibitor of an O-GlcNAcase, by a) contacting a first sample with a test compound; b) contacting a second sample with a compound of Formula (I)

(I)

where $R^1$ may be selected from the group consisting of: $CH_2NR^8R^9$, $(CH_2)_nC(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl; c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formula (I).

This summary of the invention does not necessarily describe all features of the invention.

DETAILED DESCRIPTION

The invention provides, in part, novel compounds that are capable of inhibiting an O-glycoprotein 2-acetamido-2-deoxy-β-D-glucopyranosidase (O-GlcNAcase). In some embodiments, the O-GlcNAcase may be a mammalian O-GlcNAcase, such as a rat, mouse or human O-GlcNAcase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability ($P_{eff}$) or apparent peameability ($P_{app}$) are reviewed for example by Volpe in *The AAPSJournal*, 2010, 12(4), 670-678. In some embodiments, one or more of the compounds according to the invention may show enhanced permeability when tested in one or more of these assays for determining $P_{eff}$ or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, (3aR,5R,6S,7R, 7aR)-5-(hydroxymethyl)-2-propyl-5,6,7,7a-tetrahydro-3aH-pyrano[3,2-d]thiazole-6,7-diol, or (3aR,5R,6S,7R,7aR)-2-(ethylamino)-5-(hydroxymethyl)-5,6,7,7a-tetrahydro-3aH-pyrano[3,2-d]thiazole-6,7-diol, or (3aR,5R,6S,7R,7aR)-2-(dimethylamino)-5-(hydroxymethyl)-5,6,7,7a-tetrahydro-3aH-pyrano[3,2-d]thiazole-6,7-diol. In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2 \times 10^{-6}$ cm/s in the assay described below for determination of $P_{app}$ in LLC-PK1 cells. In alternative embodiments, "enhanced permeability" means a $P_{app}$ value in the range $2 \times 10^{-6}$ cm/s to $35 \times 10^{-6}$ cm/s in the assay described below for determination of $P_{app}$ in LLC-PK1 cells.

In some embodiments, a compound according to the invention may exhibit superior selectivity in inhibiting an O-GlcNAcase. In some embodiments, one or more of the compounds according to the invention may be more selective for an O-GlcNAcase over a β-hexosaminidase. In some embodiments, one or more of the compounds may selectively inhibit the activity of a mammalian O-GlcNAcase over a mammalian β-hexosaminidase. In some embodiments, a selective inhibitor of an O-GlcNAcase may not substantially inhibit a β-hexosaminidase. In some embodiments, the β-hexosaminidase may be a mammalian β-hexosaminidase, such as a rat, mouse or human β-hexosaminidase. A compound that "selectively" inhibits an O-GlcNAcase is a compound that may inhibit the activity or biological function of an O-GlcNAcase, but may not substantially inhibit the activity or biological function of a β-hexosaminidase. For example, in some embodiments, a selective inhibitor of an O-GlcNAcase may selectively inhibit the cleavage of 2-acetamido-2-deoxy-β-D-glucopyranoside (O-GlcNAc) from polypeptides. In some embodiments, a selective inhibitor of an O-GlcNAcase may selectively bind to an O-GlcNAcase. In some embodiments, a selective inhibitor of an O-GlcNAcase may inhibit hyperphosphorylation of a tau protein and/or inhibit formations of NFTs. By "inhibit," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase may elevate or enhance O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase may exhibit a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

One or more of the compounds of the present invention may elevate O-GlcNAc levels on O-GlcNAc-modified polypeptides or proteins in vivo specifically via interaction with an O-GlcNAcase enzyme, and may be effective in treating conditions which require or respond to inhibition of O-GlcNAcase activity.

In some embodiments, one or more of the compounds of the present invention may be useful as agents that produce a decrease in tau phosphorylation and NFT formation. In some embodiments, one or more of the compounds may therefore be useful to treat Alzheimer's disease and related tauopathies. In some embodiments, one or more of the compounds may thus be capable of treating Alzheimer's disease and related tauopathies by lowering tau phosphorylation and reducing NFT formation as a result of increasing tau O-GlcNAc levels. In some embodiments, one or more of the compounds may produce an increase in levels of O-GlcNAc modification on O-GlcNAc-modified polypeptides or proteins, and may therefore be useful for treatment of disorders responsive to such increases in O-GlcNAc modification; these disorders may include, without limitation, neurodegenerative, inflammatory, cardiovascular, and immunoregulatory diseases. In some embodiments, a compound may also be useful as a result of other biological activities related to its ability to inhibit the activity of glycosidase enzymes. In alternative embodiments, one or more of the compounds of the invention may be valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In specific embodiments, the invention provides compounds described generally by Formula (I) and the salts, prodrugs, and enantiomeric forms thereof:

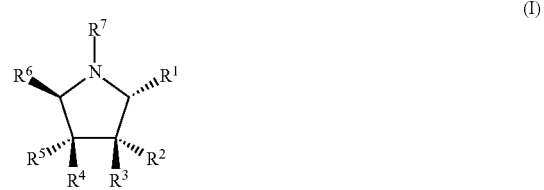

(I)

As set forth in Formula (I): $R^1$ may be selected from the group consisting of: $CH_2NR^8R^9$, $(CH_2)_nC(O)NR^{10}{}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl; $R^2$ may be H and $R^3$ may be OH, or $R^2$ may be H and $R^3$ may be H, or $R^2$ may be H and $R^3$ may be F, or $R^2$ may be F and $R^3$ may be H, or $R^2$ may be F and $R^3$ may be F, or $R^2$ may be OH and $R^3$ may be H; $R^4$ may be H and $R^5$ may be OH, or $R^4$ may be H and $R^5$ may be H, or $R^4$ may be H and $R^5$ may be F, or $R^4$ may be F and $R^5$ may be H, or $R^4$ may be F and $R^5$ may be F, or $R^4$ may be OH and $R^5$ may be H; $R^6$ may be selected from the group consisting of: H, $CH_3$, $CH_2F$, $CHF_2$, and $CH_2OH$; and $R^7$ may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In some embodiments, $R^1$ as set forth in Formula (I) may be selected from the group consisting of: $CH_2NR^8R^9$, $(CH_2)_n C(O)NR^{10}_2$, H, $CH_3$, $CH_2F$, $CHF_2$, and $CH_2OH$, where $R^8$ may be H or $C_{1-6}$ alkyl, $R^9$ may be $C_{1-6}$ acyl, n may be 0 or 1, and each $R^{10}$ may be independently H or $C_{1-6}$ alkyl. In some embodiments, $R^1$ may be $CH_2NR^8R^9$, where $R^8$ may be H or $C_{1-6}$ alkyl, and $R^9$ may be $C_{1-6}$ acyl. In some embodiments, $R^1$ may be $CH_2NR^8R^9$, where $R^8$ may be H, and $R^9$ may be $C(O)CH_3$, $C(O)CH_2CH_3$, or $C(O)(CH_2)_2CH_3$. In some embodiments, $R^1$ may be $C(O)NR^{10}_2$, where each $R^{10}$ may be independently H or $C_{1-6}$ alkyl. In some embodiments, $R^1$ may be $(CH_2)C(O)NR^{10}_2$, where each $R^{10}$ may be independently H or $C_{1-6}$ alkyl. In some embodiments, $R^1$ may be $C(O)NHR^{10}$, where $R^{10}$ may be H or $C_{1-6}$ alkyl. In some embodiments, $R^1$ may be $(CH_2)C(O)NHR^{10}$, where $R^{10}$ may be H or $C_{1-6}$ alkyl. In some embodiments, $R^1$ may be selected from the group consisting of: $CH_2NH(C(O)CH_3)$, $CH_2NH(C(O)CH_2CH_3)$, $C(O)NHCH_3$, $C(O)NHCH_2CH_3$, $C(O)NH(CH_2)_2CH_3$, $(CH_2)C(O)NHCH_3$, and $(CH_2)C(O)NHCH_2CH_3$. In some embodiments, $R^1$ may be $CH_2OH$. In some embodiments, $R^1$ may be $CH_2F$. In some embodiments, $R^1$ may be $CHF_2$. In some embodiments, $R^1$ may be $CH_3$. In some embodiments, $R^1$ may be H.

In some embodiments, $R^2$ as set forth in Formula (I) may be H, F, or OH. In some embodiments, $R^2$ may be H or F. In some embodiments, $R^2$ may be F. In some embodiments, $R^2$ may be OH.

In some embodiments, $R^3$ as set forth in Formula (I) may be H, F, or OH. In some embodiments, $R^3$ may be H or F. In some embodiments, $R^3$ may be F. In some embodiments, $R^3$ may be H.

In some embodiments, $R^4$ as set forth in Formula (I) may be H, F, or OH. In some embodiments, $R^4$ may be H or F. In some embodiments, $R^4$ may be F. In some embodiments, $R^4$ may be H.

In some embodiments, $R^5$ as set forth in Formula (I) may be H, F, or OH. In some embodiments, $R^5$ may be H or F. In some embodiments, $R^5$ may be F. In some embodiments, $R^5$ may be OH.

In some embodiments, $R^6$ as set forth in Formula (I) may be selected from the group consisting of: H, $CH_3$, $CH_2F$, $CHF_2$, and $CH_2OH$. In some embodiments, $R^6$ may be $CH_2OH$. In some embodiments, $R^6$ may be $CH_2F$ or $CHF_2$. In some embodiments, $R^6$ may be $CH_3$. In some embodiments, $R^6$ may be H.

In some embodiments, $R^7$ as set forth in Formula (I) may be selected from the group consisting of: H, $C_{1-18}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. In some embodiments, $R^7$ may be selected from the group consisting of: $C_{1-18}$ alkyl, $C_{7-20}$ arylalkyl, and $C_{2-20}$ heteroarylalkyl, each optionally substituted from one to four substituents with one of more of halo, OH, $OCH_3$, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. In some embodiments, $R^7$ may be selected from the group consisting of: H, $CH_3$, $(CH_2)_2$(phenyl), $(CH_2)_3$(phenyl), $(CH_2)_4$(phenyl), 3-(4-methoxyphenyl)propyl, 3-([1,1'-biphenyl]-4-yl)propyl, 2-([1,1'-biphenyl]-4-yl)ethyl, $(CH_2)$(3-pyridyl), $(CH_2)$(2-pyridyl), ([1,1-biphenyl]-4-yl)methyl$(CH_2)_2CH$(phenyl)$_2$, 3-(4'-sulfamoyl-[1,1'-biphenyl]-4-yl)propyl, 3-phenylpropanoyl, 3-(6-fluoropyridin-3-yl)propyl, 4,4,4-trifluorobutyl, 3-(5-(trifluoromethoxy)benzo[d]thiazol-2-yl)propyl, (Z)-5,5,5-trifluoropent-3-en-1-yl, pent-4-yn-1-yl, butyryl, 3-(6-fluoropyridin-3-yl)propanoyl, cinnamyl, 3-phenylprop-2-yn-1-yl, (E)-3-(6-fluoropyridin-3-yl)allyl, and 3-(6-fluoropyridin-3-yl)prop-2-yn-1-yl.

In specific embodiments of the invention, compounds according to Formula (I) include the compounds described in Table 1.

TABLE 1

| Example | Name | Structure |
|---|---|---|
| 1 | N-(((2R,3R,4R,5R)-3,4-dihydroxy-5-(hydroxymethyl)-1-(3-phenylpropyl)pyrrolidin-2-yl)methyl)acetamide | 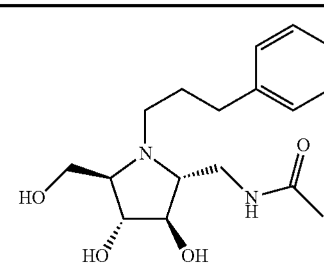 |
| 2 | N-(((2R,3R,4R,5R)-3,4-dihydroxy-5-(hydroxymethyl)-1-(3-(4-methoxyphenyl)propyl)pyrrolidin-2-yl)methyl)acetamide | 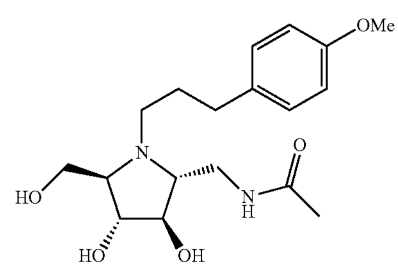 [SMILES: COc1ccc(CCCN2[C@H](CO)[C@@H](O)[C@H](O)[C@H]2CNC(C)=O)cc1] |

TABLE 1-continued

| Example | Name | Structure |
|---|---|---|
| 3 | N-(((2R,3R,4R,5R)-1-(3-([1,1'-biphenyl]-4-yl)propyl)-3,4-dihydroxy-5-(hydroxymethyl)pyrrolidin-2-yl)methyl)acetamide | 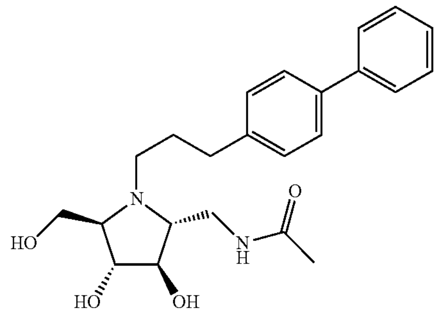 [SMILES: CC(=O)NC[C@@H]1[C@@H](O)[C@H](O)[C@@H](CO)N1CCCc1ccc(-c2ccccc2)cc1] |
| 4 | N-(((2R,3R,4R,5R)-1-(2-([1,1'-biphenyl]-4-yl)ethyl)-3,4-dihydroxy-5-(hydroxymethyl)pyrrolidin-2-yl)methyl)acetamide | 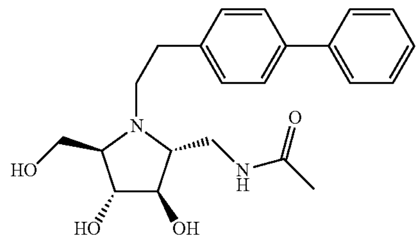 [SMILES: CC(=O)NC[C@@H]1[C@@H](O)[C@H](O)[C@@H](CO)N1CCc1ccc(-c2ccccc2)cc1] |
| 5 | N-(((2R,3R,4R,5R)-3,4-dihydroxy-5-(hydroxymethyl)-1-(4-phenylbutyppyrrolidin-2-yl)methyl)acetamide | 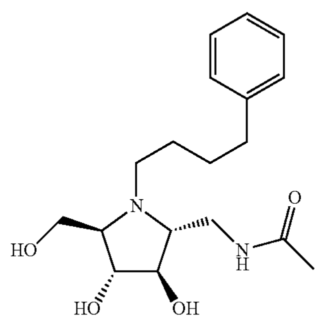 [SMILES: CC(=O)NC[C@@H]1[C@@H](O)[C@H](O)[C@@H](CO)N1CCCCc1ccccc1] |
| 6 | N-(((2R,3R,4R,5R)-1-(3,3-diphenylpropyl)-3,4-dihydroxy-5-(hydroxymethyl)pyrrolidin-2-yl)methyl)acetamide | 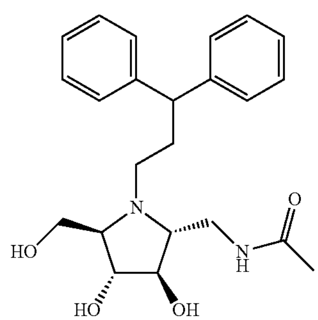 [SMILES: CC(=O)NC[C@@H]1[C@@H](O)[C@H](O)[C@@H](CO)N1CCC(c1ccccc1)c1ccccc1] |
| 7 | N-(((2R,3R,4R,5R)-3,4-dihydroxy-5-(hydroxymethyl)-1-(pyridin-3-ylmethyl)pyrrolidin-2-yl)methyl)acetamide | 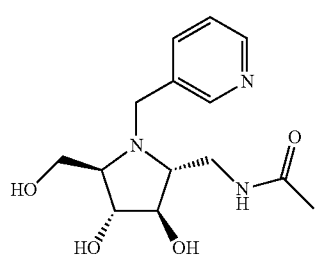 [SMILES: CC(=O)NC[C@@H]1[C@@H](O)[C@H](O)[C@@H](CO)N1Cc1cccnc1] |

TABLE 1-continued

| Example | Name | Structure |
|---|---|---|
| 8 | N-(((2R,3R,4R,5R)-3,4-dihydroxy-5-(hydroxymethyl)-1-(pyridin-2-ylmethyl)pyrrolidin-2-yl)methyl)acetamide | 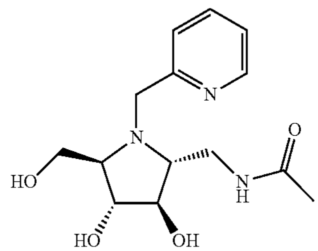 |
| 9 | N-(((2R,3R,4R,5R)-1-([1,1'-biphenyl]-4-ylmethyl)-3,4-dihydroxy-5-(hydroxymethyl)pyrrolidin-2-yl)methyl)acetamide | 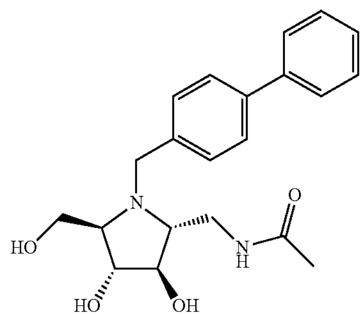 [SMILES: CC(=O)NC[C@@H]1[C@@H](O)[C@H](O)[C@@H](CO)N1Cc1ccc(-c2ccccc2)cc1] |
| 10 | 2-((2R,3R,4R,5R)-3,4-dihydroxy-5-(hydroxymethyl)-1-(3-phenylpropyl)pyrrolidin-2-yl)-N-methylacetamide | 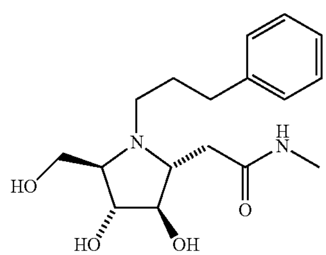 [SMILES: CNC(=O)C[C@@H]1[C@@H](O)[C@H](O)[C@@H](CO)N1CCCc1ccccc1] |
| 11 | 2-((2R,3R,4R,5R)-3,4-dihydroxy-5-(hydroxymethyl)-1-(3-(4-methoxyphenyl)propyl)pyrrolidin-2-yl)-N-ethylacetamide | 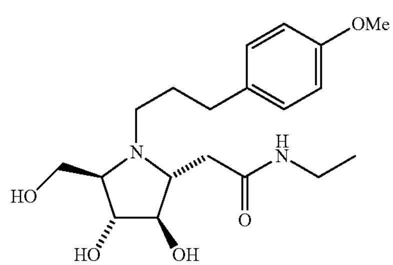 [SMILES: CCNC(=O)C[C@@H]1[C@@H](O)[C@H](O)[C@@H](CO)N1CCCc1ccc(OC)cc1] |
| 12 | 2-((2R,3R,4R,5R)-1-(3,3-diphenylpropyl)-3,4-dihydroxy-5-(hydroxymethyl)pyrrolidin-2-yl)-N-ethylacetamide | 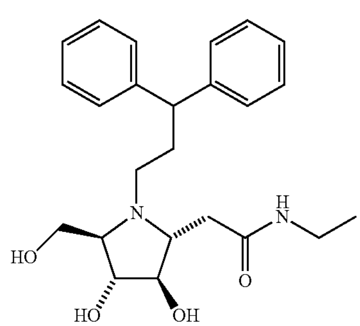 [SMILES: CCNC(=O)C[C@@H]1[C@@H](O)[C@H](O)[C@@H](CO)N1CCC(c1ccccc1)c1ccccc1] |

TABLE 1-continued

| Example | Name | Structure |
|---|---|---|
| 13 | 2-((2R,3S,4R,5R)-3,4-dihydroxy-5-(hydroxymethyl)-1-(3-phenylpropyl)pyrrolidin-2-yl)-N-methylacetamide | 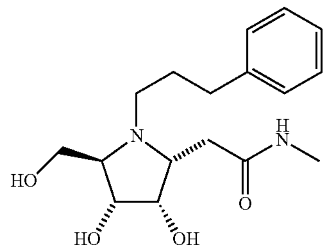 [SMILES: CNC(=O)C[C@@H]1[C@H](O)[C@H](O)[C@@H](CO)N1CCCc1ccccc1] |
| 14 | 2-((2R,3R,4R,5R)-1-(3-([1,1'-biphenyl]-4-yl)propyl)-3,4-dihydroxy-5-(hydroxymethyl)pyrrolidin-2-yl)-N-ethylacetamide | 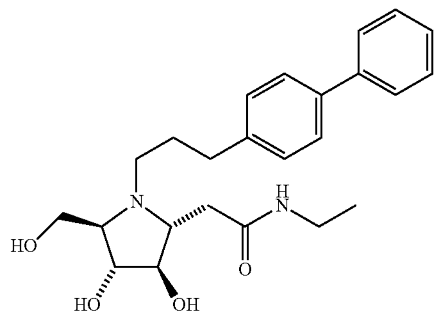 [SMILES: CCNC(=O)C[C@@H]1[C@@H](O)[C@H](O)[C@@H](CO)N1CCCc1ccc(-c2ccccc2)cc1] |
| 15 | 2-((2R,3R,4R,5R)-3,4-dihydroxy-5-(hydroxymethyl)-1-(3-(4'-sulfamoyl-[1,1'-biphenyl]-4-yl)propyl)pyrrolidin-2-yl)-N-methylacetamide | 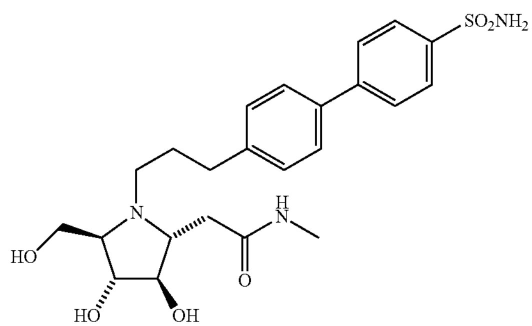 [SMILES: CNC(=O)C[C@@H]1[C@@H](O)[C@H](O)[C@@H](CO)N1CCCc1ccc(-c2ccc(S(N)(=O)=O)cc2)cc1] |
| 16 | 2-((2R,3R,4R,5R)-3,4-dihydroxy-5-(hydroxymethyl)-1-phenethylpyrrolidin-2-yl)-N-ethylacetamide | 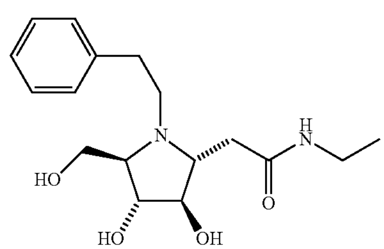 |
| 17 | (2S,3R,4R,5R)-3,4-dihydroxy-5-(hydroxymethyl)-1-phenethyl-N-propylpyrrolidine-2-carboxamide | 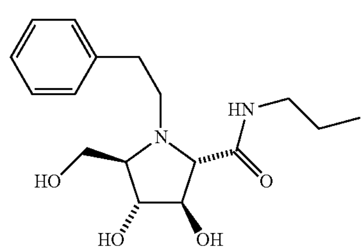 [SMILES: CCCNC(=O)[C@@H]1[C@@H](O)[C@H](O)[C@@H](CO)N1CCc1ccccc1] |

TABLE 1-continued

| Example | Name | Structure |
|---|---|---|
| 18 | N-(((2R,3R,4R,5R)-3,4-dihydroxy-5-(hydroxymethyl)-1-phenethylpyrrolidin-2-yl)methyl)propionamide | 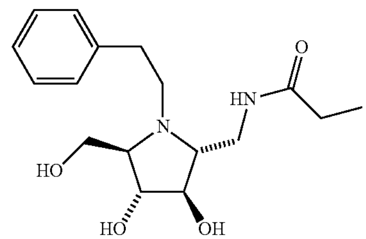 [SMILES: CCC(=O)NC[C@@H]1[C@@H](O)[C@H](O)[C@@H](CO)N1CCc1ccccc1] |
| 19 | N-ethyl-2-((2R,3R,4R,5S)-5-(fluoromethyl)-3,4-dihydroxy-1-phenethylpyrrolidin-2-yl)acetamide | 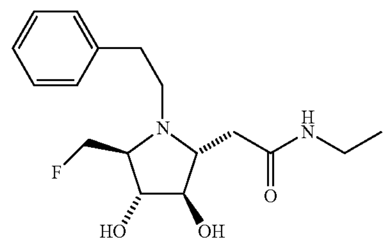 [SMILES: CCNC(=O)C[C@@H]1[C@@H](O)[C@H](O)[C@@H](CF)N1CCc1ccccc1] |
| 20 | N-ethyl-2-((2R,3R,4R,5R)-3-fluoro-4-hydroxy-5-(hydroxymethyl)-1-phenethylpyrrolidin-2-yl)acetamide | 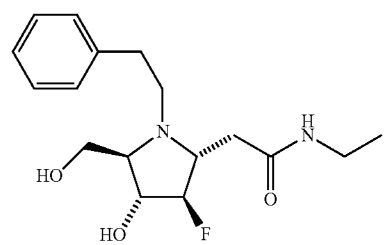 [SMILES: CCNC(=O)C[C@@H]1[C@@H](F)[C@H](O)[C@@H](CO)N1CCc1ccccc1] |
| 21 | N-ethyl-2-((2R,3S,4R,5R)-3-fluoro-4-hydroxy-5-(hydroxymethyl)-1-phenethylpyrrolidin-2-yl)acetamide | 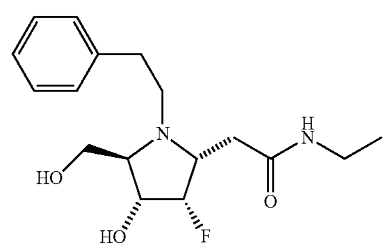 [SMILES: CCNC(=O)C[C@@H]1[C@H](F)[C@H](O)[C@@H](CO)N1CCc1ccccc1] |
| 22 | 2-((2R,3R,4R,5S)-5-(difluoromethyl)-3,4-dihydroxy-1-phenethylpyrrolidin-2-yl)-N-ethylacetamide | 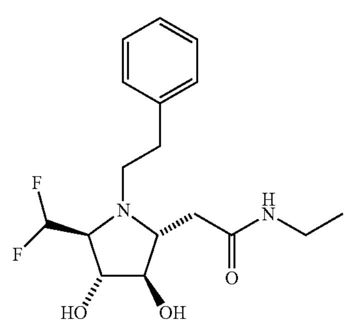 [SMILES: CCNC(=O)C[C@@H]1[C@@H](O)[C@H](O)[C@@H](C(F)F)N1CCc1ccccc1] |
| 23 | 2-((2R,3R,4R,5R)-3-fluoro-4-hydroxy-5-(hydroxymethyl)-1-(3-phenylpropyl)pyrrolidin-2-yl)-N-methylacetamide | 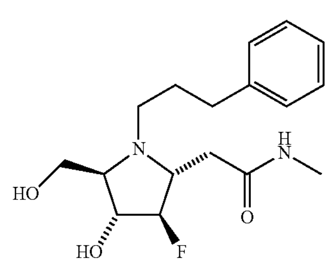 [SMILES: CNC(=O)C[C@@H]1[C@@H](F)[C@H](O)[C@@H](CO)N1CCCc1ccccc1] |

TABLE 1-continued

| Example | Name | Structure |
|---|---|---|
| 24 | 2-((2R,3R,4R,5R)-4-fluoro-3-hydroxy-5-(hydroxymethyl)-1-(3-phenylpropyl)pyrrolidin-2-yl)-N-methylacetamide | 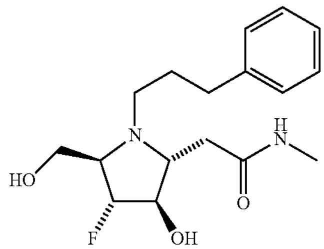 [SMILES: CNC(=O)C[C@@H]1[C@@H](O)[C@H](F)[C@@H](CO)N1CCCc1ccccc1] |
| 25 | 2-((2R,3S,4R,5R)-3-fluoro-4-hydroxy-5-(hydroxymethyl)-1-(3-phenylpropyl)pyrrolidin-2-yl)-N-methylacetamide | 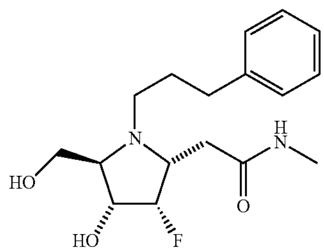 [SMILES: CNC(=O)C[C@@H]1[C@H](F)[C@H](O)[C@@H](CO)N1CCCc1ccccc1] |
| 26 | 2-((2R,3R,4S,5R)-4-fluoro-3-hydroxy-5-(hydroxymethyl)-1-(3-phenylpropyl)pyrrolidin-2-yl)-N-methylacetamide | 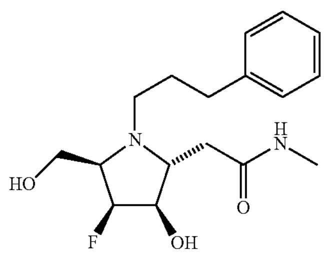 [SMILES: CNC(=O)C[C@@H]1[C@@H](O)[C@@H](F)[C@@H](CO)N1CCCc1ccccc1] |
| 27 | 2-((2R,3R,4R,5S)-5-(fluoromethyl)-3,4-dihydroxy-1-(3-phenylpropyl)pyrrolidin-2-yl)-N-methylacetamide | 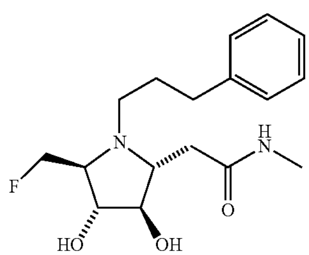 [SMILES: CNC(=O)C[C@@H]1[C@@H](O)[C@H](O)[C@@H](CF)N1CCCc1ccccc1] |
| 28 | 2-((2R,3R,4R,5S)-5-(difluoromethyl)-3,4-dihydroxy-1-(3-phenylpropyl)pyrrolidin-2-yl)-N-methylacetamide | 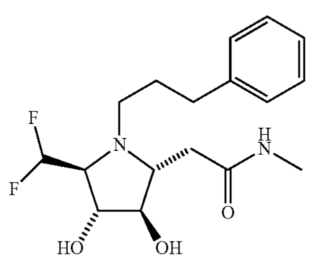 [SMILES: CNC(=O)C[C@@H]1[C@@H](O)[C@H](O)[C@@H](C(F)F)N1CCCc1ccccc1] |
| 29 | 2-((2R,3R,4R,5R)-3,4-dihydroxy-5-methyl-1-(3-phenylpropyl)pyrrolidin-2-yl)-N-methylacetamide | 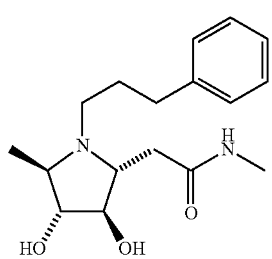 [SMILES: CNC(=O)C[C@@H]1[C@@H](O)[C@H](O)[C@@H](C)N1CCCc1ccccc1] |

TABLE 1-continued

| Example | Name | Structure |
|---|---|---|
| 30 | 2-((2S,4S,5R)-4-hydroxy-5-(hydroxymethyl)-1-(3-phenylpropyl)pyrrolidin-2-yl)-N-methylacetamide | 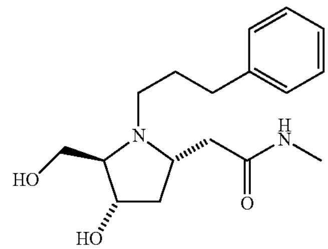 [SMILES: CNC(=O)C[C@@H]1C[C@H](O)[C@@H](CO)N1CCCc1ccccc1] |
| 31 | 2-((2R,3S,5S)-3-hydroxy-5-(hydroxymethyl)-1-(3-phenylpropyl)pyrrolidin-2-yl)-N-methylacetamide | 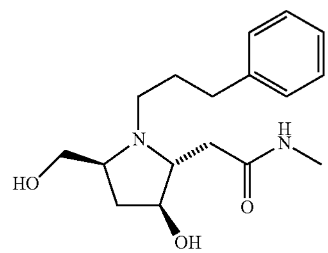 [SMILES: CNC(=O)C[C@@H]1[C@@H](O)C[C@@H](CO)N1CCCc1ccccc1] |
| 32 | 2-((2R,3R,4R)-3,4-dihydroxy-1-(3-phenylpropyl)pyrrolidin-2-yl)-N-methylacetamide | 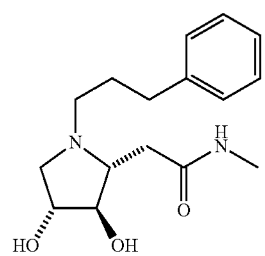 [SMILES: CNC(=O)C[C@@H]1[C@@H](O)[C@H](O)CN1CCCc1ccccc1] |
| 33 | 2-((2R,3R,4R,5S)-3-fluoro-5-(fluoromethyl)-4-hydroxy-1-(3-phenylpropyl)pyrrolidin-2-yl)-N-methylacetamide | 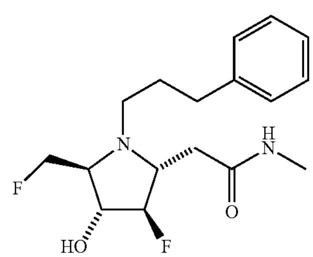 [SMILES: CNC(=O)C[C@@H]1[C@@H](F)[C@H](O)[C@@H](CF)N1CCCc1ccccc1] |
| 34 | 2-((2R,3S,4R,5S)-5-(difluoromethyl)-3-fluoro-4-hydroxy-1-(3-phenylpropyl)pyrrolidin-2-yl)-N-methylacetamide | 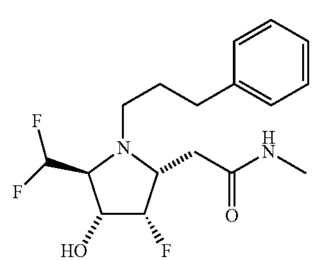 [SMILES: CNC(=O)C[C@@H]1[C@H](F)[C@H](O)[C@@H](C(F)F)N1CCCc1ccccc1] |
| 35 | N-(((2R,3R,4R,5R)-3-fluoro-4-hydroxy-5-(hydroxymethyl)-1-(3-phenylpropyl)pyrrolidin-2-yl)methyl)propionamide | 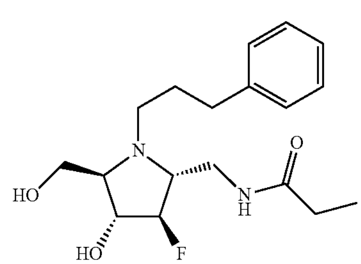 [SMILES: CCC(=O)NC[C@@H]1[C@@H](F)[C@H](O)[C@@H](CO)N1CCCc1ccccc1] |

TABLE 1-continued

| Example | Name | Structure |
|---|---|---|
| 36 | N-(((2R,3R,4R,5R)-4-fluoro-3-hydroxy-5-(hydroxymethyl)-1-(3-phenylpropyl)pyrrolidin-2-yl)methyl)propionamide | 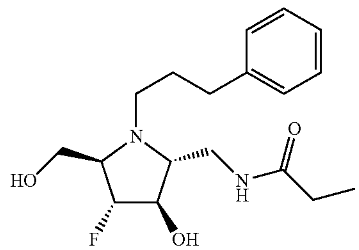 [SMILES: CCC(=O)NC[C@@H]1[C@@H](O)[C@H](F)[C@@H](CO)N1CCCc1ccccc1] |
| 37 | N-(((2R,3S,4R,5R)-3-fluoro-4-hydroxy-5-(hydroxymethyl)-1-(3-phenylpropyl)pyrrolidin-2-yl)methyl)propionamide | 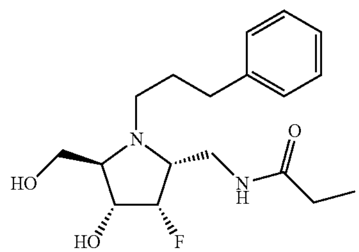 [SMILES: CCC(=O)NC[C@@H]1[C@H](F)[C@H](O)[C@@H](CO)N1CCCc1ccccc1] |
| 38 | N-(((2R,3R,4S,5R)-4-fluoro-3-hydroxy-5-(hydroxymethyl)-1-(3-phenylpropyl)pyrrolidin-2-yl)methyl)propionamide | 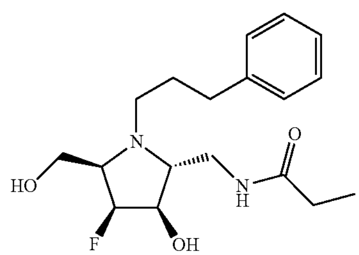 [SMILES: CCC(=O)NC[C@@H]1[C@@H](O)[C@@H](F)[C@@H](CO)N1CCCc1ccccc1] |
| 39 | N-(((2R,3R,4R,5S)-5-(fluoromethyl)-3,4-dihydroxy-1-(3-phenylpropyl)pyrrolidin-2-yl)methyl)propionamide | 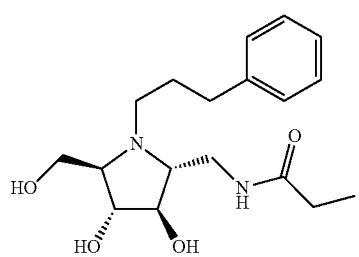 [SMILES: CCC(=O)NC[C@@H]1[C@@H](O)[C@H](O)[C@@H](CO)N1CCCc1ccccc1] |
| 40 | N-(((2R,3R,4R,5S)-5-(difluoromethyl)-3,4-dihydroxy-1-(3-phenylpropyl)pyrrolidin-2-yl)methyl)propionamide | 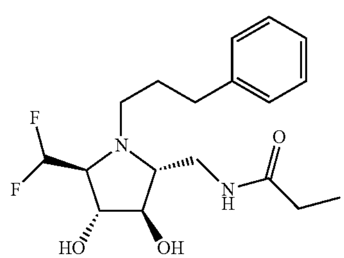 [SMILES: CCC(=O)NC[C@@H]1[C@@H](O)[C@H](O)[C@@H](C(F)F)N1CCCc1ccccc1] |
| 41 | N-(((2S,4S,5R)-4-hydroxy-5-(hydroxymethyl)-1-(3-phenylpropyl)pyrrolidin-2-yl)methyl)propionamide | 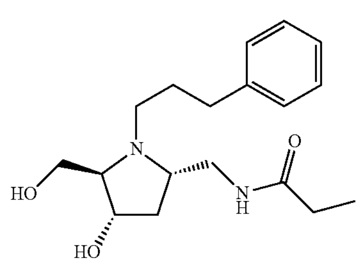 [SMILES: CCC(=O)NC[C@@H]1C[C@H](O)[C@@H](CO)N1CCCc1ccccc1] |

TABLE 1-continued

| Example | Name | Structure |
|---|---|---|
| 42 | N-(((2R,3S,5S)-3-hydroxy-5-(hydroxymethyl)-1-(3-phenylpropyl)pyrrolidin-2-yl)methyl)propionamide | 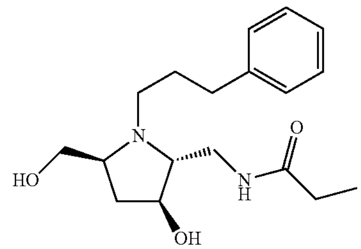 [SMILES: CCC(=O)NC[C@@H]1[C@@H](O)C[C@@H](CO)N1CCCc1ccccc1] |
| 43 | N-(((2R,3R,4R,5R)-3,4-dihydroxy-5-methyl-1-(3-phenylpropyl)pyrrolidin-2-yl)methyl)propionamide | 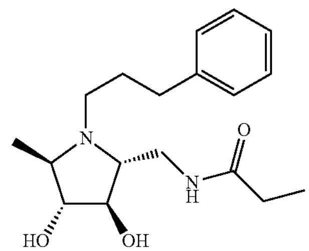 [SMILES: CCC(=O)NC[C@@H]1[C@@H](O)[C@H](O)[C@@H](C)N1CCCc1ccccc1] |
| 44 | N-(((2R,3R,4R)-3,4-dihydroxy-1-(3-phenylpropyl)pyrrolidin-2-yl)methyl)propionamide | 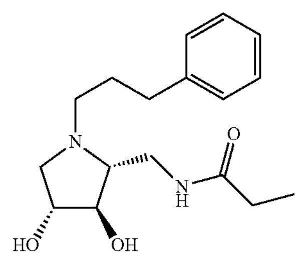 [SMILES: CCC(=O)NC[C@@H]1[C@@H](O)[C@H](O)CN1CCCc1ccccc1] |
| 45 | N-(((2R,3R,4R,5S)-3-fluoro-5-(fluoromethyl)-4-hydroxy-1-(3-phenylpropyl)pyrrolidin-2-yl)methyl)propionamide | 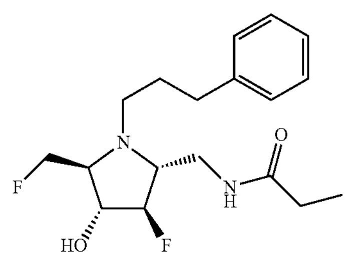 [SMILES: CCC(=O)NC[C@@H]1[C@@H](F)[C@H](O)[C@@H](CF)N1CCCc1ccccc1] |
| 46 | N-(((2R,3S,4R,5S)-5-(difluoromethyl)-3-fluoro-4-hydroxy-1-(3-phenylpropyl)pyrrolidin-2-yl)methyl)propionamide | 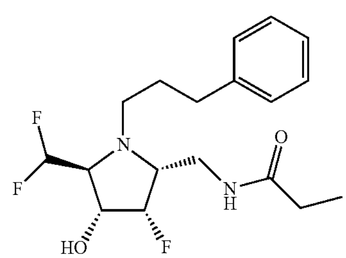 [SMILES: CCC(=O)NC[C@@H]1[C@H](F)[C@H](O)[C@@H](C(F)F)N1CCCc1ccccc1] |
| 47 | N-(((2R,3R,4R,5R)-3,4-dihydroxy-5-(hydroxymethyl)-1-(3-phenylpropanoyl)pyrrolidin-2-yl)methyl)propionamide | 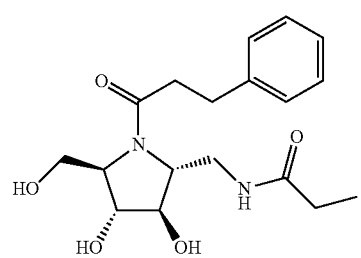 [SMILES: CCC(=O)NC[C@@H]1[C@@H](O)[C@H](O)[C@@H](CO)N1C(=O)CCc1ccccc1] |

TABLE 1-continued

| Example | Name | Structure |
|---|---|---|
| 48 | N-(((2R,3R,4R,5R)-1-(3-(6-fluoropyridin-3-yl)propyl)-3,4-dihydroxy-5-(hydroxymethyl)pyrrolidin-2-yl)methyl)propionamide | 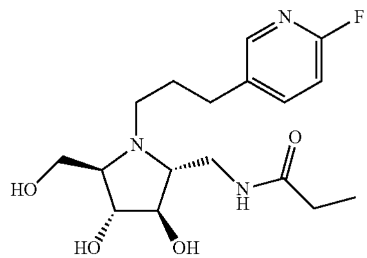 [SMILES: CCC(=O)NC[C@@H]1[C@@H](O)[C@H](O)[C@@H](CO)N1CCCc1ccc(F)nc1] |
| 49 | N-(((2R,3R,4R,5R)-3,4-dihydroxy-5-(hydroxymethyl)-1-(4,4,4-trifluorobutyl)pyrrolidin-2-yl)methyl)propionamide | 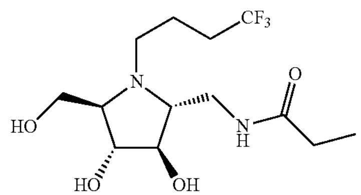 [SMILES: CCC(=O)NC[C@@H]1[C@@H](O)[C@H](O)[C@@H](CO)N1CCCC(F)(F)F] |
| 50 | N-(((2R,3R,4R,5R)-3,4-dihydroxy-5-(hydroxymethyl)-1-(3-(5-(trifluoromethoxy)benzo[d]thiazol-2-yl)propyl)pyrrolidin-2-yl)methyl)propionamide | 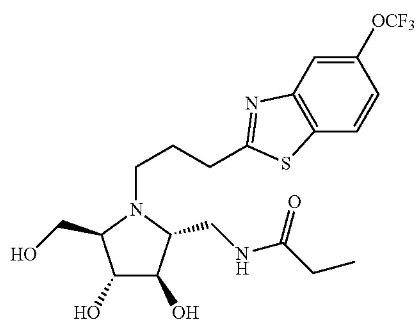 [SMILES: CCC(=O)NC[C@@H]1[C@@H](O)[C@H](O)[C@@H](CO)N1CCCc1nc2cc(OC(F)(F)F)ccc2s1] |
| 51 | 2-((2R,3R,4R,5R)-3,4-dihydroxy-5-(hydroxymethyl)-1-((Z)-5,5,5-trifluoropent-3-en-1-yl)pyrrolidin-2-yl)-N-methylacetamide | 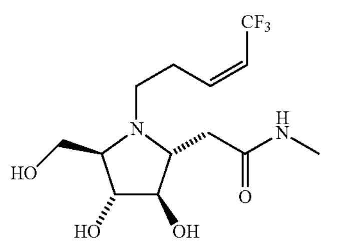 [SMILES: CNC(=O)C[C@@H]1[C@@H](O)[C@H](O)[C@@H](CO)N1CC/C=C\C(F)(F)F] |
| 52 | 2-((2R,3R,4R,5R)-3,4-dihydroxy-5-(hydroxymethyl)-1-(pent-4-yn-1-yl)pyrrolidin-2-yl)-N-methylacetamide | 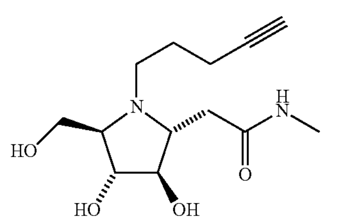 |
| 53 | 2-((2R,3R,4R,5R)-1-butyryl-3,4-dihydroxy-5-(hydroxymethyl)pyrrolidin-2-yl)-N-methylacetamide | 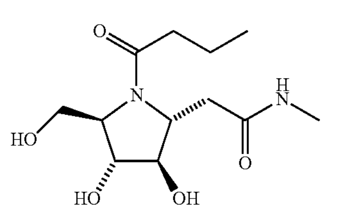 |

TABLE 1-continued

| Example | Name | Structure |
|---|---|---|
| 54 | 2-((2R,3R,4R,5R)-1-(3-(6-fluoropyridin-3-yl)propanoyl)-3,4-dihydroxy-5-(hydroxymethyl)pyrrolidin-2-yl)-N-methylacetamide | 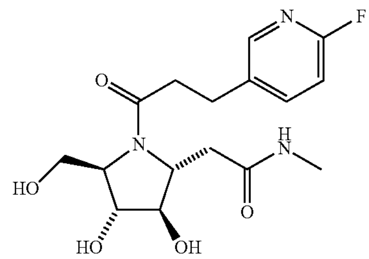 [SMILES: CNC(=O)C[C@@H]1[C@@H](O)[C@H](O)[C@@H](CO)N1C(=O)CCc1ccc(F)nc1] |
| 55 | 2-((2R,3R,4R,5R)-1-cinnamyl-3,4-dihydroxy-5-(hydroxymethyl)pyrrolidin-2-yl)-N-methylacetamide | 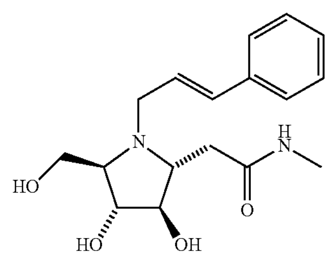 |
| 56 | 2-((2R,3R,4R,5R)-3,4-dihydroxy-5-(hydroxymethyl)-1-(3-phenylprop-2-yn-1-yl)pyrrolidin-2-yl)-N-methylacetamide | 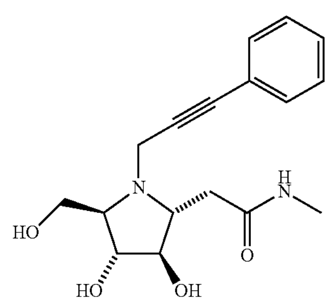 |
| 57 | 2-((2R,3R,4R,5R)-1-((E)-3-(6-fluoropyridin-3-yl)allyl)-3,4-dihydroxy-5-(hydroxymethyl)pyrrolidin-2-yl)-N-methylacetamide | 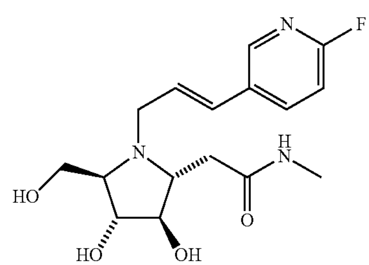 |
| 58 | 2-((2R,3R,4R,5R)-1-(3-(6-fluoropyridin-3-yl)prop-2-yn-1-yl)-3,4-dihydroxy-5-(hydroxymethyl)pyrrolidin-2-yl)-N-methylacetamide | 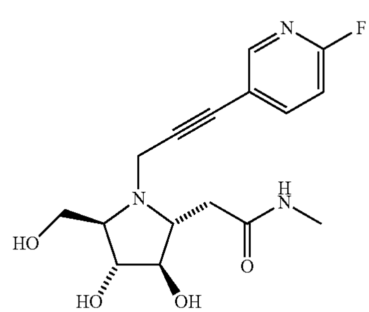 [SMILES: CNC(=O)C[C@@H]1[C@@H](O)[C@H](O)[C@@H](CO)N1CC#Cc1ccc(F)nc1] |

In alternative embodiments of the invention, compounds according to Formula (I) include one or more of the compounds described in Table 2.

In alternative embodiments of the invention, one or more of the compounds described in Table 2 are specifically excluded from the compounds described in Formula (I).

TABLE 2

| Name | Structure |
|---|---|
| N-(((2R,3R,4R,5R)-3,4-dihydroxy-5-(hydroxymethyl)pyrrolidin-2-yl)methyl)acetamide | 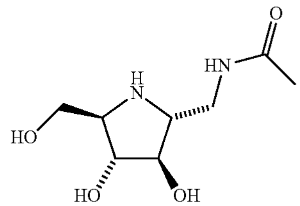 |
| N-(((2R,3R,4R,5R)-3,4-dihydroxy-5-(hydroxymethyl)pyrrolidin-2-yl)methyl)propionamide | 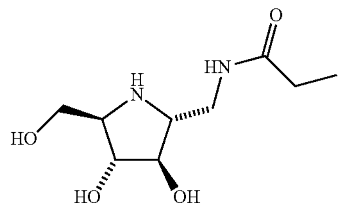 |
| N-(((2R,3R,4R,5R)-3,4-dihydroxy-5-(hydroxymethyl)pyrrolidin-2-yl)methyl)butyramide | 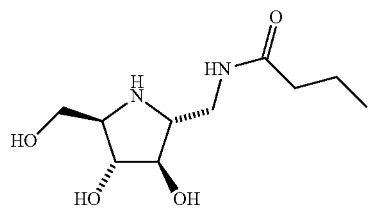 [SMILES: CCCC(=O)NC[C@H]1N[C@H](CO)[C@@H](O)[C@@H]1O] |
| N-(((2R,3R,4R,5R)-3,4-dihydroxy-5-(hydroxymethyl)pyrrolidin-2-yl)methyl)pentanamide | 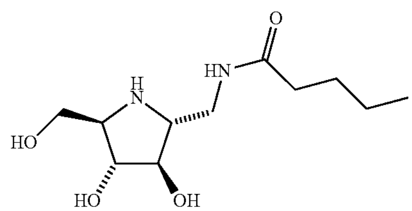 [SMILES: CCCCC(=O)NC[C@H]1N[C@H](CO)[C@@H](O)[C@@H]1O] |
| N-(((2R,3R,4R,5R)-3,4-dihydroxy-5-(hydroxymethyl)pyrrolidin-2-yl)methyl)hexanamide | 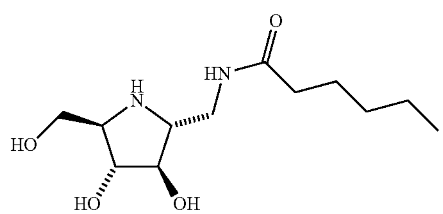 [SMILES: CCCCCC(=O)NC[C@H]1N[C@H](CO)[C@@H](O)[C@@H]1O] |
| N-(((2R,3R,4R,5R)-3,4-dihydroxy-5-(hydroxymethyl)-1-methylpyrrolidin-2-yl)methyl)acetamide | 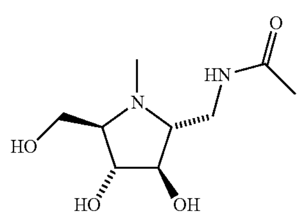 |
| N-(((2R,3R,4R,5R)-1-butyl-3,4-dihydroxy-5-(hydroxymethyl)pyrrolidin-2-yl)methyl)acetamide | 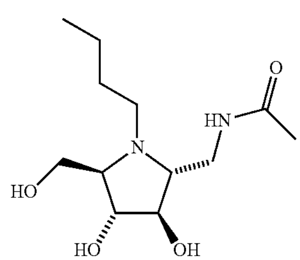 [SMILES: CCCCN1[C@H](CO)[C@@H](O)[C@H](O)[C@H]1CNC(C)=O] |

TABLE 2-continued

| Name | Structure |
| --- | --- |
| N-(((2R,3R,4R,5R)-1-hexyl-3,4-dihydroxy-5-(hydroxymethyl)pyrrolidin-2-yl)methyl)acetamide | 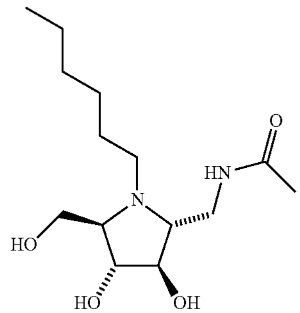 [SMILES: CCCCCCN1[C@H](CO)[C@@H](O)[C@H](O)[C@H]1CNC(C)=O] |
| N-(((2R,3R,4R,5R)-1-heptyl-3,4-dihydroxy-5-(hydroxymethyl)pyrrolidin-2-yl)methyl)acetamide | 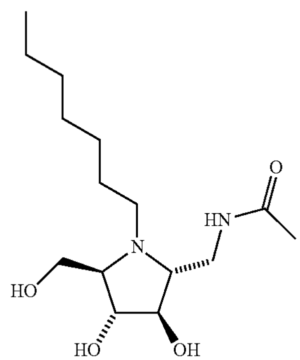 [SMILES: CCCCCCCN1[C@H](CO)[C@@H](O)[C@H](O)[C@H]1CNC(C)=O] |
| N-(((2R,3R,4R,5R)-3,4-dihydroxy-5-(hydroxymethyl)-1-octylpyrrolidin-2-yl)methyl)acetamide | 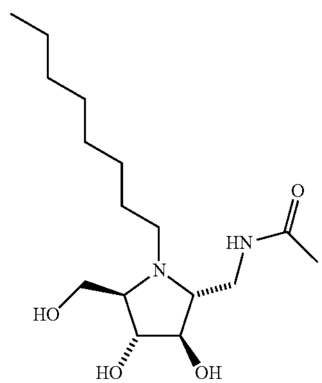 [SMILES: CCCCCCCCN1[C@H](CO)[C@@H](O)[C@H](O)[C@H]1CNC(C)=O] |
| N-(((2R,3R,4R,5R)-3,4-dihydroxy-5-(hydroxymethyl)-1-nonylpyrrolidin-2-yl)methyl)acetamide | 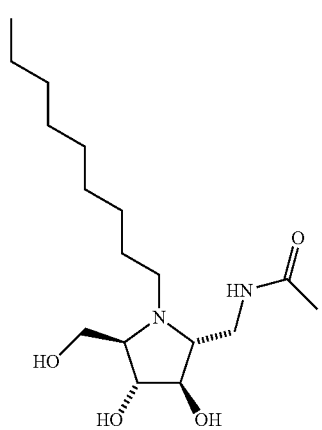 [SMILES: CCCCCCCCCN1[C@H](CO)[C@@H](O)[C@H](O)[C@H]1CNC(C)=O] |

TABLE 2-continued

| Name | Structure |
| --- | --- |
| N-(((2R,3S,4R,5R)-3,4-dihydroxy-5-(hydroxymethyl)-1-nonylpyrrolidin-2-yl)methyl)acetamide | 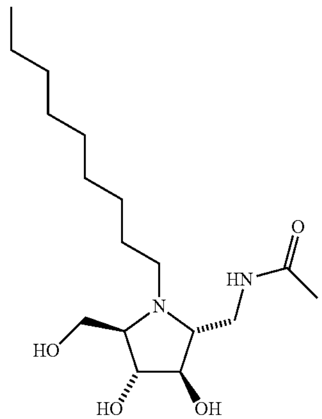 [SMILES: CCCCCCCCCN1[C@H](CO)[C@@H](O)[C@H](O)[C@H]1CNC(C)=O] |
| N-(((2R,3R,4R,5R)-3,4-dihydroxy-5-methylpyrrolidin-2-yl)methyl)acetamide | 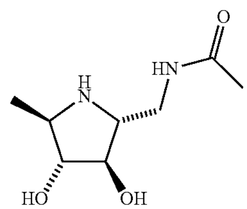 |
| N-(((2R,3R,4R,5R)-3,4-dihydroxy-5-(hydroxymethyl)pyrrolidin-2-yl)methyl)isobutyramide | 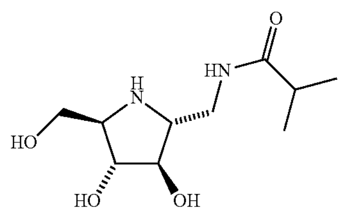 [SMILES: CC(C)C(=O)NC[C@H]1N[C@H](CO)[C@@H](O)[C@@H]1O] |
| N-(((2R,3R,4R,5R)-3,4-dihydroxy-5-(hydroxymethyl)pyrrolidin-2-yl)methyl)-3-methylbutanamide | 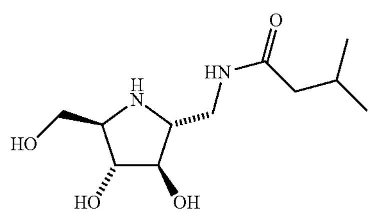 [SMILES: CC(C)CC(=O)NC[C@H]1N[C@H](CO)[C@@H](O)[C@@H]1O] |
| N-(((2R,3R,4R,5R)-1-ethyl-3,4-dihydroxy-5-(hydroxymethyl)pyrrolidin-2-yl)methyl)acetamide | 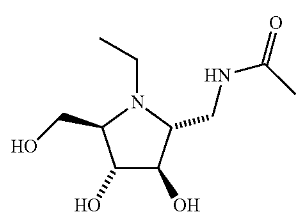 [SMILES: CCN1[C@H](CO)[C@@H](O)[C@H](O)[C@H]1CNC(C)=O] |
| N-(((2R,3R,4R,5R)-3,4-dihydroxy-5-(hydroxymethyl)-1-propylpyrrolidin-2-yl)methyl)acetamide | 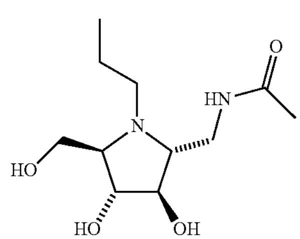 |

TABLE 2-continued

| Name | Structure |
|---|---|
| N-(((2R,3R,4R,5R)-3,4-dihydroxy-5-(hydroxymethyl)-1-isopropylpyrrolidin-2-yl)methyl)acetamide | 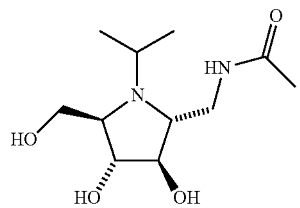 [SMILES: CC(=O)NC[C@@H]1[C@@H](O)[C@H](O)[C@@H](CO)N1C(C)C] |
| N-(((2R,3R,4R,5R)-1-benzyl-3,4-dihydroxy-5-(hydroxymethyl)pyrrolidin-2-yl)methyl)acetamide | 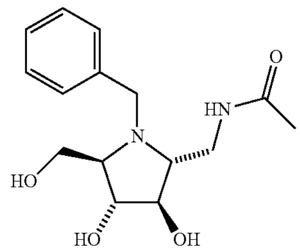 [SMILES: CC(=O)NC[C@@H]1[C@@H](O)[C@H](O)[C@@H](CO)N1Cc1ccccc1] |
| N-(((2R,3R,4R,5R)-3,4-dihydroxy-1-(4-hydroxybenzyl)-5-(hydroxymethyl)pyrrolidin-2-yl)methyl)acetamide | 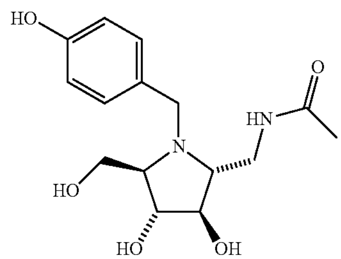 [SMILES: CC(=O)NC[C@@H]1[C@@H](O)[C@H](O)[C@@H](CO)N1Cc1ccc(O)cc1] |
| N-(((2R,3R,4R,5R)-3,4-dihydroxy-5-(hydroxymethyl)-1-(4-(pyridin-2-yl)benzyl)pyrrolidin-2-yl)methyl)acetamide | 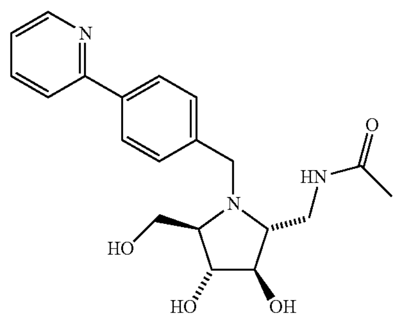 [SMILES: CC(=O)NC[C@@H]1[C@@H](O)[C@H](O)[C@@H](CO)N1Cc1ccc(-c2ccccn2)cc1] |
| N-(((2R,3R,4R,5R)-3,4-dihydroxy-5-(hydroxymethyl)-1-phenethylpyrrolidin-2-yl)methyl)acetamide | 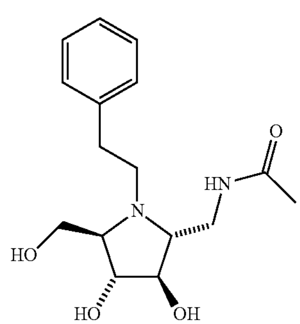 |
| N-(((2R,3R,4R,5R)-3,4-dihydroxy-5-(hydroxymethyl)-1-methylpyrrolidin-2-yl)methyl)propionamide | 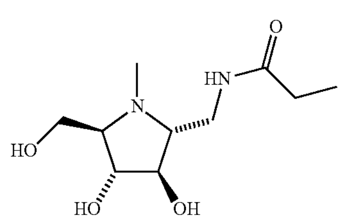 [SMILES: CCC(=O)NC[C@@H]1[C@@H](O)[C@H](O)[C@@H](CO)N1C] |

TABLE 2-continued

| Name | Structure |
|---|---|
| N-(((2R,3R,4R,5R)-3,4-dihydroxy-5-(hydroxymethyl)pyrrolidin-2-yl)methyl)-N-methylacetamide | 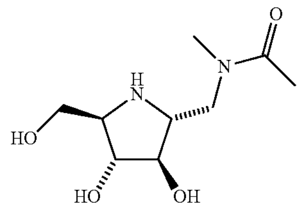 |
| N-(((2R,3R,4R,5R)-3,4-dihydroxy-5-(hydroxymethyl)-1-methylpyrrolidin-2-yl)methyl)-N-methylacetamide | 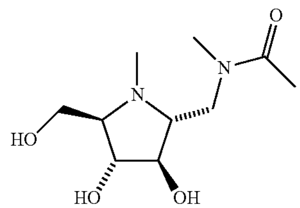 [SMILES: CC(=O)N(C)C[C@@H]1[C@@H](O)[C@H](O)[C@@H](CO)N1C] |
| N-(((2R,3R,4R,5R)-1-acetyl-3,4-dihydroxy-5-(hydroxymethyl)pyrrolidin-2-yl)methyl)acetamide | 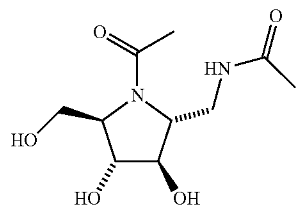 [SMILES: CC(=O)NC[C@@H]1[C@@H](O)[C@H](O)[C@@H](CO)N1C(C)=O] |
| N-(((2R,3R,4S,5R)-3,4-dihydroxy-5-(hydroxymethyl)pyrrolidin-2-yl)methyl)acetamide | 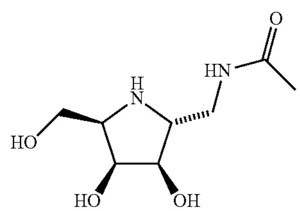 |
| N-(((2R,3S,4R,5R)-3,4-dihydroxy-5-(hydroxymethyl)pyrrolidin-2-yl)methyl)acetamide | 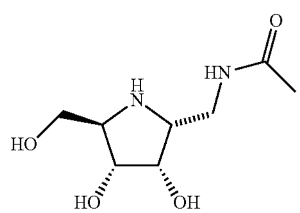 |
| N-(((2R,3R,4R,5R)-3,4-dihydroxy-5-methylpyrrolidin-2-yl)methyl)acetamide | 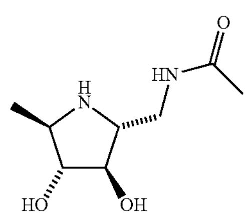 |
| N-(((2R,3R,4S)-3,4-dihydroxypyrrolidin-2-yl)methyl)acetamide | 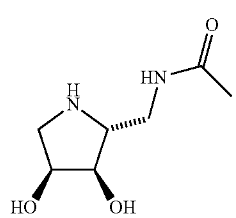 |

TABLE 2-continued

| Name | Structure |
|---|---|
| N-(((2R,3S,4S)-3,4-dihydroxypyrrolidin-2-yl)methyl)acetamide | 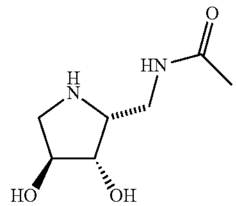 |
| N-(((2R,3R,4S)-3,4-dihydroxy-1-methylpyrrolidin-2-yl)methyl)acetamide | 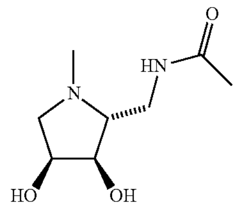 |
| N-(((2R,3S,4S)-3,4-dihydroxypyrrolidin-2-yl)methyl)pivalamide | 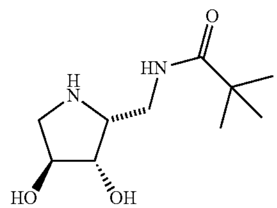 |
| N-(((2R,3R,4S)-3,4-dihydroxy-1-(2-hydroxyethyl)pyrrolidin-2-yl)methyl)acetamide | 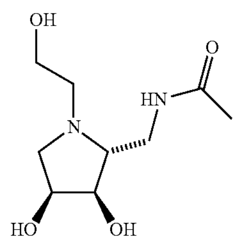 |
| N-(((2R,3S,4S)-3,4-dihydroxypyrrolidin-2-yl)methyl)hexanamide | 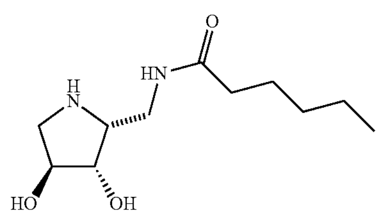 [SMILES: CCCCCC(=O)NC[C@H]1NC[C@H](O)[C@H]1O] |
| N-(((2R,3R,4S)-1-butyl-3,4-dihydroxypyrrolidin-2-yl)methyl)acetamide | 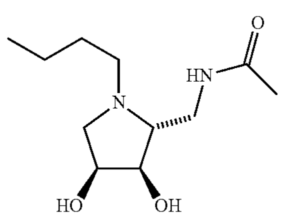 [SMILES: CCCCN1C[C@H](O)[C@H](O)[C@H]1CNC(C)=O] |
| N-(((2R,3R,4S)-1-butyl-3,4-dihydroxypyrrolidin-2-yl)methyl)butyramide | 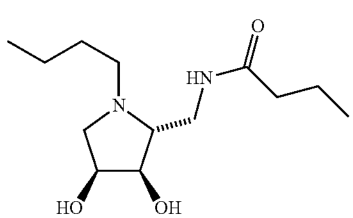 [SMILES: CCCCN1C[C@H](O)[C@H](O)[C@H]1CNC(=O)CCC] |

TABLE 2-continued

| Name | Structure |
|------|-----------|
| N-(((2R,3R,4S)-1-benzyl-3,4-dihydroxypyrrolidin-2-yl)methyl)acetamide | 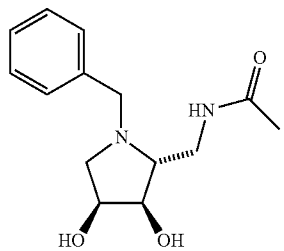 [SMILES: CC(=O)NC[C@@H]1[C@@H](O)[C@@H](O)CN1Cc1ccccc1] |
| N-(((2R,3R,4S)-3,4-dihydroxy-1-nonylpyrrolidin-2-yl)methyl)acetamide | 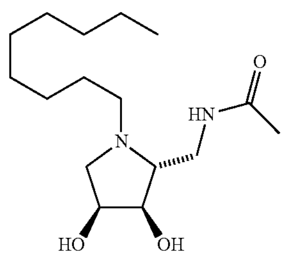 [SMILES: CCCCCCCCCN1C[C@H](O)[C@H](O)[C@H]1CNC(C)=O] |
| N-(((2R,3R,4S)-3,4-dihydroxy-1-(9-hydroxynonyl)pyrrolidin-2-yl)methyl)acetamide | 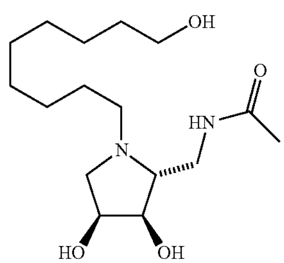 [SMILES: CC(=O)NC[C@@H]1[C@@H](O)[C@@H](O)CN1CCCCCCCCCO] |
| N-(((2R,3R,4S)-1-benzyl-3,4-dihydroxypyrrolidin-2-yl)methyl)butyramide | 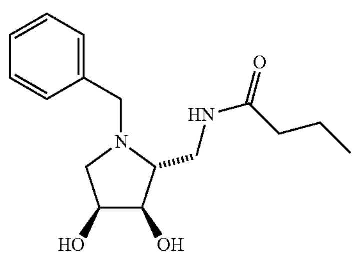 [SMILES: CCCC(=O)NC[C@@H]1[C@@H](O)[C@@H](O)CN1Cc1ccccc1] |
| N-(((2R,3R,4S)-1-([1,1'-biphenyl]-4-ylmethyl)-3,4-dihydroxypyrrolidin-2-yl)methyl)acetamide | 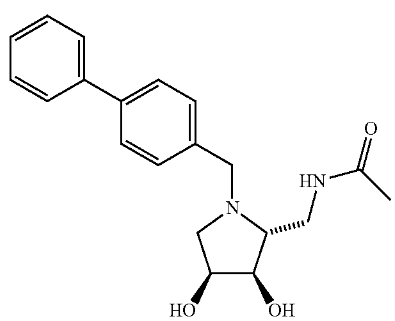 [SMILES: CC(=O)NC[C@@H]1[C@@H](O)[C@@H](O)CN1Cc1ccc(-c2ccccc2)cc1] |
| (2S,3S,4S)-3,4-dihydroxypyrrolidine-2-carboxamide | 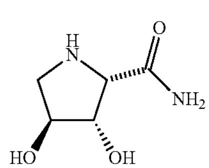 |

TABLE 2-continued

| Name | Structure |
|---|---|
| (2S,3R,4R)-3,4-dihydroxypyrrolidine-2-carboxamide | 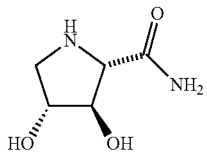 |
| (2S)-3,4-dihydroxy-N,N-dimethylpyrrolidine-2-carboxamide | 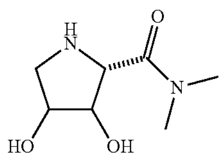 |
| (2S,3R,4R)-N-(tert-butyl)-3,4-dihydroxypyrrolidine-2-carboxamide | 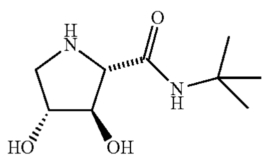 |
| N-butyl-2-((2R,3S,4R,5R)-3,4-dihydroxy-5-(hydroxymethyl)pyrrolidin-2-yl)acetamide | 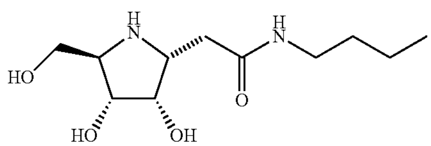 [SMILES: CCCCNC(=O)C[C@H]1N[C@H](CO)[C@@H](O)[C@H]1O] |
| N-butyl-2-((2R,3S,4R,5R)-3,4-dihydroxy-1-(2-hydroxyethyl)-5-(hydroxymethyl)pyrrolidin-2-yl)acetamide | 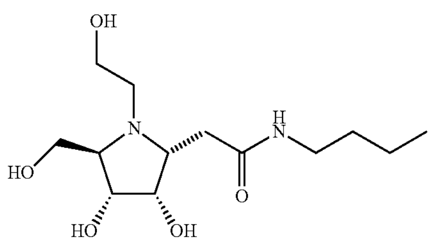 [SMILES: CCCCNC(=O)C[C@@H]1[C@H](O)[C@H](O)[C@@H](CO)N1CCO] |
| N-butyl-2-((2R,3S,4R,5R)-1-butyl-3,4-dihydroxy-5-(hydroxymethyl)pyrrolidin-2-yl)acetamide | 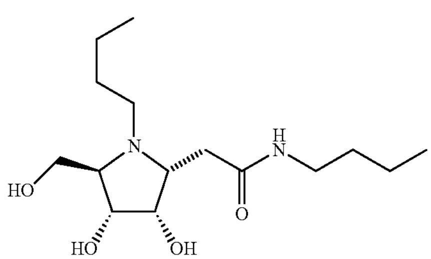 [SMILES: CCCCNC(=O)C[C@@H]1[C@H](O)[C@H](O)[C@@H](CO)N1CCCC] |
| N-butyl-2-((2R,3S,4R,5R)-3,4-dihydroxy-5-(hydroxymethyl)-1-(9-hydroxynonyl)pyrrolidin-2-yl)acetamide | 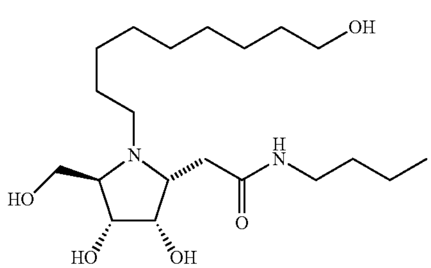 [SMILES: CCCCNC(=O)C[C@@H]1[C@H](O)[C@H](O)[C@@H](CO)N1CCCCCCCCCO] |

TABLE 2-continued

| Name | Structure |
|---|---|
| 2-((2R,3S,4R,5R)-1-benzyl-3,4-dihydroxy-5-(hydroxymethyl)pyrrolidin-2-yl)-N-butylacetamide | 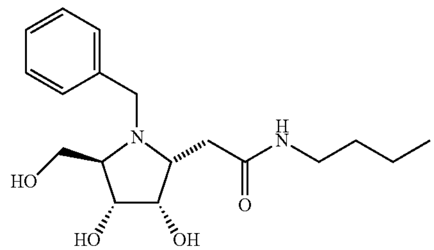 [SMILES: CCCCNC(=O)C[C@@H]1[C@H](O)[C@H](O)[C@@H](CO)N1Cc1ccccc1] |
| 2-((2R,3S,4R,5R)-1-([1,1'-biphenyl]-4-ylmethyl)-3,4-dihydroxy-5-(hydroxymethyl)pyrrolidin-2-yl)-N-butylacetamide | 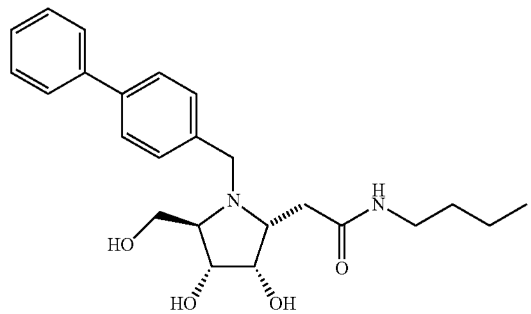 [SMILES: CCCCNC(=O)C[C@@H]1[C@H](O)[C@H](O)[C@@H](CO)N1Cc1ccc(-c2ccccc2)cc1] |
| (2S,3R,4R,5R)-2-(fluoromethyl)-5-(hydroxymethyl)pyrrolidine-3,4-diol | 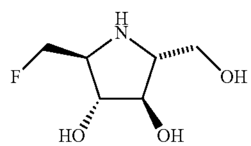 [SMILES: OC[C@H]1N[C@H](CF)[C@@H](O)[C@@H]1O] |
| (2R,3R,4R,5R)-2,5-bis(hydroxymethyl)pyrrolidine-3,4-diol | 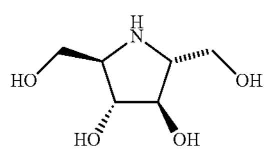 [SMILES: OC[C@H]1N[C@H](CO)[C@@H](O)[C@@H]1O] |
| (2R,3S,4R,5R)-2,5-bis(hydroxymethyl)pyrrolidine-3,4-diol | 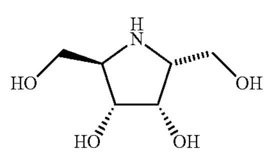 [SMILES: OC[C@H]1N[C@H](CO)[C@@H](O)[C@H]1O] |
| (2R,3S,4S,5R)-2,5-bis(hydroxymethyl)pyrrolidine-3,4-diol | 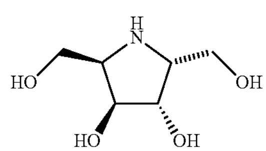 [SMILES: OC[C@H]1N[C@H](CO)[C@H](O)[C@H]1O] |
| (2R,3R,4R,5R)-2,5-bis(hydroxymethyl)-1-methylpyrrolidine-3,4-diol | 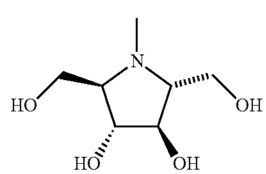 |
| (2R,3R,4S,5R)-2,5-bis(hydroxymethyl)-1-methylpyrrolidine-3,4-diol | 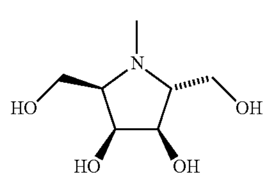 |

TABLE 2-continued

| Name | Structure |
| --- | --- |
| (2R,3R,4R,5R)-1-(2-hydroxyethyl)-2,5-bis(hydroxymethyl)pyrrolidine-3,4-diol | 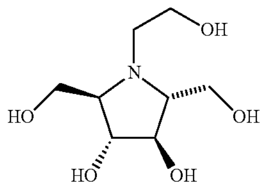 [SMILES: OCCN1[C@H](CO)[C@@H](O)[C@H](O)[C@H]1CO] |
| (2R,3S,4R,5R)-1-(2-hydroxyethyl)-2,5-bis(hydroxymethyl)pyrrolidine-3,4-diol | 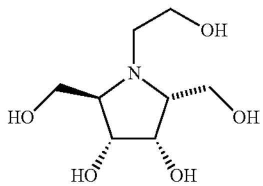 [SMILES: OCCN1[C@H](CO)[C@H](O)[C@H](O)[C@H]1CO] |
| (2R,3R,4R,5R)-2,5-bis(hydroxymethyl)-1-propylpyrrolidine-3,4-diol | 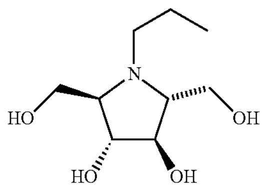 |
| (2R,3R,4R,5R)-1-butyl-2,5-bis(hydroxymethyl)pyrrolidine-3,4-diol | 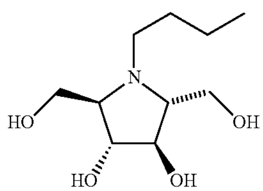 |
| (2R,3R,4R,5R)-2,5-bis(hydroxymethyl)-1-(3-hydroxypropyl)pyrrolidine-3,4-diol | 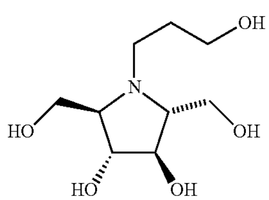 [SMILES: OCCCN1[C@H](CO)[C@@H](O)[C@H](O)[C@H]1CO] |
| (2R,3S,4S,5R)-1-hexyl-2,5-bis(hydroxymethyl)pyrrolidine-3,4-diol | 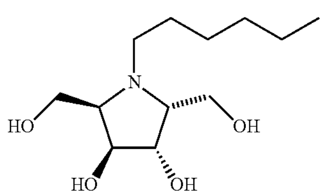 [SMILES: CCCCCCN1[C@H](CO)[C@H](O)[C@@H](O)[C@H]1CO] |
| (2R,3R,4R,5R)-1-benzyl-2,5-bis(hydroxymethyl)pyrrolidine-3,4-diol | 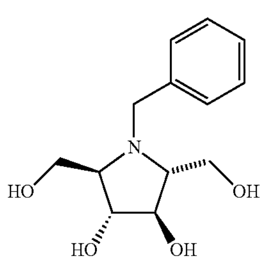 [SMILES: OC[C@@H]1[C@@H](O)[C@H](O)[C@@H](CO)N1Cc1ccccc1] |

TABLE 2-continued

| Name | Structure |
|---|---|
| (2R,3S,4S,5R)-2,5-bis(hydroxymethyl)-1-octylpyrrolidine-3,4-diol | 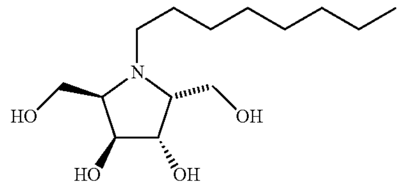 [SMILES: CCCCCCCCN1[C@H](CO)[C@H](O)[C@@H](O)[C@H]1CO] |
| (2R,3R,4R,5R)-2,5-bis(hydroxymethyl)-1-nonylpyrrolidine-3,4-diol | 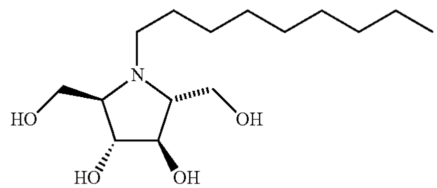 [SMILES: CCCCCCCCCN1[C@H](CO)[C@@H](O)[C@H](O)[C@H]1CO] |
| (2R,3S,4S,5R)-1-decyl-2,5-bis(hydroxymethyl)pyrrolidine-3,4-diol | 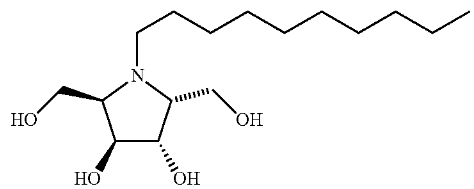 [SMILES: CCCCCCCCCCN1[C@H](CO)[C@H](O)[C@@H](O)[C@H]1CO] |
| (2R,3R,4R,5R)-2,5-bis(hydroxymethyl)-1-(9-hydroxynonyl)pyrrolidine-3,4-diol | 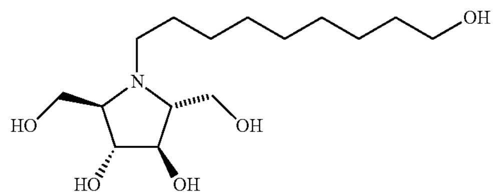 [SMILES: OCCCCCCCCCN1[C@H](CO)[C@@H](O)[C@H](O)[C@H]1CO] |
| (2R,3R,4R,5R)-2,5-bis(hydroxymethyl)-1-((R)-1-phenylethyl)pyrrolidine-3,4-diol | 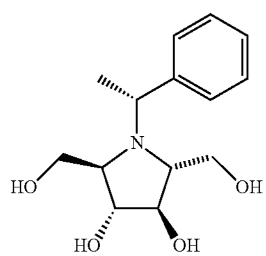 [SMILES: C[C@H](c1ccccc1)N1[C@H](CO)[C@@H](O)[C@H](O)[C@H]1CO] |
| (2R,3R,4R,5R)-2,5-bis(hydroxymethyl)-1-((S)-1-phenylethyl)pyrrolidine-3,4-diol | 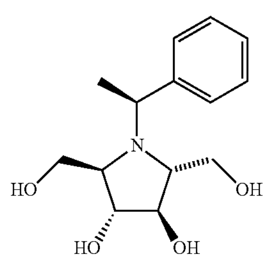 [SMILES: C[C@@H](c1ccccc1)N1[C@H](CO)[C@@H](O)[C@H](O)[C@H]1CO] |
| (2R,3S,4S,5R)-1-hexadecyl-2,5-bis(hydroxymethyl)pyrrolidine-3,4-diol | 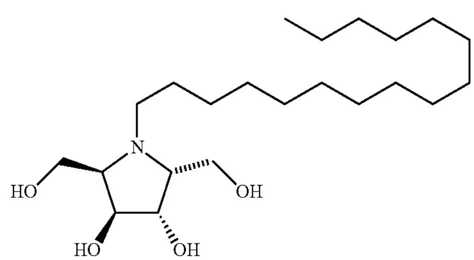 [SMILES: CCCCCCCCCCCCCCCCN1[C@H](CO)[C@H](O)[C@@H](O)[C@H]1CO] |

TABLE 2-continued

| Name | Structure |
|---|---|
| (2R,3R,4R,5R)-2,5-bis(hydroxymethyl)-1-octadecylpyrrolidine-3,4-diol | 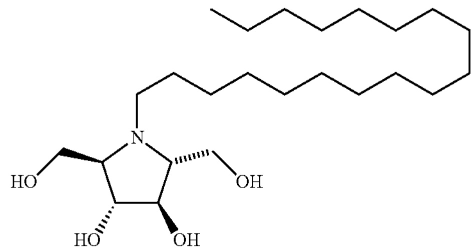 [SMILES: CCCCCCCCCCCCCCCCCCN1[C@H](CO)[C@@H](O)[C@H](O)[C@H]1CO] |
| (2R,3R,4R,5R)-1-benzhydryl-2,5-bis(hydroxymethyl)pyrrolidine-3,4-diol | 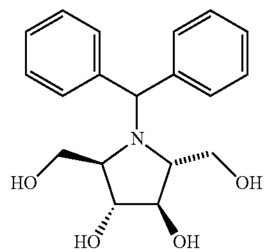 [SMILES: OC[C@@H]1[C@@H](O)[C@H](O)[C@@H](CO)N1C(c1ccccc1)c1ccccc1] |
| (2R,3R,4R,5R)-1-([1,1'-biphenyl]-4-ylmethyl)-2,5-bis(hydroxymethyl)pyrrolidine-3,4-diol | 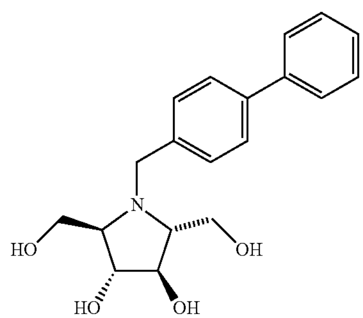 [SMILES: OC[C@@H]1[C@@H](O)[C@H](O)[C@@H](CO)N1Cc1ccc(-c2ccccc2)cc1] |
| (2R,3R,4R,5R)-1-(4-fluorophenethyl)-2,5-bis(hydroxymethyl)pyrrolidine-3,4-diol | 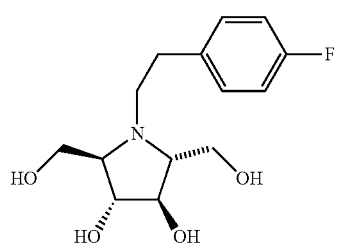 [SMILES: OC[C@@H]1[C@@H](O)[C@H](O)[C@@H](CO)N1CCc1ccc(F)cc1] |
| (2R,3R,4R,5R)-2-(hydroxymethyl)-5-methylpyrrolidine-3,4-diol | 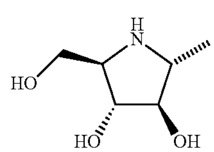 |
| (2R,3S,4R,5R)-2-(hydroxymethyl)-5-methylpyrrolidine-3,4-diol | 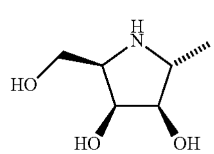 |
| (2R,3R,4S,5R)-2-(hydroxymethyl)-5-methylpyrrolidine-3,4-diol | 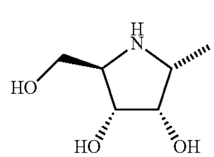 |

TABLE 2-continued

| Name | Structure |
| --- | --- |
| (2R,3S,4S,5R)-2-(hydroxymethyl)-5-methylpyrrolidine-3,4-diol | 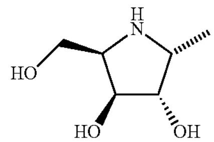 |
| (2R,3R,4R,5R)-1-butyl-2-(hydroxymethyl)-5-methylpyrrolidine-3,4-diol | 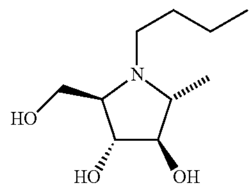 |
| (2R,3R,4S,5R)-2-(hydroxymethyl)-5-methyl-1-nonylpyrrolidine-3,4-diol | 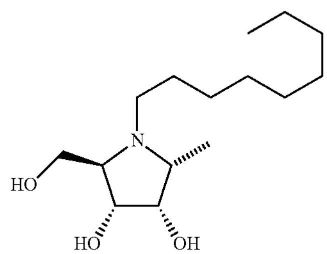 [SMILES: CCCCCCCCCN1[C@H](C)[C@H](O)[C@H](O)[C@H]1CO] |
| (2R,3S,4S,5R)-2,5-dimethylpyrrolidine-3,4-diol | 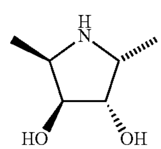 |
| (2R,3R,4R,5R)-2,5-dimethylpyrrolidine-3,4-diol | 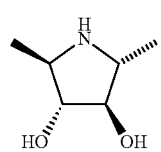 |
| (2R,3S,4R,5R)-2,5-dimethylpyrrolidine-3,4-diol | 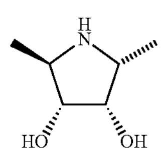 |
| (2R,3R,4S,5R)-1-benzyl-2,5-dimethylpyrrolidine-3,4-diol | 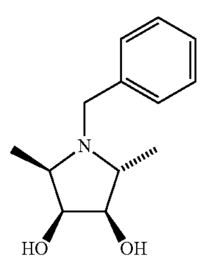 [SMILES: C[C@@H]1[C@H](O)[C@H](O)[C@@H](C)N1Cc1ccccc1] |

In alternative embodiments of the invention, compounds according to Formula (I) include one or more of the compounds described in Table 2 in which one or more OH groups are replaced by F or H.

In alternative embodiments of the invention, one or more of the compounds described in Table 2 in which one or more OH groups is replaced by F or H are specifically excluded from the compounds described in Formula (I).

As will be appreciated by a person skilled in the art, Formula (I) above may also be represented alternatively as follows:

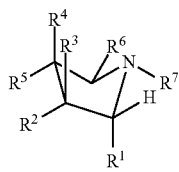

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to eighteen carbon atoms, such as 1, 2, 3, 4, 5, 6, 7, 8, 9, 10, 11, 12, 13, 14, 15, 16, 17, or 18 carbon atoms, and which is attached to the rest of the molecule by a single bond. In alternative embodiments, the alkyl group may contain from one to ten carbon atoms, such as 1, 2, 3, 4, 5, 6, 7, 8, 9, or 10 carbon atoms. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. In alternative embodiments, the alkenyl group may contain from two to eight carbon atoms, such as 2, 3, 4, 5, 6, 7, or 8 carbon atoms. In alternative embodiments, the alkenyl group may contain from three to six carbon atoms, such as 3, 4, 5, or 6 carbon atoms. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. In alternative embodiments, the alkynyl group may contain from two to eight carbon atoms, such as 2, 3, 4, 5, 6, 7, or 8 carbon atoms. In alternative embodiments, the alkynyl group may contain from three to six carbon atoms, such as 3, 4, 5, or 6 carbon atoms. Unless stated otherwise specifically in the specification, the alkynyl group may be optionally substituted by one or more substituents as described herein.

"Aryl" refers to a mono- or bicyclic aromatic ring containing only carbon atoms, including for example, 6-14 members, such as 6, 7, 8, 9, 10, 11, 12, 13, or 14 members. Examples of aryl groups include phenyl, biphenyl, naphthyl, indanyl, indenyl, tetrahydronaphthyl, 2,3-dihydrobenzofuranyl, dihydrobenzopyranyl, 1,4-benzodioxanyl, and the like. Unless stated otherwise specifically herein, the term "aryl" is meant to include aryl groups optionally substituted by one or more substituents as described herein.

"Heteroaryl" refers to a single or fused aromatic ring group containing one or more heteroatoms in the ring, for example N, O, S, including for example, 5-14 members, such as 5, 6, 7, 8, 9, 10, 11, 12, 13, or 14 members. Examples of heteroaryl groups include furan, thiophene, pyrrole, oxazole, thiazole, imidazole, pyrazole, isoxazole, isothiazole, 1,2,3-oxadiazole, 1,2,3-triazole, 1,2,4-triazole, 1,3,4-thiadiazole, tetrazole, pyridine, pyridazine, pyrimidine, pyrazine, 1,3,5-triazine, imidazole, benzimidazole, benzoxazole, benzothiazole, indolizine, indole, isoindole, benzofuran, benzothiophene, 1H-indazole, purine, 4H-quinolizine, quinoline, isoquinoline, cinnoline, phthalazine, quinazoline, quinoxaline, 1,8-naphthyridine, pteridine, and the like. Unless stated otherwise specifically herein, the term "heteroaryl" is meant to include heteroaryl groups optionally substituted by one or more substituents as described herein.

"Arylalkyl" refers to a group of the formula —$R_aR_b$ where $R_a$ is a $C_{1-10}$ alkyl group as described herein and $R_b$ is one or more aryl moieties as described herein. The aryl group(s) may be optionally substituted as described herein.

"Arylalkenyl" refers to a group of the formula —$R_cR_b$ where $R_c$ is a $C_{2-10}$ alkenyl group as described herein and $R_b$ is one or more aryl moieties as described herein. The aryl group(s) may be optionally substituted as described herein.

"Arylalkynyl" refers to a group of the formula —$R_dR_b$ where $R_d$ is a $C_{2-10}$ alkynyl group as described herein and $R_b$ is one or more aryl moieties as described herein. The aryl group(s) may be optionally substituted as described herein.

"Heteroarylalkyl" refers to a group of the formula —$R_aR_c$ where $R_a$ is a $C_{1-10}$ alkyl group as described herein and $R_c$ is one or more heteroaryl moieties as described herein. The aryl group(s) may be optionally substituted as described herein.

"Heteroarylalkenyl" refers to a group of the formula —$R_cR_e$ where $R_c$ is a $C_{2-10}$ alkenyl group as described herein and $R_e$ is one or more heteroaryl moieties as described herein. The heteroaryl group(s) may be optionally substituted as described herein.

"Heteroarylalkynyl" refers to a group of the formula —$R_dR_e$ where $R_d$ is a $C_{2-10}$ alkynyl group as described herein and $R_e$ is one or more heteroaryl moieties as described herein. The heteroaryl group(s) may be optionally substituted as described herein.

"Acyl" refers to a group of the formula —$C(O)R_f$, where $R_f$ is H or a $C_{1-10}$ alkyl group or a $C_{1-6}$ alkyl group or a $C_{3-15}$ cycloalkyl group as described herein. The alkyl or cycloalkyl group(s) may be optionally substituted as described herein.

"Arylalkylacyl" refers to a group of the formula —$C(O)R_gR_b$, where $R_g$ is a $C_{1-10}$ alkyl or a $C_{1-6}$ alkyl group as described herein and $R_b$ is one or more aryl moieties as described herein. The alkyl or aryl group(s) may be optionally substituted as described herein.

"Heteroarylalkylacyl" refers to a group of the formula —$C(O)R_gR_e$, where $R_g$ is a $C_{1-10}$ alkyl or a $C_{1-6}$ alkyl group as described herein and $R_e$ is one or more heteroaryl moieties as described herein. The alkyl or heteroaryl group(s) may be optionally substituted as described herein.

"Alkoxy" refers to a group of the formula —$OR_g$, where $R_g$ is a $C_{1-10}$ alkyl or a $C_{1-6}$ alkyl group as described herein. The alkyl group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. In alternative embodiments, the cycloalkyl group may contain from three to six carbon atoms, such as 3, 4, 5, or 6 carbon atoms. Unless otherwise stated specifically herein, the term "cycloalkyl" is meant to include cycloalkyl groups which are optionally substituted as described herein.

"Halo" refers to bromo, chloro, fluoro, iodo, etc. In some embodiments, suitable halogens include fluorine or chlorine.

"Optional" or "optionally" means that the subsequently described event of circumstances may or may not occur, and that the description includes instances where said event or circumstance occurs one or more times and instances in which it does not. For example, "optionally substituted alkyl" means that the alkyl group may or may not be substituted and that the description includes both substituted alkyl groups and alkyl groups having no substitution, and that said alkyl groups may be substituted one or more times. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions may include, without limitation, Glaucoma, Schizophrenia, tauopathies, such as Alzheimer's disease, neurodegenerative diseases, cardiovascular diseases, diseases associated with inflammation, diseases associated with immunosuppression and cancers. One or more of the compounds of the invention may also be useful in the treatment of diseases or disorders related to deficiency or over-expression of O-GlcNAcase or accumulation or depletion of O-GlcNAc, or any disease or disorder responsive to glycosidase inhibition therapy. Such diseases and disorders may include, but are not limited to, Glaucoma, Schizophrenia, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification may result in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels may be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

In general, the methods of the invention may be effected by administering a compound according to the invention to a subject in need thereof, or by contacting a cell or a sample with a compound according to the invention, for example, a pharmaceutical composition comprising a therapeutically effective amount of the compound according to Formula (I). More particularly, they may be useful in the treatment of a disorder in which the regulation of O-GlcNAc protein modification is implicated, or any condition as described herein. Disease states of interest may include Alzheimer's disease (AD) and related neurodegenerative tauopathies, in which abnormal hyperphosphorylation of the microtubule-associated protein tau is involved in disease pathogenesis. In some embodiments, a compound may be used to block hyperphosphorylation of tau by maintaining elevated levels of O-GlcNAc on tau, thereby providing therapeutic benefit.

The effectiveness of a compound in treating pathology associated with the accumulation of toxic tau species (for example, Alzheimer's disease and other tauopathies) may be confirmed by testing the ability of a compound to block the formation of toxic tau species in established cellular[121-123] and/or transgenic animal models of disease.[33,34]

Tauopathies that may be treated with a compound of the invention may include, without limitation: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention may also be useful in the treatment of conditions associate with tissue damage or stress, stimulating cells, or promoting differentiation of cells. Accordingly, in some embodiments, a compound of this invention may be used to provide therapeutic benefit in a variety of conditions or medical procedures involving stress in cardiac tissue; such conditions may include, without limitation: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays,[108,119,120] and to prevent tissue damage and promote functional recovery in animal models of ischemia-reperfusion,[71,117] and trauma-hemorrhage.[73,115,118]

Compounds that selectively inhibit O-GlcNAcase activity may be used for the treatment of diseases that are associated with inflammation; such conditions may include, without limitation: inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myasthenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affect levels of protein O-GlcNAc modification may be used for the treatment of diseases associated with immunosuppression, such as, for example, in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegenerative diseases; such conditions may include, without limitation, Parkinson's disease and Huntington's disease. Other conditions that may be treated are those triggered, affected, or in any other way correlated with levels of O-GlcNAc post-translational protein modification. It is expected that one or more of the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I) are provided.

The compounds of Formula (I) and their pharmaceutically acceptable salts, enantiomers, solvates, and derivatives may be useful because they may have pharmacological activity in animals, including humans. In some embodiments, one or more of the compounds according to the invention may be stable in plasma, when administered to a subject.

In some embodiments, a compound according to the invention, or for use according to the invention, may be provided in combination with any other active agents or pharmaceutical compositions where such combined therapy may be useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents may include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (ZT-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-Z1, CTS-21166, MK-8931, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfurindamide, LiCl, AZD1080, NP031112, SAR-502250, etc.

humanized monoclonal anti-Aβ antibodies such as Bapineuzumab (AAB-001), LY2062430, RN1219, ACU-5A5, etc.;

amyloid vaccines such as AN-1792, ACC-001, etc.;

neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but may include combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, a compound may be supplied as a "prodrug" or protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but may be converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987.

Suitable prodrug forms of one or more of the compounds of the invention may include embodiments in which one or more OH groups as set forth in Formula (I) may be protected as OC(O)R, where R may be optionally substituted alkyl, alkenyl, alkynyl, aryl, or heteroaryl. In these cases the ester groups may be hydrolyzed in vivo (e.g. in bodily fluids), liberating the OH groups and releasing the active compounds. Preferred prodrug embodiments of the invention may include compounds of Formula (I) where one or more OH groups may be protected with acetate, for example as $OC(O)CH_3$.

Compounds according to the invention, or for use according to the invention, may be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, omithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require modulation of O-GlcNAcase activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition of an O-GlcNAcase, elevation of O-GlcNAc levels, inhibition of tau phosphorylation, or any condition described herein.

Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 M or 0.01 nM-10 μM.

In alternative embodiments, in the treatment or prevention of conditions which may require modulation of O-GlcNAcase activity, an appropriate dosage level may generally be about 0.01 to 500 mg per kg subject body weight per day, and may be administered in singe or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H), deuterium ($^2$H) and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) may be prepared without undue experimentation by conventional techniques well known to those skilled in the art or by processes analogous to those described in the Schemes and Examples herein using appropriate isotopically-enriched reagents and/or intermediates.
Other Uses and Assays A compound of Formula (I) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluoresence or UV-based assay known in the art may be used. A "test compound" may be any naturally-occurring or artificially-derived chemical compound. Test compounds may include, without limitation, peptides, polypeptides, synthesised organic molecules, naturally occurring organic molecules, and nucleic acid molecules. A test compound may "compete" with a known compound such as a compound of Formula (I) by, for example, interfering with inhibition of O-GlcNAcase-dependent cleavage of O-GlcNAc or by interfering with any biological response induced by a compound of Formula (I).

Generally, a test compound may exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator may in general decrease modulation relative to a known compound, while a compound that is a positive modulator may in general increase modulation relative to a known compound.

In general, test compounds may be identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds may be screened using the exemplary methods described herein. Examples of such extracts or compounds may include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, that may include, without limitation, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries may be produced, if desired, according to methods known in the art, e.g., by standard extraction and fractionation methods. Furthermore, if desired, any library or compound may be readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract may be necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds may be used to purify the active component and to test derivatives thereof. Methods of fractionation and purification of such heterogeneous extracts are known in the art. If desired, compounds shown to be useful agents for treatment may be chemically modified according to methods known in the art. Compounds identified as being of therapeutic, prophylactic, diagnostic, or other value may be subsequently analyzed using a suitable animal model, as described herein on known in the art.

In some embodiments, one or more of the compounds may be useful in the development of animal models for studying diseases or disorders that may be related to deficiencies in O-GlcNAcase, over-expression of O-GlcNAcase, accumulation of O-GlcNAc, depletion of O-GlcNAc, and for studying treatment of diseases and disorders that may be related to deficiency or over-expression of O-GlcNAcase, or accumulation or depletion of O-GlcNAc. Such diseases and disorders may include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations

ABCN=1,1'-azobis(cyclohexane-carbonitrile)
AcCl=acetyl chloride
AIBN=azobisisobutyronitrile
$BCl_3$=boron trichloride
BnBr=benzyl bromide
$Bu_4NI$=tetra-n-butylammonium iodide
$Boc_2O$=di-tert-butyl dicarbonate
BzCl=benzoyl chloride
DAST=diethylaminosulfur trifluoride
DCM=dichloromethane
DIAD=diisopropyl azodicarboxylate
DIPEA=diisopropylethylamine
DMAP=4-dimethylaminopyridine
DMF=N,N-dimethylformamide
DMP=Dess-Martin periodinane
DMSO=dimethyl sulfoxide
EDCI=1-ethyl-3-(3-dimethylaminopropyl)carbodiimide
$Et_3N$=triethylamine
$Et_2O$=diethyl ether
HATU=(O-(7-azabenzotriazol-1-yl)-N,N,N',N'-tetramethyl-uronium hexafluorophosphate)
PMB=pentamethylbenzene
TBDMSCl=tert-butyldimethylsilyl chloride
TBAF=tetra-n-butylammonium fluoride
$TMSCF_3$=(trifluoromethyl)trimethylsilane
TFA=2,2,2-trifluoroacetic acid
THF=tetrahydrofuran
thio-CDI=1,1'-thiocarbonyl diimidazole General Procedures and Intermediates The compounds of the invention are synthesized according to standard schemes and procedures, as indicated in, for example, Schemes 1 to 27, as appropriate. Intermediate A (Scheme 15) may be prepared as described in, for example, *Tetrahedron* 2009, 65, 93-100. Intermediate B (Scheme 26) may be prepared as described in, for example, *Tetrahedron* 1994, 50, 4215 and PCT WO 1997/009040. For Schemes 2 to 27, the general procedures are defined as follows:

General procedure A: $Pd(OH)_2/H_2$, MeOH, 50° C., 50 psi
General Procedure B: RCHO, $NaBH_3CN$, HOAc, MeOH
General Procedure C: 4N HCl, 40° C.
General Procedure D: RCOOH, HATU, DMF, i-$Pr_2NEt$
General Procedure E: RBr, $K_2CO_3$, DMF It is to be understood that any suitable scheme within the knowledge of one skilled in the art may be used to synthesize one or more of the compounds described herein.

Scheme 1

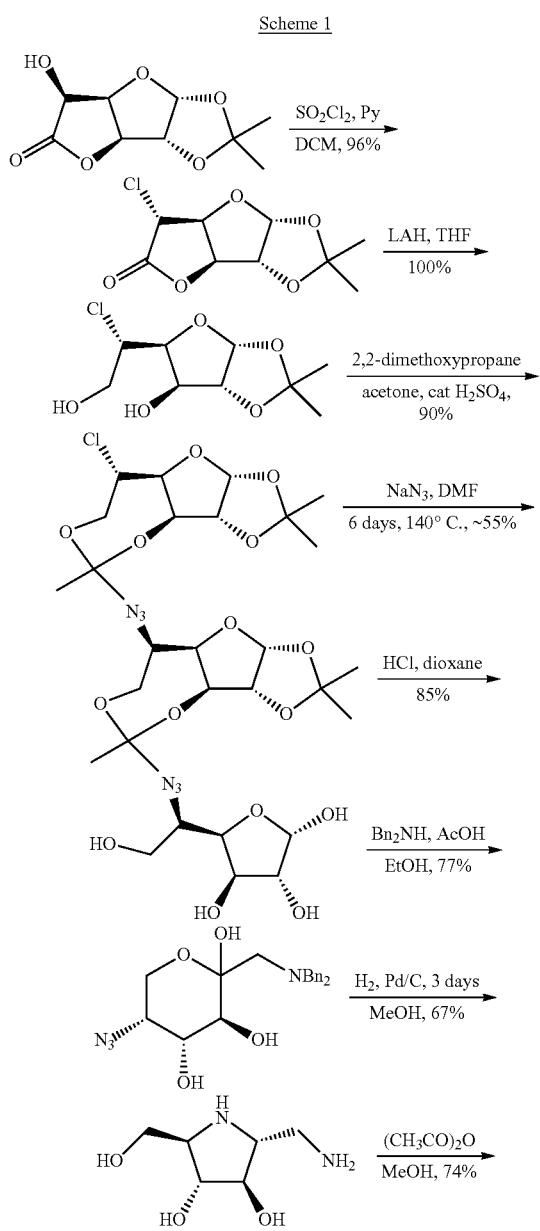

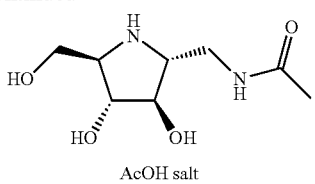

AcOH salt

Scheme 2

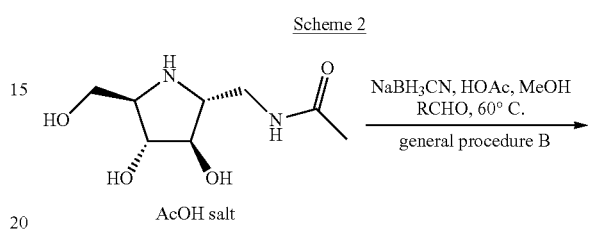

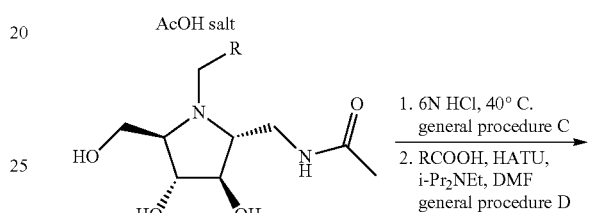

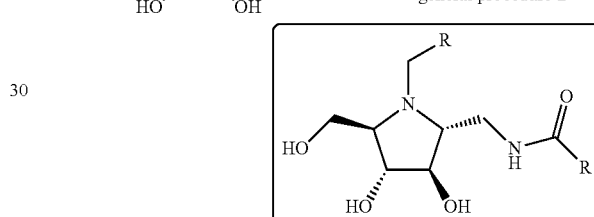

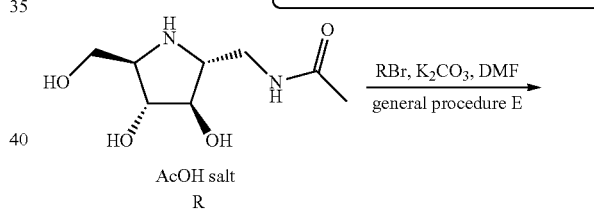

AcOH salt

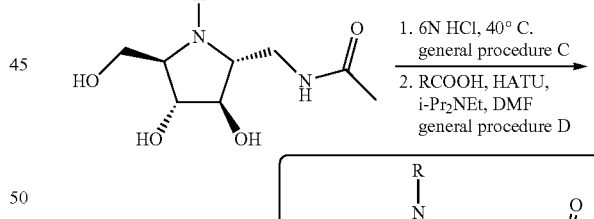

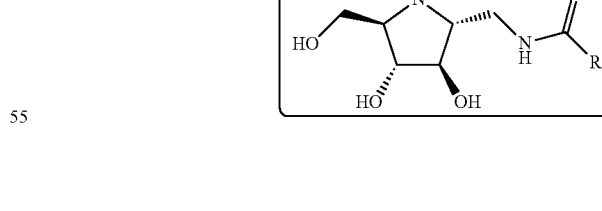

Scheme 3

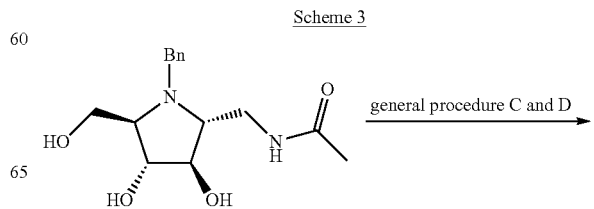

-continued
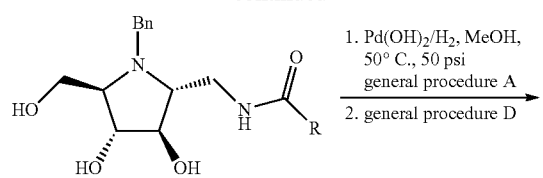
1. Pd(OH)₂/H₂, MeOH, 50° C., 50 psi
   general procedure A
2. general procedure D
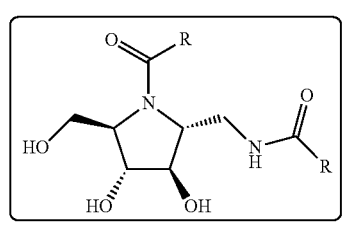
Scheme 4
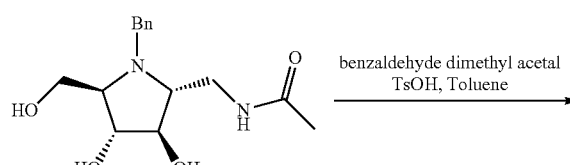
benzaldehyde dimethyl acetal
TsOH, Toluene
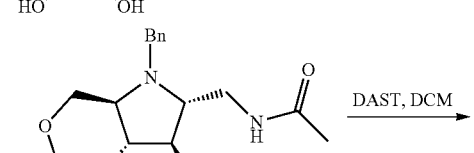
DAST, DCM
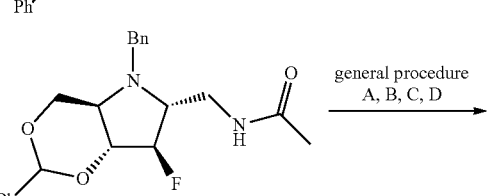
general procedure A, B, C, D
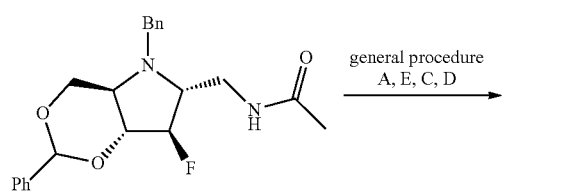
general procedure A, E, C, D
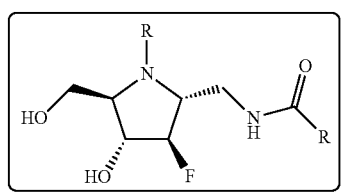
Scheme 5
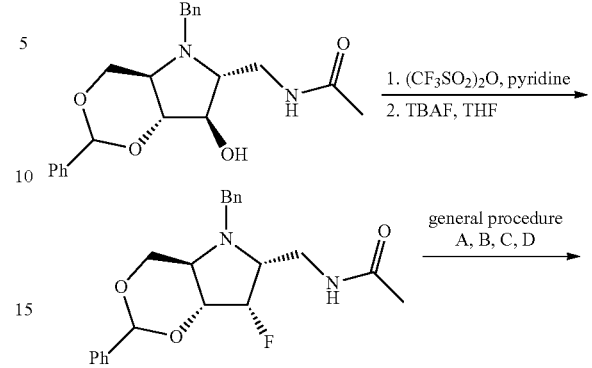
1. (CF₃SO₂)₂O, pyridine
2. TBAF, THF
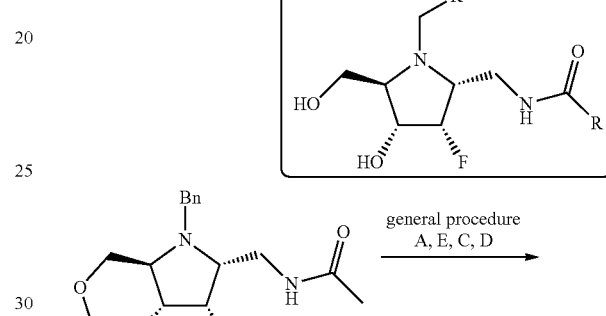
general procedure A, B, C, D
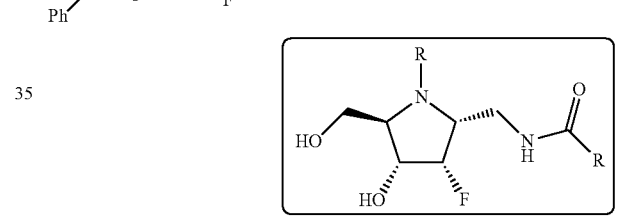
general procedure A, E, C, D
Scheme 6
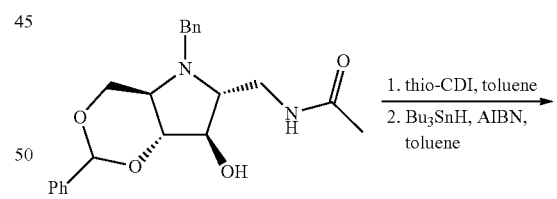
1. thio-CDI, toluene
2. Bu₃SnH, AIBN, toluene
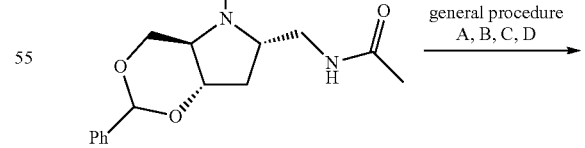
general procedure A, B, C, D

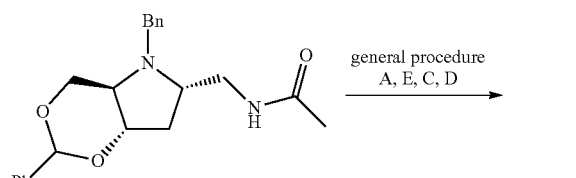
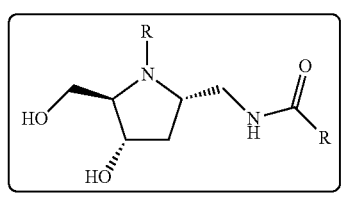
Scheme 7
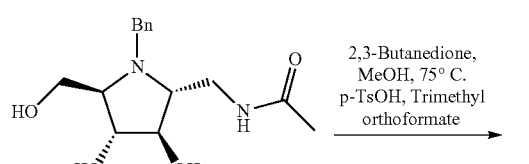
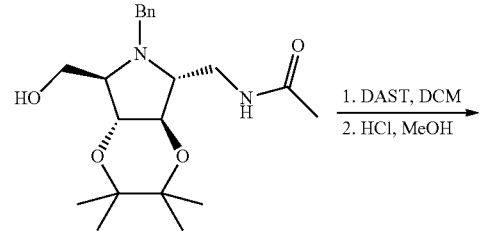
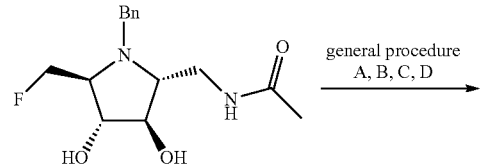
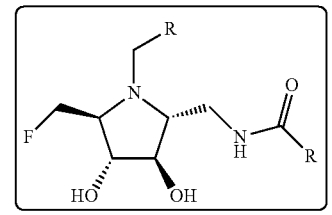
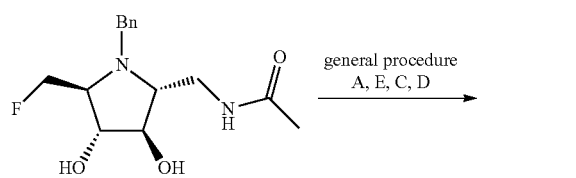
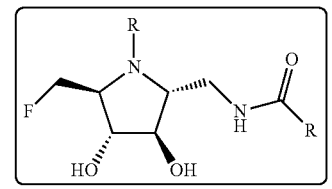
Scheme 8
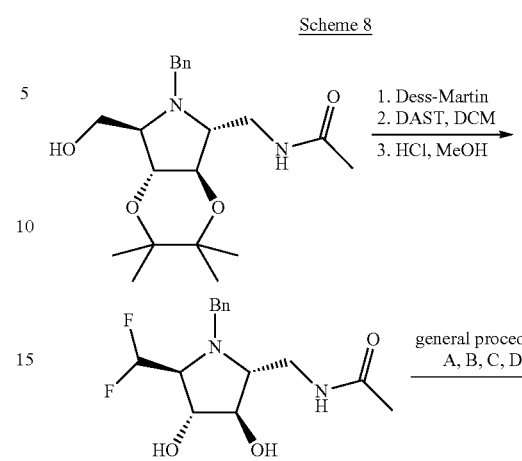
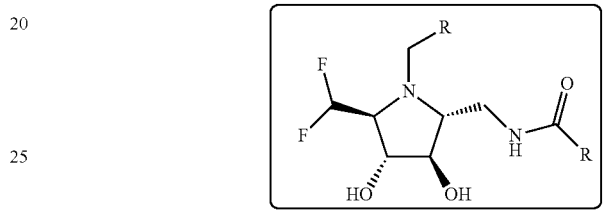
Scheme 9
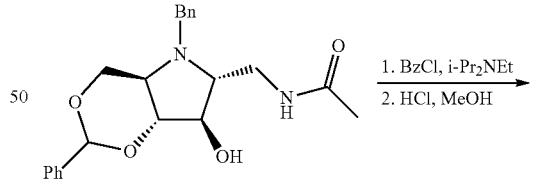
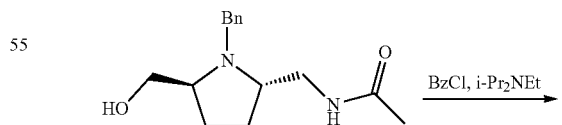
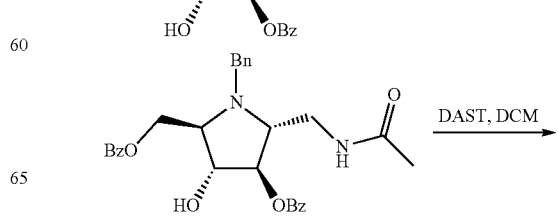

91
-continued
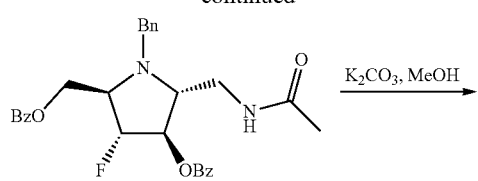
K₂CO₃, MeOH →
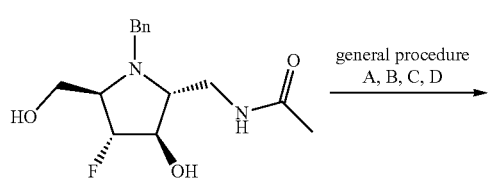
general procedure A, B, C, D →
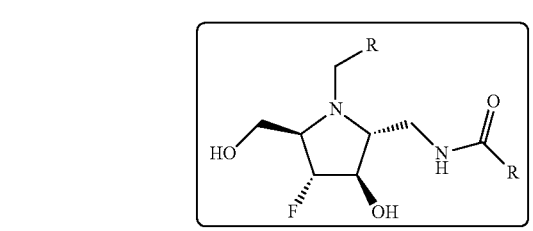
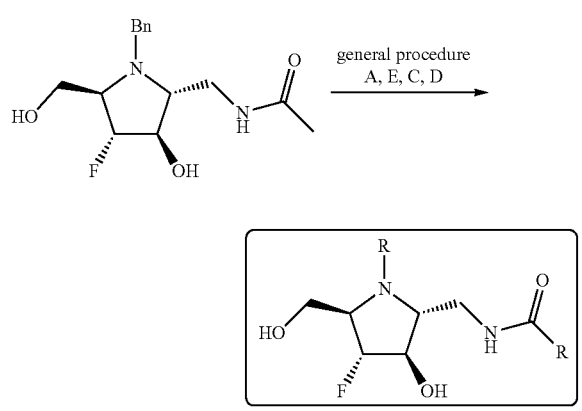
general procedure A, E, C, D →
92
-continued
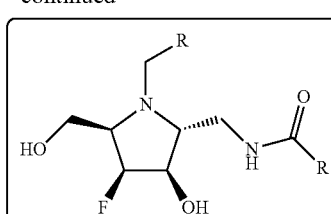
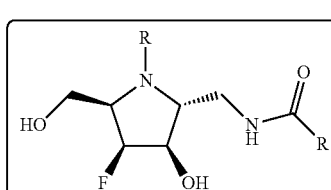
general procedure A, E, C, D →
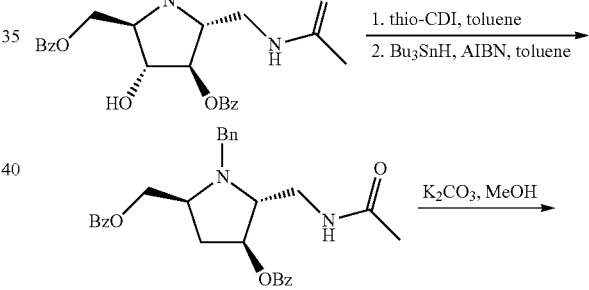
Scheme 11
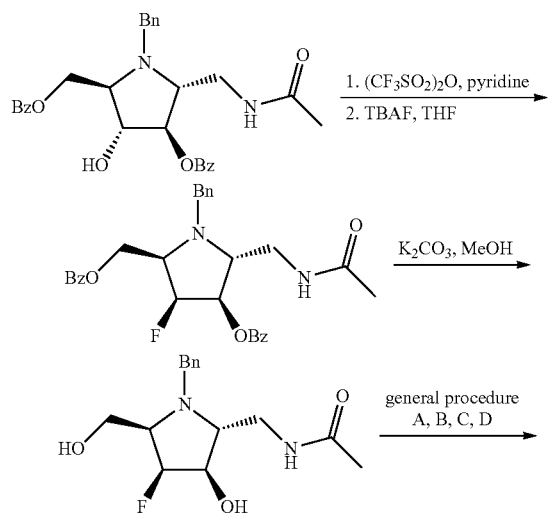
Scheme 10
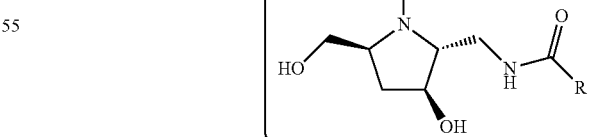
general procedure A, B, C, D →
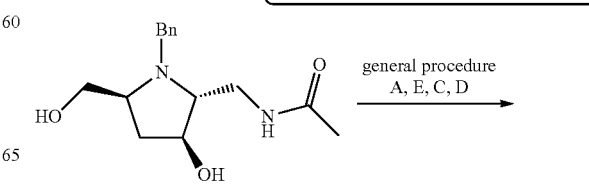
general procedure A, E, C, D →

93
-continued
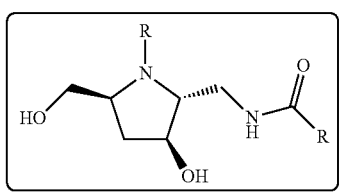
Scheme 12
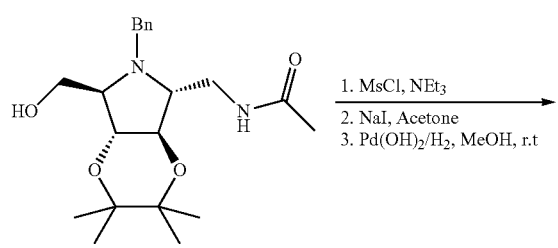
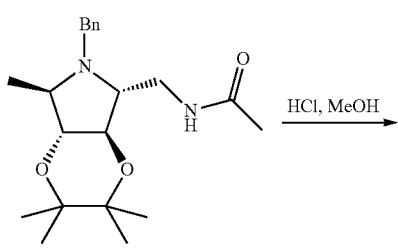
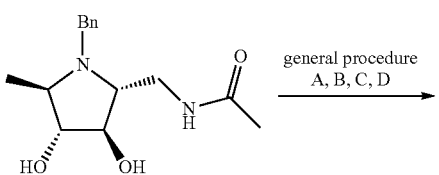
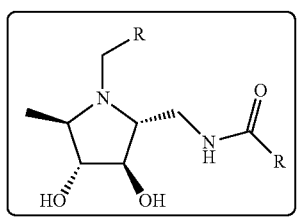
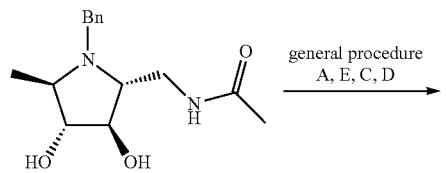
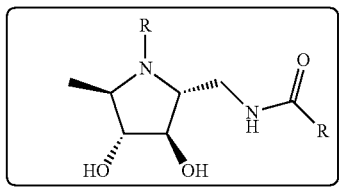
94
Scheme 13
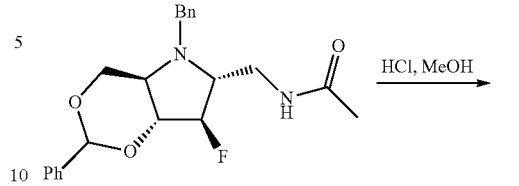
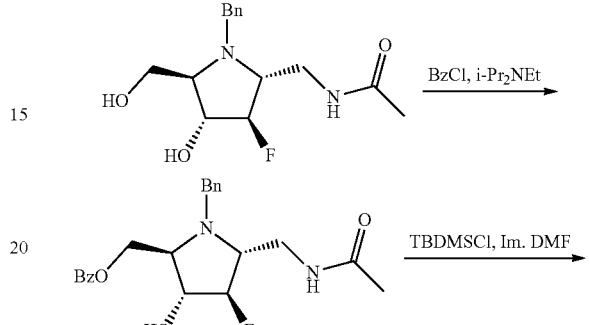
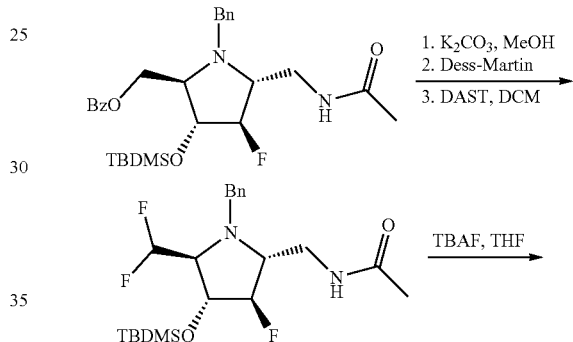
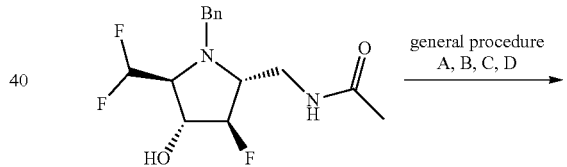
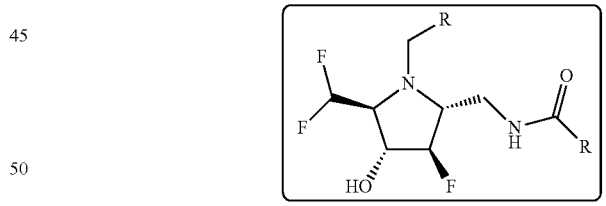
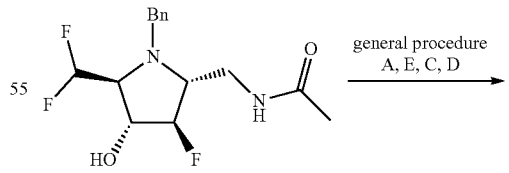
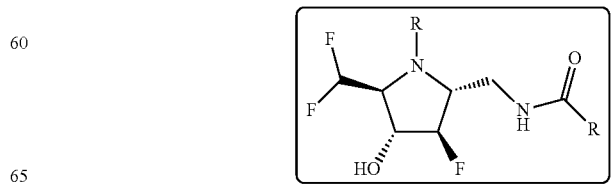

Scheme 14
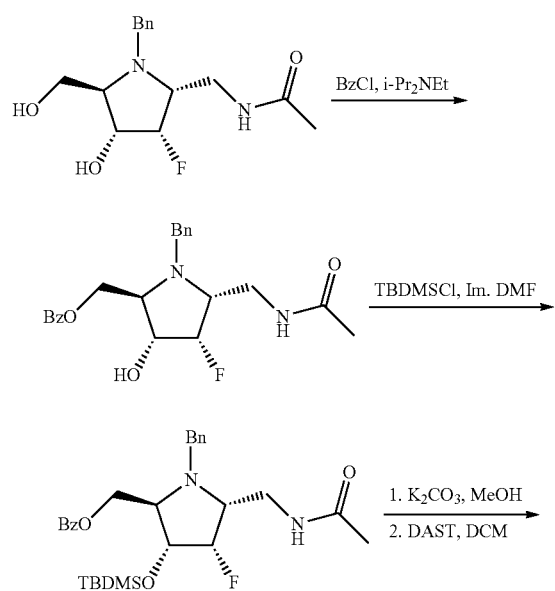
Scheme 15
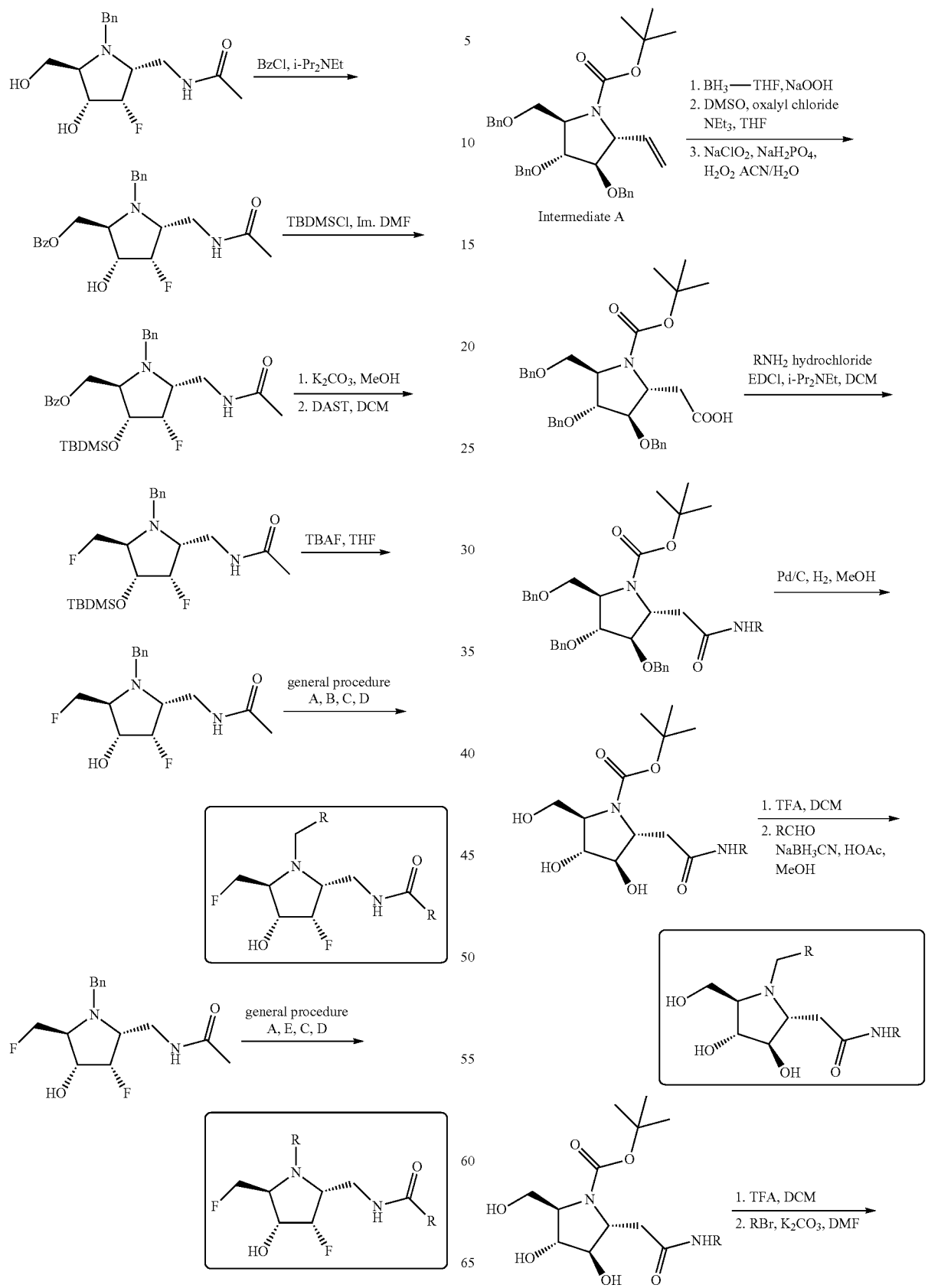

97
-continued
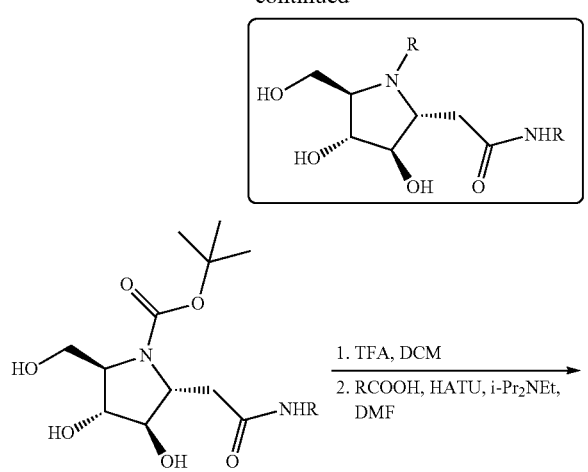
Scheme 16
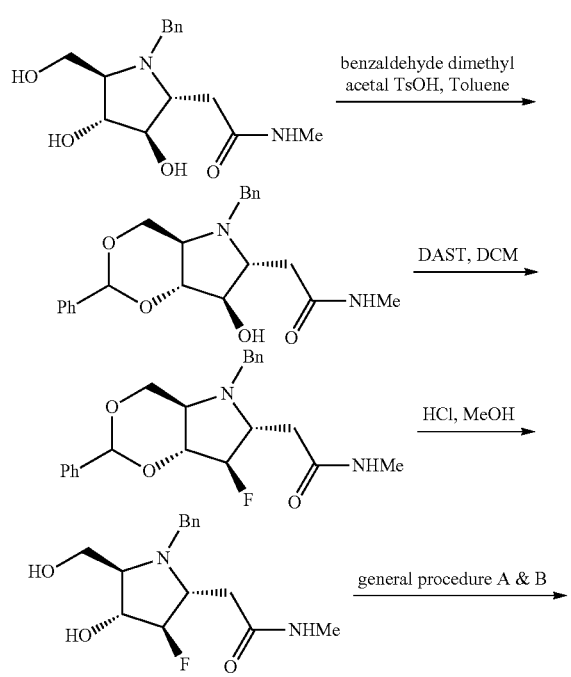
98
-continued
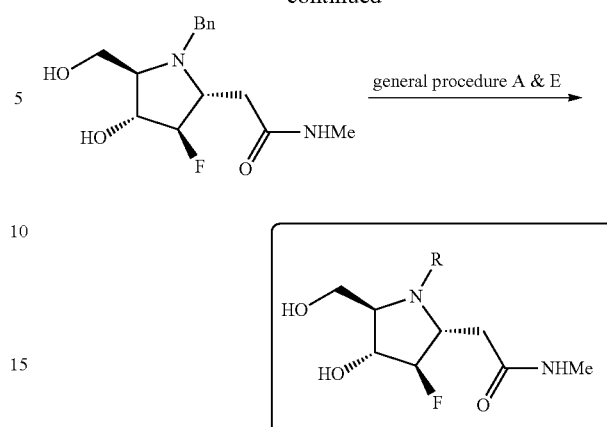
Scheme 17
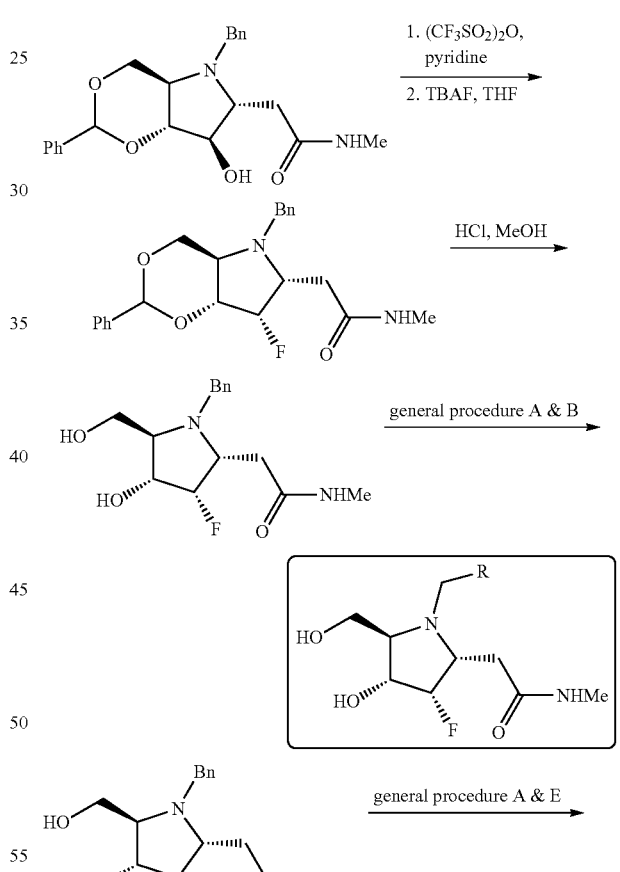

Scheme 18
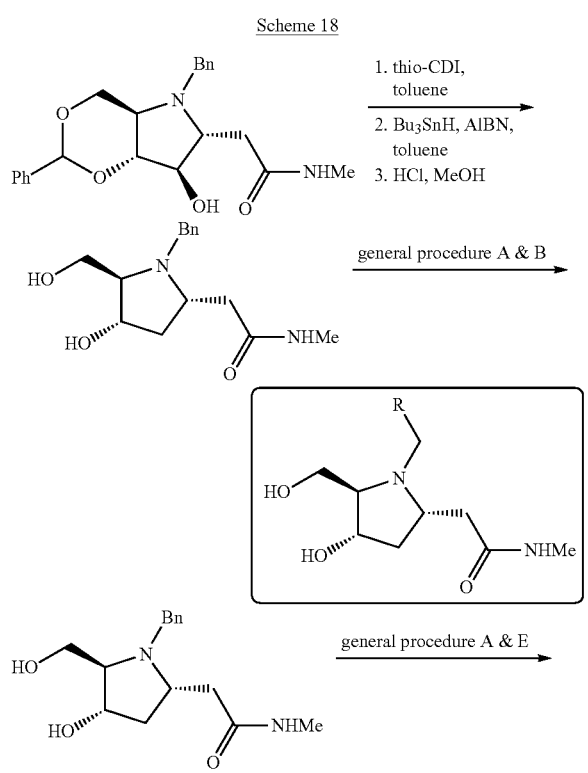
Scheme 19
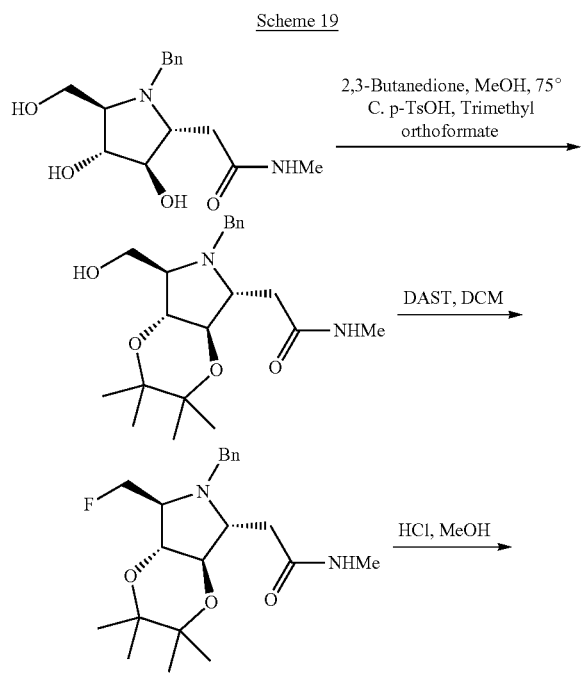
-continued
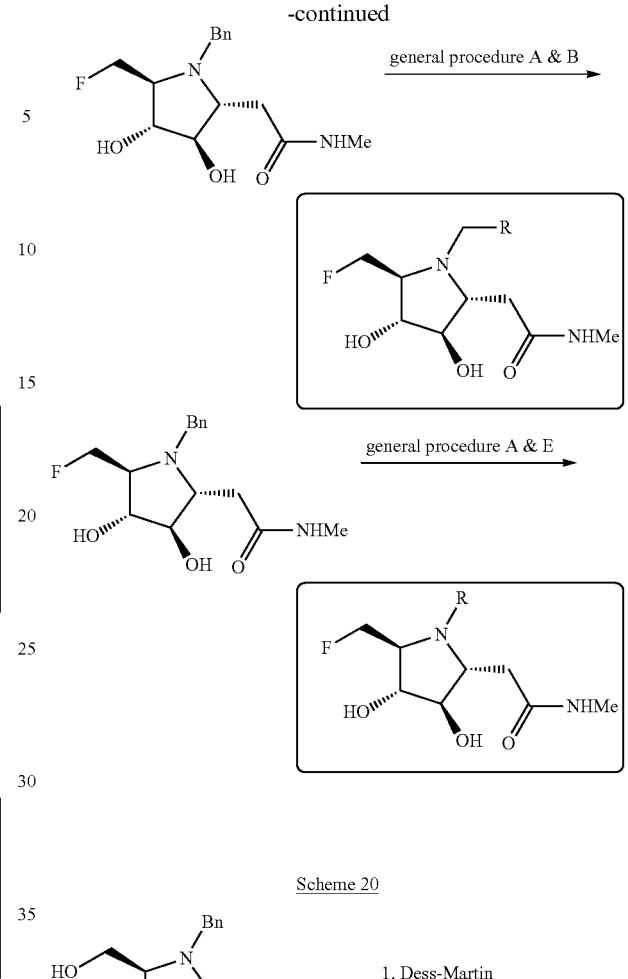
Scheme 20
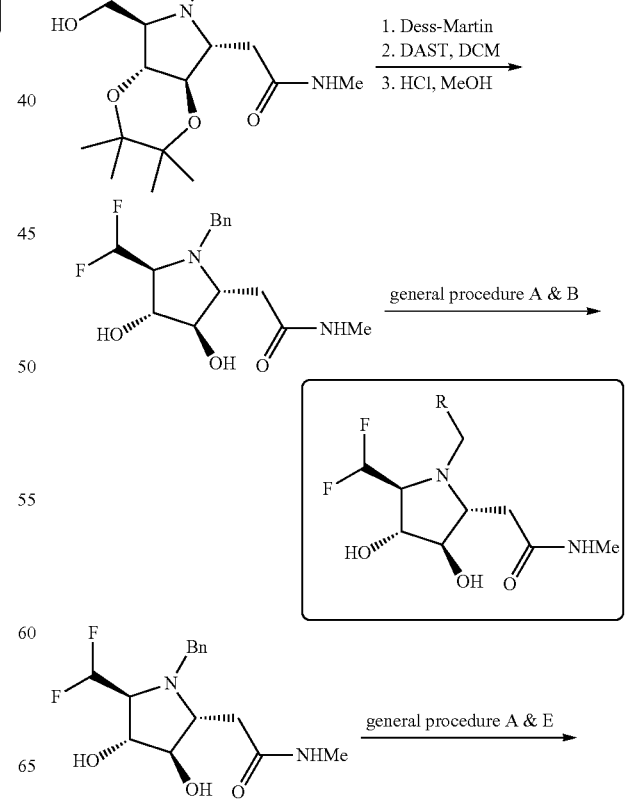

101
-continued
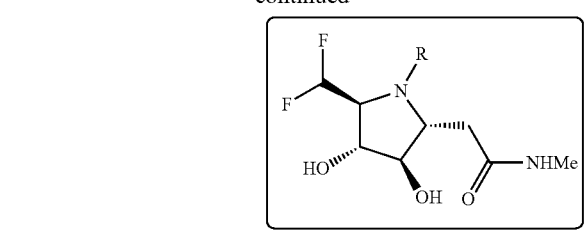
Scheme 21
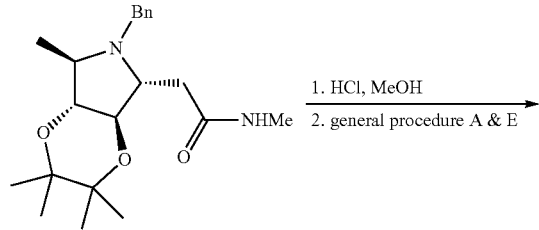
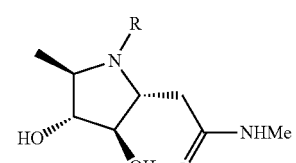
102
Scheme 22
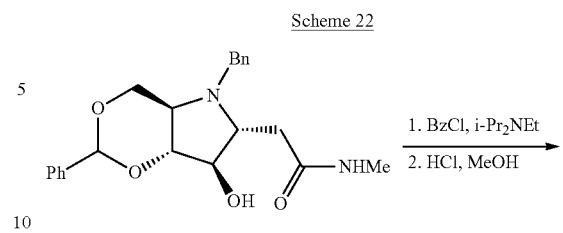
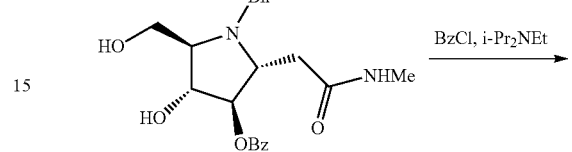
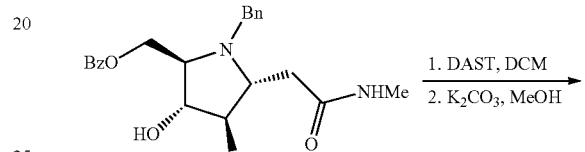
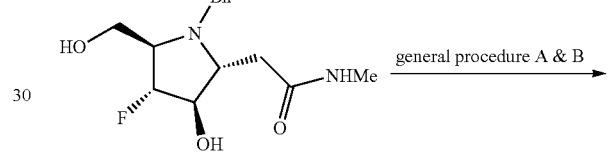
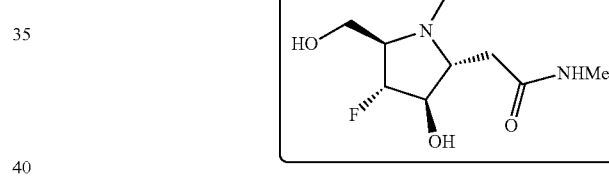
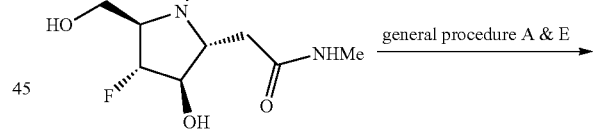
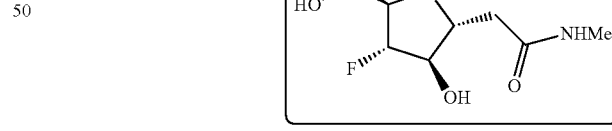
Scheme 23
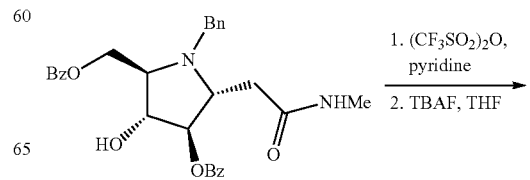

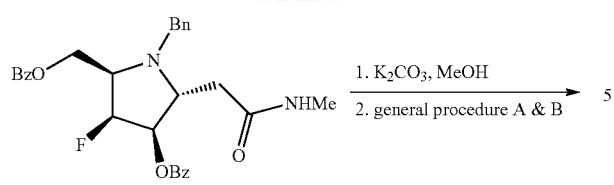
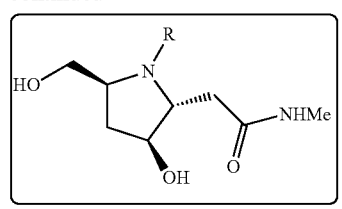
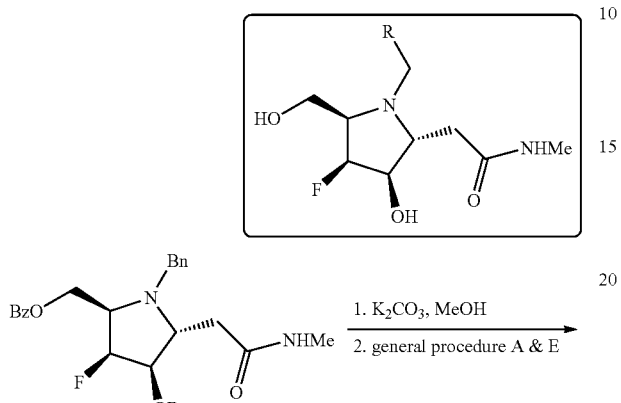
Scheme 24
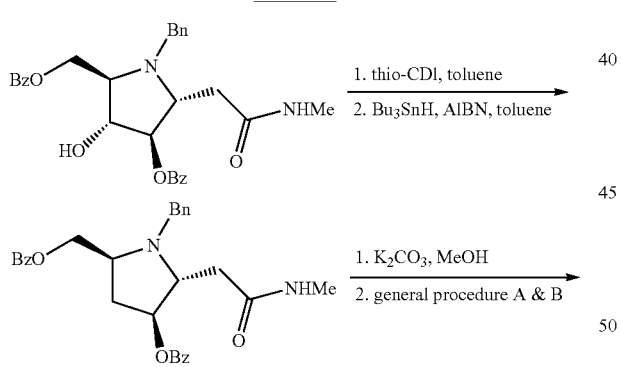
Scheme 25
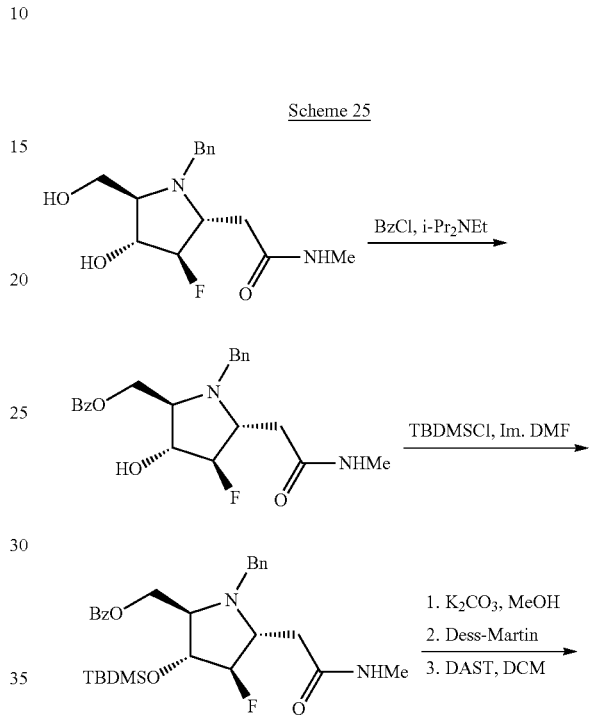
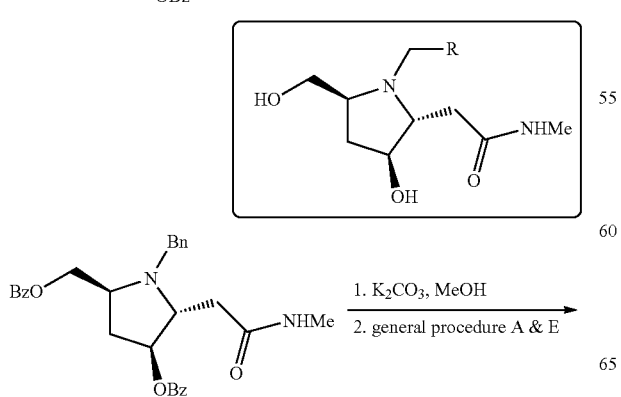
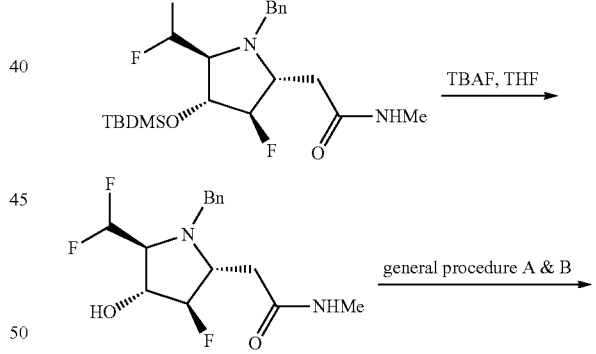
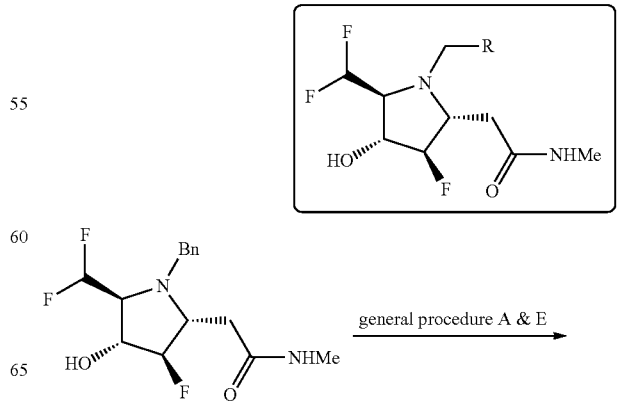

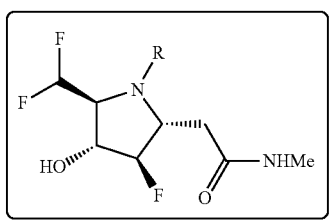
Scheme 26
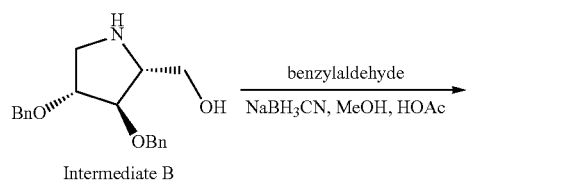
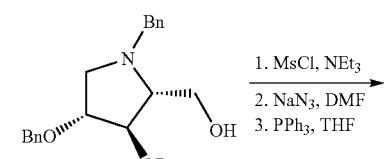
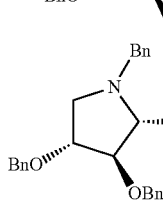
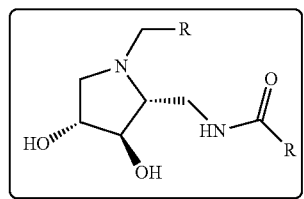
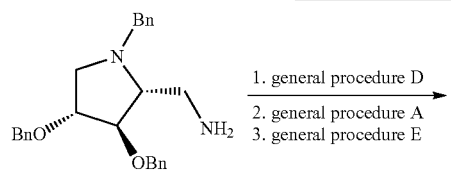
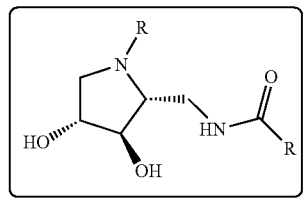
Scheme 27
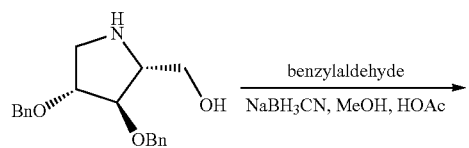
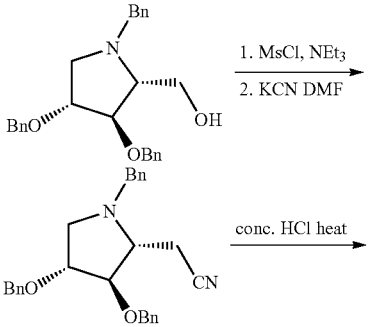
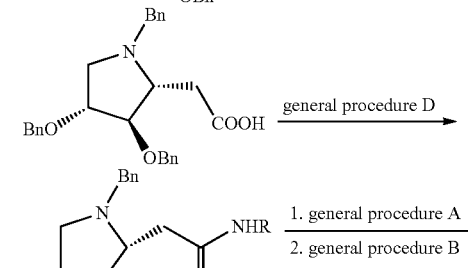
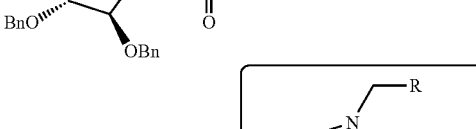
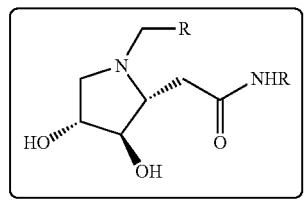
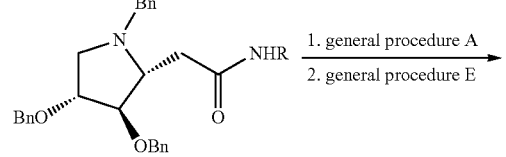
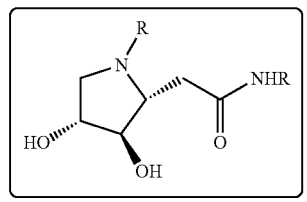
N-(((2R,3R,4R,5R)-3,4-dihydroxy-5-(hydroxymethyl)pyrrolidin-2-yl)methyl)acetamide
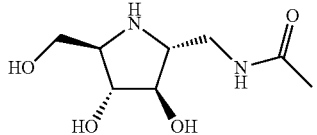
N-(((2R,3R,4R,5R)-3,4-dihydroxy-5-(hydroxymethyl)pyrrolidin-2-yl)methyl)acetamide was prepared using literature procedures as indicated in Scheme 1 (*Tetrahedron Letters*, 1997, 38(31), 5463-5466; *J. Carbohydrate Chemistry*, 2000, 19(8), 975-990). Characterization data for its CHCOOH salt: $^1$H NMR (400 MHz, CD$_3$OD) δ 3.87-3.83

(m, 1H), 3.79-3.72 (m, 2H), 3.67-3.63 (m, 1H), 3.49-3.44 (m, 1H), 3.42-3.38 (m, 1H), 3.26-3.18 (m, 2H), 1.98 (s, 3H), 1.93 (CH$_3$COOH); $^{13}$C NMR (125 MHz, CD$_3$OD) δ 179.97, 174.84, 78.61, 77.13, 65.37, 63.68, 60.47, 40.91, 23.82, 22.71. MS, (ES, m/z) [M+H]$^+$ 205.13.

General Procedure for Reductive Amination

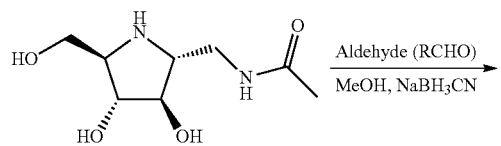

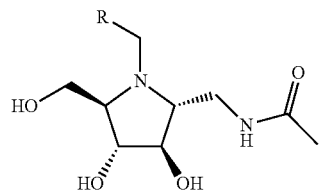

To a mixture of N-(((2R,3R,4R,5R)-3,4-dihydroxy-5-(hydroxymethyl)pyrrolidin-2-yl)methyl)acetamide (0.030 g, 0.15 mmol) and aldehyde (0.45 mmol) in methanol (2 mL) was added NaBH$_3$CN (0.030 g, 0.48 mmol). After the mixture was stirred at room temperature overnight, the solvent was removed under reduced pressure, and the residue was purified on silica gel by flash column chromatography (EtOAc, then MeOH/DCM, 1:8) to afford the product.

N-(((2R,3R,4R,5R)-1-benzyl-3,4-dihydroxy-5-(hydroxymethyl)pyrrolidin-2-yl)methyl)acetamide

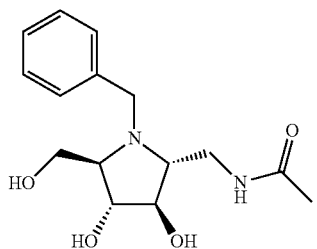 [SMILES: CC(=O)NC[C@@H]1[C@@H](O)[C@H](O)[C@@H](CO)N1Cc1ccccc1]

N-(((2R,3R,4R,5R)-1-benzyl-3,4-dihydroxy-5-(hydroxymethyl)pyrrolidin-2-yl)methyl)acetamide was prepared using the general procedure for reductive amination, using benzaldehyde. Very pale yellow oil. Yield 43%. $^1$H NMR (400 MHz, CD$_3$OD) δ 7.42-7.40 (m, 2H), 7.30-7.28 (m, 2H), 7.23-7.19 (m, 1H), 4.01 (t, J=2.4 Hz, 1H), 3.98-3.93 (m, 2H), 3.83-3.82 (m, 1H), 3.77 (dd, J=4.9, 11.4 Hz, 1H), 3.63 (dd, J=3.3, 11.4 Hz, 1H), 3.42 (dd, J=3.5, 13.9 Hz, 1H), 3.28 (dd, J=6.0, 13.9 Hz, 1H), 3.14-3.11 (m, 1H), 3.05-3.02 (m, 1H), 1.92 (s, 3H); $^{13}$C NMR (100 MHz, CD$_3$OD) δ 173.66, 140.90, 129.50, 129.46, 128.12, 81.29, 80.80, 70.07, 69.93, 61.15, 52.49, 40.38, 22.81. MS, (ES, m/z) [M+H]$^+$ 295.18.

N-(((2R,3R,4R,5R)-3,4-dihydroxy-5-(hydroxymethyl)-1-phenethylpyrrolidin-2-yl)methyl)acetamide

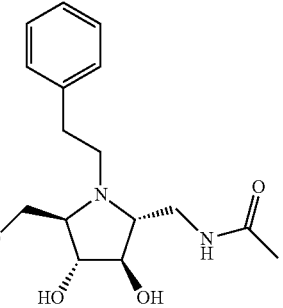

N-(((2R,3R,4R,5R)-3,4-dihydroxy-5-(hydroxymethyl)-1-phenethylpyrrolidin-2-yl)methyl)acetamide was prepared using the general procedure for reductive amination, using phenylacetaldehyde. Very pale yellow oil. Yield 45%. $^1$H NMR (400 MHz, CD$_3$OD) δ 7.29-7.24 (m, 4H), 7.19-7.14 (m, 1H), 3.97 (t, J=2.3 Hz, 1H), 3.83 (dd, J=4.7, 11.4 Hz, 1H), 3.74-3.70 (m, 2H), 3.54-3.50 (m, 1H), 3.17-3.14 (m, 1H), 3.11-3.02 (m, 3H), 2.89-3.83 (m, 2H), 2.79-2.74 (m, 1H), 1.84 (s, 3H); $^{13}$C NMR (100 MHz, CD$_3$OD) δ 173.53, 142.19, 129.98, 129.49, 127.20, 81.03, 80.96, 69.87, 69.36, 60.95, 49.70, 39.41, 35.88, 22.89. MS, (ES, m/z) [M+H]$^+$ 309.19.

N-(((2R,3R,4R,5R)-3,4-dihydroxy-5-(hydroxymethyl)-1-propylpyrrolidin-2-yl)methyl)acetamide

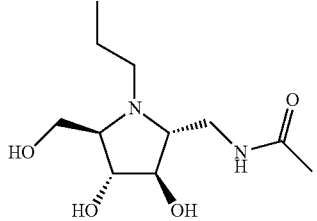 [SMILES: CCCN1[C@H](CO)[C@@H](O)[C@H](O)[C@H]1CNC(C)=O]

N-(((2R,3R,4R,5R)-3,4-dihydroxy-5-(hydroxymethyl)-1-propylpyrrolidin-2-yl)methyl)acetamide was prepared using the general procedure for reductive amination, using propanal. Colorless oil. Yield 53%. $^1$H NMR (500 MHz, CD$_3$OD) δ 3.97-3.96 (m, 1H), 3.78-3.74 (m, 1H), 3.76 (dd, J=5.1, 11.4 Hz, 1H), 3.68 (dd, J=3.4, 11.4 Hz, 1H), 3.50 (dd, J=3.3, 13.7 Hz, 1H), 3.19 (dd, J=7.0, 13.7 Hz, 1H), 3.05-3.01 (m, 2H), 2.77-2.72 (m, 1H), 2.64-2.58 (m, 1H), 1.95 (s, 3H), 1.65-1.57 (m, 1H), 1.56-1.48 (m, 1H), 0.94 (t, J=7.4 Hz, 3H); $^{13}$C NMR (125 MHz, CD$_3$OD) δ 173.70, 81.21, 80.99, 70.36, 69.37, 60.69, 50.08, 39.43, 22.78, 22.50, 12.35. MS, (ES, m/z) [M+H]$^+$ 247.17.

109

N-(((2R,3R,4R,5R)-1-butyl-3,4-dihydroxy-5-(hydroxymethyl)pyrrolidin-2-yl)methyl)acetamide

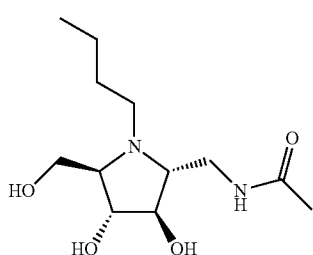 [SMILES: CCCCN1[C@H](CO)[C@@H](O)[C@H](O)[C@H]1CNC(C)=O]

N-(((2R,3R,4R,5R)-1-butyl-3,4-dihydroxy-5-(hydroxymethyl)pyrrolidin-2-yl)methyl)acetamide was prepared using the general procedure for reductive amination, using butanal. Colorless oil. Yield 70%. $^1$H NMR (500 MHz, CD$_3$OD) δ 3.99-3.98 (m, 1H), 3.82-3.81 (m, 1H), 3.78 (dd, J=4.9, 11.5 Hz, 1H), 3.71 (dd, J=3.7, 11.5 Hz, 1H), 3.51 (dd, J=3.5, 13.8 Hz, 1H), 3.26 (dd, J=6.8, 13.8 Hz, 1H), 3.14-3.08 (m, 2H), 2.84-2.77 (m, 2H), 1.96 (s, 3H), 1.59-1.54 (m, 2H), 1.43-1.36 (m, 2H), 0.95 (t, J=7.4 Hz, 3H); $^{13}$C NMR (125 MHz, CD$_3$OD) δ 173.90, 80.90, 80.68, 70.79, 69.80, 60.57, 48.28, 39.38, 31.21, 22.76, 21.66, 14.43. MS, (ES, m/z) [M+H]$^+$ 261.17.

N-(((2R,3R,4R,5R)-1-hexyl-3,4-dihydroxy-5-(hydroxymethyl)pyrrolidin-2-yl)methyl)acetamide

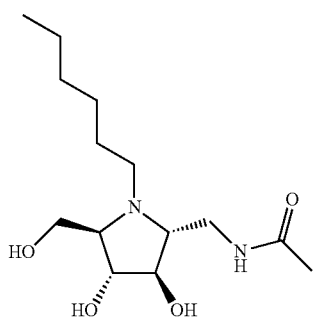 [SMILES: CCCCCCN1[C@H](CO)[C@@H](O)[C@H](O)[C@H]1CNC(C)=O]

N-(((2R,3R,4R,5R)-1-hexyl-3,4-dihydroxy-5-(hydroxymethyl)pyrrolidin-2-yl)methyl)acetamide was prepared using the general procedure for reductive amination, using hexanal. Colorless oil. Yield 73%. $^1$H NMR (500 MHz, CD$_3$OD) δ 3.98-3.97 (m, 1H), 3.82-3.81 (m, 1H), 3.78 (dd, J=4.9, 11.6 Hz, 1H), 3.71 (dd, J=3.8, 11.6 Hz, 1H), 3.51 (dd, J=3.6, 13.8 Hz, 1H), 3.26 (dd, J=6.8, 13.8 Hz, 1H), 3.14-3.09 (m, 2H), 2.84-2.75 (m, 2H), 1.95 (s, 3H), 1.62-1.55 (m, 2H), 1.38-1.28 (m, 6H), 0.91 (t, J=7.3 Hz, 3H); $^{13}$C NMR (125 MHz, CD$_3$OD) δ 173.93, 80.83, 80.62, 70.85, 69.88, 60.53, 48.63, 39.38, 32.99, 28.97, 28.26, 23.87, 22.76, 14.54. MS, (ES, m/z) [M+H]$^+$ 289.21.

110

EXAMPLES

Example 1

N-(((2R,3R,4R,5R)-3,4-dihydroxy-5-(hydroxymethyl)-1-(3-phenylpropyl)pyrrolidin-2-yl)methyl)acetamide

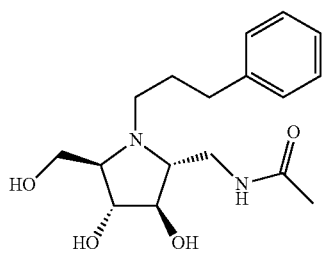 [SMILES: CC(=O)NC[C@@H]1[C@@H](O)[C@H](O)[C@@H](CO)N1CCCc1ccccc1]

N-(((2R,3R,4R,5R)-3,4-dihydroxy-5-(hydroxymethyl)-1-(3-phenylpropyl)pyrrolidin-2-yl)methyl)acetamide was prepared using the general procedure for reductive amination, using hydrocinnamaldehyde. Very pale yellow oil. Yield 50%. $^1$H NMR (400 MHz, CD$_3$OD) δ 7.26-7.20 (m, 4H), 7.16-7.13 (m, 1H), 3.98-3.97 (m, 1H), 3.79-3.78 (m, 1H), 3.73 (dd, J=5.0, 11.3 Hz, 1H), 3.65 (dd, J=3.3, 11.3 Hz, 1H), 3.48 (dd, J=3.5, 13.6 Hz, 1H), 3.17 (dd, J=7.0, 13.6 Hz, 1H), 3.07-3.01 (m, 2H), 2.80-2.76 (m, 1H), 2.74-2.64 (m, 2H), 2.64-2.58 (m, 1H), 1.94 (s, 3H), 1.92-1.84 (m, 2H); $^{13}$C NMR (100 MHz, CD$_3$OD) δ 173.65, 143.71, 129.57, 129.46, 126.88, 81.26, 81.08, 70.48, 69.44, 60.82, 47.59, 39.59, 34.70, 31.25, 22.81. MS, (ES, m/z) [M+H]$^+$ 323.21.

Example 2

N-(((2R,3R,4R,5R)-3,4-dihydroxy-5-(hydroxymethyl)-1-(3-(4-methoxyphenyl)propyl)pyrrolidin-2-yl)methyl)acetamide

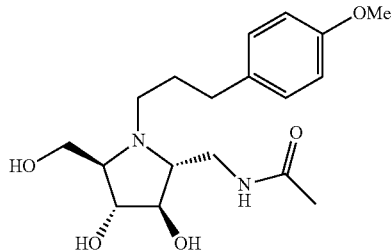 [SMILES: COc1ccc(CCCN2[C@H](CO)[C@@H](O)[C@H](O)[C@H]2CNC(C)=O)cc1]

N-(((2R,3R,4R,5R)-3,4-dihydroxy-5-(hydroxymethyl)-1-(3-(4-methoxyphenyl)propyl)pyrrolidin-2-yl)methyl)acetamide was prepared using the general procedure for reductive amination, using 3-(4-methoxyphenyl)propionaldehyde. Colorless oil. Yield 48%. $^1$H NMR (500 MHz, CD$_3$OD) δ 7.13-7.11 (m, 2H), 6.82-6.80 (m, 2H), 3.98-3.97 (m, 1H), 3.79-3.78 (m, 1H), 3.75 (s, 3H), 3.72 (dd, J=5.1, 11.3 Hz, 1H), 3.65 (dd, J=3.3, 11.3 Hz, 1H), 3.48 (dd, J=3.2, 13.6 Hz, 1H), 3.15 (dd, J=7.0, 13.6 Hz, 1H), 3.05-3.00 (m, 2H), 2.78-2.73 (m, 1H), 2.70-2.62 (m, 2H), 2.57-2.51 (m, 1H), 1.95 (s, 3H), 1.88-1.79 (m, 2H); $^{13}$C NMR (125 MHz, CD$_3$OD) δ 173.66, 159.39, 135.61, 130.46, 114.82, 81.23, 81.04, 70.39, 69.34, 60.74, 55.72, 47.51, 39.48, 33.75, 31.36, 22.80. MS, (ES, m/z) [M+H]+ 353.21.

Example 3

N-(((2R,3R,4R,5R)-1-(3-([1,1'-biphenyl]-4-yl)propyl)-3,4-dihydroxy-5-(hydroxymethyl)pyrrolidin-2-yl)methyl)acetamide

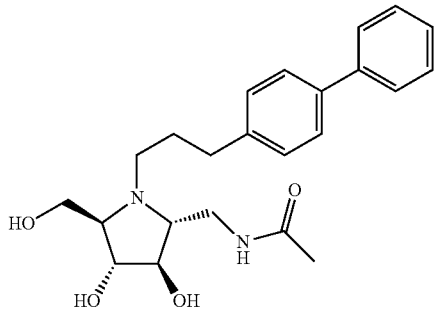 [SMILES: CC(=O)NC[C@@H]1[C@@H](O)[C@H](O)[C@@H](CO)N1CCCc1ccc(-c2ccccc2)cc1]

To a solution of [1,1'-biphenyl]-4-carbaldehyde (1.82 g, 10.0 mmol) and (carbomethoxymethyl)-triphenylphosphonium bromide (8.30 g, 20.0 mmol) in DCM (100 mL) and water (80 mL) was added NaOH (2 N, 10 mL, 20 mmol). After the mixture was stirred at room temperature for 3 h, the organic layer was collected and the aqueous was extracted with DCM (2×30 mL). The combined extract was dried over anhydrous Na₂SO₄. After filtration the solvent was evaporated under reduced pressure, and the residue was purified on silica gel by automatic flash column chromatography (DCM/hexanes, 1:2 to 2:1) to afford (E)-methyl 3-([1,1'-biphenyl]-4-yl)acrylate as a white solid (2.00 g, 84%). ¹H NMR (500 MHz, CDCl₃) δ 7.74 (d, J=16.0 Hz, 1H), 7.64-7.59 (m, 6H), 7.48-7.44 (m, 2H), 7.40-7.36 (m, 1H), 6.48 (d, J=16.0 Hz, 1H), 3.83 (s, 3H).

A suspension of (E)-methyl 3-([1,1'-biphenyl]-4-yl)acrylate (2.00 g, 8.39 mmol) and Pd(OH)₂/C (20% in Pd, 0.40 g, 0.75 mmol) in dry methanol (100 mL) was stirred under an atmosphere of hydrogen for 3 h. The suspension was then filtered through a celite cake, and the filtrate was concentrated under reduced pressure to give pure methyl 3-([1,1'-biphenyl]-4-yl)propanoate as a white solid (2.01 g, 100%). ¹H NMR (500 MHz, CDCl₃) δ 7.61-7.59 (m, 2H), 7.56-7.54 (m, 2H), 7.47-7.44 (m, 2H), 7.38-7.36 (m, 1H), 7.31-7.29 (m, 2H), 3.72 (s, 3H), 3.03 (t, J=7.8 Hz, 2H), 2.71 (t, J=7.8 Hz, 2H).

At 0° C., under argon, to solution of methyl 3-([1,1'-biphenyl]-4-yl)propanoate (2.00 g, 8.33 mmol) in dry THF (100 mL) was added lithium aluminum hydride (LAH) (0.38 g, 10 mmol). After the mixture was stirred at 0° C. for 2 h NaOH (5 N, 2 mL) was added to quench the reaction and the resulted suspension was stirred at room temperature for 1 h. The suspension was dried over anhydrous Na₂SO₄, then filtered through a celite cake. The filtrate was concentrated under reduced pressure to give pure 3-([1,1'-biphenyl]-4-yl)propan-1-ol as a white solid (1.76 g, 100%). ¹H NMR (500 MHz, CDCl₃) δ 7.60-7.58 (m, 2H), 7.54-7.52 (m, 2H), 7.44-7.41 (m, 2H), 7.35-7.31 (m, 1H), 7.29-7.27 (m, 2H), 3.72 (t, J=6.4 Hz, 2H), 2.76 (t, J=7.7 Hz, 2H), 1.97-1.91 (m, 2H).

A suspension of 3-([1,1'-biphenyl]-4-yl)propan-1-ol (1.76 g, 8.30 mmol) and Dess-Martin periodinane (5.30 g, 12.5 mmol) in DCM (80 mL) was stirred at room temperature for 1 h. Diethyl ether (200 mL) was added, and the resulted white solid was filtered off through a celite cake. The organic filtrate was washed with mixed saturated NaHCO₃ and Na₂S₂O₃ (40/5 mL), and then was dried over anhydrous Na₂SO₄. After filtration the solvent was evaporated under reduced pressure, and the residue was purified on silica gel by automatic flash column chromatography (EtOAc/hexanes, 1:9 to 1:5) to afford 3-([1,1'-biphenyl]-4-yl)propanal as a pale yellow solid (1.40 g, 80%). ¹H NMR (500 MHz, CDCl₃) δ 9.86 (t, J=1.2 Hz, 1H), 7.74-7.56 (m, 2H), 7.54-7.52 (m, 2H), 7.45-7.41 (m, 2H), 7.35-7.32 (m, 1H), 7.28-7.26 (m, 2H), 3.01 (t, J=7.6 Hz, 2H), 2.82 (dt, J=1.2, 7.6 Hz, 2H).

N-(((2R,3R,4R,5R)-1-(3-([1,1-biphenyl]-4-yl)propyl)-3,4-dihydroxy-5-(hydroxymethyl)pyrrolidin-2-yl)methyl)acetamide was prepared using the general procedure for reductive amination, using 3-([1,1'-biphenyl]-4-yl)propanal. Off-white solid. Yield 84%. ¹H NMR (500 MHz, CD₃OD) δ 7.59-7.56 (m, 2H), 7.53-7.51 (m, 2H), 7.42-7.39 (m, 2H), 7.31-7.28 (m, 3H), 3.99-3.97 (m, 1H), 3.80-3.78 (m, 1H), 3.75 (dd, J=5.1, 11.3 Hz, 1H), 3.67 (dd, J=3.3, 11.3 Hz, 1H), 3.50 (dd, J=3.8, 13.7 Hz, 1H), 3.18 (dd, J=6.5, 13.7 Hz, 1H), 3.08-3.05 (m, 2H), 2.85-2.63 (m, 4H), 1.95 (s, 3H), 1.95-1.86 (m, 2H); ¹³C NMR (125 MHz, CDCl₃+CD₃OD) δ 172.32, 141.00, 140.98, 138.93, 128.79, 128.78, 127.14, 127.12, 126.97, 79.67, 79.32, 69.22, 68.68, 59.68, 46.50, 38.63, 33.11, 29.80, 22.70. MS, (ES, m/z) [M+H]+ 399.23.

Example 4

N-(((2R,3R,4R,5R)-1-(2-([1,1'-biphenyl]-4-yl)ethyl)-3,4-dihydroxy-5-(hydroxymethyl)pyrrolidin-2-yl)methyl)acetamide

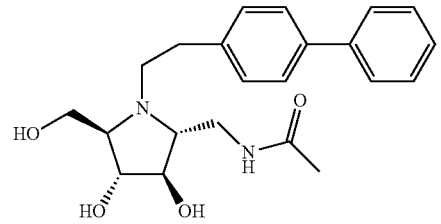 [SMILES: CC(=O)NC[C@@H]1[C@@H](O)[C@H](O)[C@@H](CO)N1CCc1ccc(-c2ccccc2)cc1]

N-(((2R,3R,4R,5R)-1-(2-([1,1-biphenyl]-4-yl)ethyl)-3,4-dihydroxy-5-(hydroxymethyl)pyrrolidin-2-yl)methyl)acetamide was prepared using the general procedure for reductive amination, using 2-([1,1'-biphenyl]-4-yl)acetaldehyde which was obtained using a literature procedure (*J. Med. Chem.* 2009, 52(9), 2776-2785). White solid. Yield 58%. ¹H NMR (500 MHz, CD₃OD) δ 7.60-7.57 (m, 2H), 7.56-7.53 (m, 2H), 7.43-7.39 (m, 2H), 7.36-7.33 (m, 2H), 7.30-7.31 (m, 1H), 3.99-3.98 (m, 1H), 3.87 (dd, J=4.6, 11.6 Hz, 1H), 3.76 (dd, J=3.6, 11.6 Hz, 1H), 3.76-3.74 (m, 1H), 3.56-3.52 (m, 1H), 3.24-3.22 (m, 1H), 3.17-3.11 (m, 3H), 2.98-2.92 (m, 2H), 2.87-2.83 (m, 1H), 1.80 (s, 3H); ¹³C NMR (125 MHz, CD₃OD) δ 173.72, 142.37, 141.03, 140.46, 130.52, 129.98, 128.29, 128.09, 127.92, 80.75, 80.72, 70.15, 69.69, 60.80, 49.78, 39.29, 35.16, 22.82. MS, (ES, m/z) [M+H]+ 385.22.

Example 5

N-(((2R,3R,4R,5R)-3,4-dihydroxy-5-(hydroxymethyl)-1-(4-phenylbutyl)pyrrolidin-2-yl)methyl)acetamide

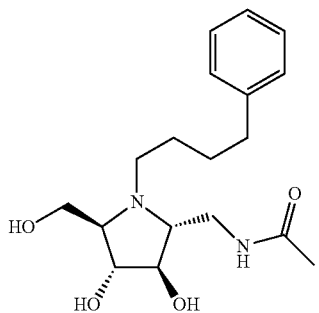 [SMILES: CC(=O)NC[C@@H]1[C@@H](O)[C@H](O)[C@@H](CO)N1CCCCc1ccccc1]

N-(((2R,3R,4R,5R)-3,4-dihydroxy-5-(hydroxymethyl)-1-(4-phenylbutyl)pyrrolidin-2-yl)methyl)acetamide was prepared using the general procedure for reductive amination, using 4-phenylbutanal which was obtained using a literature procedure (*J. Am. Chem. Soc.* 1996, 118(3), 502-508). Pale yellow oil. Yield 72%. $^1$H NMR (500 MHz, CD$_3$OD) δ 7.25-7.22 (m, 2H), 7.20-7.17 (m, 2H), 7.15-7.12 (m, 1H), 3.98-3.97 (m, 1H), 3.80-3.79 (m, 1H), 3.76 (dd, J=4.9, 11.5 Hz, 1H), 3.68 (dd, J=3.6, 11.5 Hz, 1H), 3.49 (dd, J=3.4, 13.5 Hz, 1H), 3.23 (dd, J=6.7, 13.8 Hz, 1H), 3.10-3.05 (m, 2H), 2.85-2.82 (m, 1H), 2.77-2.73 (m, 1H), 2.66-2.61 (m, 2H), 1.92 (s, 3H), 1.72-1.58 (m, 3H); $^{13}$C NMR (125 MHz, CD$_3$OD) δ 173.81, 143.86, 129.55, 129.43, 126.85, 81.00, 80.75, 70.53, 69.73, 60.62, 48.10, 39.53, 36.80, 30.50, 28.73, 22.78. MS, (ES, m/z) [M+H]$^+$ 337.21.

Example 6

N-(((2R,3R,4R,5R)-1-(3,3-diphenylpropyl)-3,4-dihydroxy-5-(hydroxymethyl)pyrrolidin-2-yl)methyl)acetamide

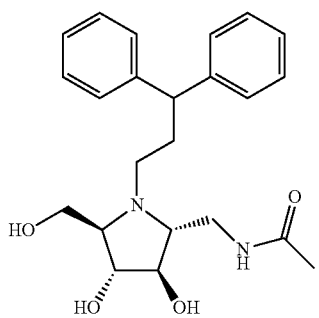 [SMILES: CC(=O)NC[C@@H]1[C@@H](O)[C@H](O)[C@@H](CO)N1CCC(c1ccccc1)c1ccccc1]

N-(((2R,3R,4R,5R)-1-(3,3-diphenylpropyl)-3,4-dihydroxy-5-(hydroxymethyl)pyrrolidin-2-yl)methyl)acetamide was prepared using the general procedure for reductive amination, using 3,3-diphenylpropanal. $^1$H NMR (500 MHz, CD$_3$OD) δ 7.36-7.24 (m, 8H), 7.20-7.17 (m, 2H), 4.13-4.07 (m, 1H), 4.02-3.98 (br, 1H), 3.84-3.80 (br, 1H), 3.71-3.61 (m, 2H), 3.48-3.40 (m, 1H), 3.35-3.32 (m, 1H), 3.12-3.04 (m, 3H), 2.81-2.74 (m, 1H), 2.71-2.63 (m, 1H), 2.50-2.40 (m, 1H), 2.32-2.23 (m, 1H), 1.96 (s, 3H); $^{13}$C NMR (125 MHz, CD$_3$OD) δ 172.2, 145.3, 144.5, 128.1, 128.0, 127.6, 127.4, 125.9, 125.7, 79.5, 79.4, 69.2, 68.1, 59.2, 48.8, 45.2, 37.9, 33.5, 21.3; MS (ES, m/z) [M+H]$^+$ 399.2.

Example 7

N-(((2R,3R,4R,5R)-3,4-dihydroxy-5-(hydroxymethyl)-1-(pyridin-3-ylmethyl)pyrrolidin-2-yl)methyl)acetamide

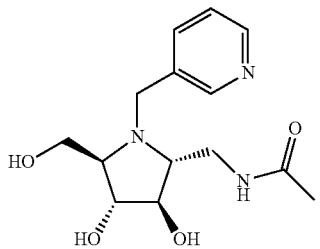 [SMILES: CC(=O)NC[C@@H]1[C@@H](O)[C@H](O)[C@@H](CO)N1Cc1cccnc1]

N-(((2R,3R,4R,5R)-3,4-dihydroxy-5-(hydroxymethyl)-1-(pyridin-3-ylmethyl)pyrrolidin-2-yl)methyl)acetamide was prepared using the general procedure for reductive amination using 3-pyridinecarboxaldehyde. Colorless oil. Yield 60%. $^1$H NMR (500 MHz, CD$_3$OD) δ 8.57 (s, 1H), 8.40 (d, J=4.9 Hz, 1H), 7.92 (d, J=7.8 Hz, 1H), 7.40 (dd, J=4.9, 7.8 Hz, 1H), 4.07-3.99 (m, 3H), 3.85-3.83 (m, 1H), 3.73 (dd, J=4.6, 11.5 Hz, 1H), 3.66 (dd, J=3.4, 11.5 Hz, 1H), 3.44 (dd, J=3.4, 13.9 Hz, 1H), 3.33-3.29 (m, 1H), 3.10-3.07 (m, 1H), 2.99-2.97 (m, 1H), 1.93 (s, 3H); $^{13}$C NMR (125 MHz, CD$_3$OD) δ 173.59, 150.05, 148.63, 138.40, 137.87, 125.25, 81.18, 80.77, 70.02, 69.65, 61.36, 49.56, 40.28, 22.80. MS, (ES, m/z) [M+H]$^+$ 296.16.

Example 8

N-(((2R,3R,4R,5R)-3,4-dihydroxy-5-(hydroxymethyl)-1-(pyridin-2-ylmethyl)pyrrolidin-2-yl)methyl)acetamide

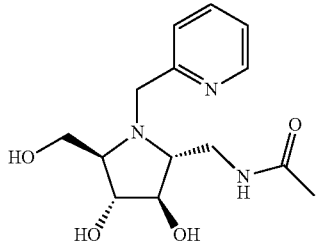 [SMILES: CC(=O)NC[C@@H]1[C@@H](O)[C@H](O)[C@@H](CO)N1Cc1ccccn1]

N-(((2R,3R,4R,5R)-3,4-dihydroxy-5-(hydroxymethyl)-1-(pyridin-2-ylmethyl)pyrrolidin-2-yl)methyl)acetamide was prepared using the general procedure for reductive amination using 2-pyridinecarboxaldehyde. Pale yellow oil. Yield 35%. $^1$H NMR (500 MHz, CD$_3$OD) δ 8.50-8.49 (m, 1H), 7.82 (dt, J=1.7, 7.7 Hz, 1H), 7.57 (d, J=7.7 Hz, 1H), 7.33-7.30 (m, 1H), 4.14-4.08 (m, 2H), 4.01 (t, J=3.2 Hz, 1H), 3.81 (t, J=3.2 Hz, 1H), 3.74 (dd, J=4.4, 11.7 Hz, 1H), 3.64 (dd, J=3.2, 11.7 Hz, 1H), 3.53 (dd, J=3.2, 14.0 Hz, 1H), 3.24 (dd, J=5.8, 14.0 Hz, 1H), 3.11-3.09 (m, 1H), 3.04-3.02 (m, 1H), 1.94 (s, 3H). MS, (ES, m/z) [M+H]$^+$ 296.16.

Example 9

N-(((2R,3R,4R,5R)-1-([1,1'-biphenyl]-4-ylmethyl)-3,4-dihydroxy-5-(hydroxymethyl)pyrrolidin-2-yl)methyl)acetamide

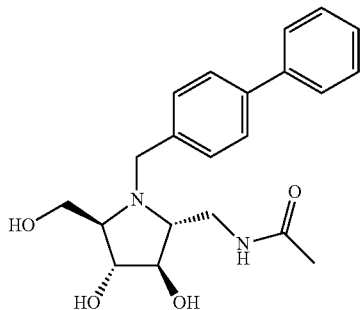 [SMILES: CC(=O)NC[C@@H]1[C@@H](O)[C@H](O)[C@@H](CO)N1Cc1ccc(-c2ccccc2)cc1]

N-(((2R,3R,4R,5R)-1-([1,1'-biphenyl]-4-ylmethyl)-3,4-dihydroxy-5-(hydroxymethyl)pyrrolidin-2-yl)methyl)acetamide was prepared using the general procedure for reductive amination using [1,1'-biphenyl]-4-carbaldehyde. Off-white solid. Yield 90%. $^1$H NMR (500 MHz, CD$_3$OD) δ 7.59-7.55 (m, 4H), 7.49-7.47 (m, 2H), 7.42-7.39 (m, 2H), 7.32-7.29 (m, 1H), 4.04-4.03 (m, 1H), 4.01-3.95 (m, 2H), 3.85-3.84 (m, 1H), 3.79 (dd, J=4.9, 11.4 Hz, 1H), 3.66 (dd, J=3.1, 11.4 Hz, 1H), 3.44 (dd, J=3.4, 13.8 Hz, 1H), 3.32 (dd, J=6.1, 13.8 Hz, 1H), 3.15-3.13 (m, 1H), 3.07-3.05 (m, 1H), 1.93 (s, 3H); $^{13}$C NMR (125 MHz, CD$_3$OD) δ 173.61, 142.40, 141.28, 140.20, 129.95, 129.93, 128.32, 128.06, 127.99, 81.34, 80.88, 70.06, 69.80, 61.23, 52.09, 40.38, 22.84. MS, (ES, m/z) [M+H]$^+$ 371.20.

Example 10

2-((2R,3R,4R,5R)-3,4-dihydroxy-5-(hydroxymethyl)-1-(3-phenylpropyl)pyrrolidin-2-yl)-N-methylacetamide

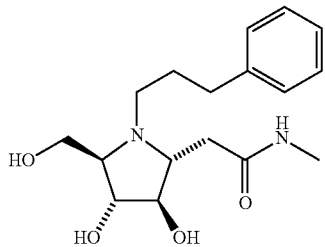 [SMILES: CNC(=O)C[C@@H]1[C@@H](O)[C@H](O)[C@@H](CO)N1CCCc1ccccc1]

At 0° C., to a solution of (2R,3R,4R)-3,4-bis(benzyloxy)-2-((benzyloxy)methyl)-3,4-dihydro-2H-pyrrole 1-oxide (*Tetrahedron* 2009, 65, 93-100) (5.80 g, 13.9 mmol) in THF (60 mL) was added allylmagnesium chloride (2 M, THF, 8.5 mL, 17 mmol). After the mixture was stirred at room temperature for 16 h saturated aqueous NH$_4$Cl (50 mL) was added and the mixture was extracted with EtOAc (2×50 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 1:9 to 1:3) to afford (2R,3R,4R,5R)-2-allyl-3,4-bis(benzyloxy)-5-((benzyloxy)methyl)pyrrolidin-1-ol as a pale yellow oil (4.80 g, 75%). $^1$H NMR (500 MHz, CDCl$_3$) δ 7.37-7.28 (m, 15H), 5.90-5.80 (m, 1H), 5.14-5.08 (m, 2H), 4.61-4.40 (m, 6H), 3.99-3.97 (m, 1H), 3.88-3.86 (m, 1H), 3.81-3.74 (m, 1H), 3.69-3.65 (m, 1H), 3.58-3.55 (m, 1H), 3.42-3.38 (m, 1H), 2.74-2.69 (m, 1H), 2.36-2.30 (m, 1H). MS, (ES, m/z) [M+H]$^+$ 460.2.

A suspension of (2R,3R,4R,5R)-2-allyl-3,4-bis(benzyloxy)-5-((benzyloxy)methyl)pyrrolidin-1-ol (5.89 g, 12.8 mmol), Zn powder (2.20 g, 34.7 mmol) in AcOH/MeOH (9 mL/100 mL) was stirred at reflux for 1 h. After being cooled to room temperature, the suspension was filtered thought a celite cake and concentrated. The residue was treated with saturated aqueous NaHCO$_3$ (80 mL), and the extracted with DCM (3×80 mL). The combined filtrate was dried over anhydrous Na$_2$SO$_4$. After filtration the solvent was evaporated under reduced pressure, and the residue was dissolved in DCM (100 mL). To the solution was added Boc$_2$O (4.36 g, 20.0 mmol) and DIPEA (2.0 mL), and the mixture was stirred at room temperature for 16 h. After concentration the residue was purified on silica gel by automatic flash column chromatography (EtOAc/hexanes, 1:20 to 1:5) to afford (2R,3R,4R,5R)-tert-butyl 2-allyl-3,4-bis(benzyloxy)-5-((benzyloxy)methyl)pyrrolidine-1-carboxylate as a colorless oil (5.90 g, 85%). This compound exists as two conformational rotamers in CDCl$_3$ and gives a complicated $^1$H NMR pattern. MS, (ES, m/z) [M+H]$^+$ 544.3.

To a solution of (2R,3R,4R,5R)-tert-butyl 2-allyl-3,4-bis(benzyloxy)-5-((benzyloxy)methyl)pyrrolidine-1-carboxylate (5.70 g, 10.5 mmol) and 4-methyl morpholine-N-oxide (2.46 g, 21.0 mmol) in acetone/H$_2$O (60 mL/10 mL) was added OsO$_4$ (4% in water, 0.60 mL, 24 mg, 0.094 mmol). After the mixture was stirred at room temperature for 16 h a solution of Na$_2$S$_2$O$_3$ (5 g) in water (10 mL) was added. After stirring at room temperature for 20 min the mixture was concentrated and extracted with DCM (3×100 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 1:2 to 2:1) to afford (2R,3R,4R,5R)-tert-butyl 3,4-bis(benzyloxy)-2-((benzyloxy)methyl)-5-(2,3-dihydroxypropyl)pyrrolidine-1-carboxylate as a pale yellow oil (6.02 g, 99%). This compound exists as two conformational rotamers in CDCl$_3$ and gives a complicated $^1$H NMR pattern. MS, (ES, m/z) [M+H]$^+$ 578.3.

To a suspension of (2R,3R,4R,5R)-tert-butyl 3,4-bis(benzyloxy)-2-((benzyloxy)methyl)-5-(2,3-dihydroxypropyl)pyrrolidine-1-carboxylate (5.54 g, 10.2 mmol) in THF (60 mL) and an aqueous NaH$_2$PO$_4$/NaHCO$_3$ buffer solution (1:1 molar ratio, 60 mL) was added NaIO$_4$ (3.46 g, 16.2 mmol), and the mixture was stirred at room temperature for 3 h. The mixture was then diluted with brine (100 mL) and extracted with EtOAc (3×80 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 1:10 to 1:3) to afford (2R,3R,4R,5R)-tert-butyl 3,4-bis(benzyloxy)-2-((benzyloxy)methyl)-5-(2-oxoethyl)pyrrolidine-1-carboxylate as a colorless oil (5.10 g, 92%). This compound exists as two conformational rotamers in CDCl$_3$ and gives a complicated $^1$H NMR pattern. MS, (ES, m/z) [M+H]$^+$ 546.3.

To a solution of (2R,3R,4R,5R)-tert-butyl 3,4-bis(benzyloxy)-2-((benzyloxy)methyl)-5-(2-oxoethyl)pyrrolidine-1-carboxylate (5.01 g, 9.18 mmol), 2-methylbut-2-ene (3.2 g, 46 mmol) in mixed tert-butanol/CDCl$_3$ (12 mL/75 mL) was added a solution of NaH$_2$PO$_4$ (4.0 g, 33 mmol) in water (7 mL) and NaClO$_2$ (1.56 g, 17.2 mmol). After the mixture was stirred at room temperature for 3 h a solution of Na$_2$S$_2$O$_3$ (5 g) in water (10 mL) was added. After stirring at room temperature for 10 min the mixture was adjusted to weakly acidic (pH=~3) with 1 N HCl, and then extracted with DCM (3×50 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 1:4 to 1:2) to afford 2-((2R,3R,4R,5R)-3,4-bis(benzyloxy)-5-((benzyloxy)methyl)-1-(tert-butoxycarbonyl)pyrrolidin-2-yl)acetic acid as a colorless oil (5.02 g, 97%). This compound exists as two conformational rotamers in CDCl$_3$ and gives a complicated $^1$H NMR pattern. MS, (ES, m/z) [M+H]$^+$ 562.3.

A mixture of 2-((2R,3R,4R,5R)-3,4-bis(benzyloxy)-5-((benzyloxy)methyl)-1-(tert-butoxycarbonyl)pyrrolidin-2-yl)acetic acid (2.10 g, 3.74 mmol), MeNH$_2$ hydrochloride (0.54 g, 8.0 mmol), DIPEA (2.3 g, 18 mmol) and 2-(1H-7-azabenzotriazol-1-yl)-1,1,3,3-tetramethyl uronium hexafluorophosphate methanaminium (HATU) (1.90 g, 5.00 mmol) in DMF (20 mL) was stirred at room temperature for 2 days. The mixture was diluted with brine (100 mL) and extracted with Et$_2$O (3×50 mL). The combined filtrate was washed with saturated aqueous NaHCO$_3$ (50 mL), and dried over anhydrous Na$_2$SO$_4$. After filtration the solvent was evaporated under reduced pressure, and the residue was purified on silica gel by automatic flash column chromatography (EtOAc/hexanes, 1:2 to 1:1) to afford (2R,3R,4R,5R)-tert-butyl 3,4-bis(benzyloxy)-2-((benzyloxy)methyl)-5-(2-(methylamino)-2-oxoethyl)pyrrolidine-1-carboxylate as a colorless oil (2.15 g, 100%). This compound exists as two conformational rotamers in CDCl$_3$ and gives a complicated $^1$H NMR pattern. MS, (ES, m/z) [M+H]$^+$ 575.3.

To a solution of (2R,3R,4R,5R)-tert-butyl 3,4-bis(benzyloxy)-2-((benzyloxy)methyl)-5-(2-(methylamino)-2-oxoethyl)pyrrolidine-1-carboxylate (2.15 g, 3.74 mmol) in mixed methanol/EtOAc (40 mL/20 mL) was bubbled with HCl gas for 30 seconds. After stirring for 2 h the mixture was concentrated. The residue was treated with saturated aqueous NaHCO$_3$ (40 mL), and extracted with DCM (3×50 mL). The combined filtrate was dried over anhydrous Na$_2$SO$_4$. After filtration the solvent was evaporated under reduced pressure to afford pure 2-((2R,3R,4R,5R)-3,4-bis(benzyloxy)-5-((benzyloxy)methyl)pyrrolidin-2-yl)-N-methylacetamide as a colorless oil (1.70 g, 96%). $^1$H NMR (500 MHz, CDCl$_3$) δ 7.34-7.25 (m, 15H), 4.52-4.50 (m, 6H), 3.91-3.89 (m, 1H), 3.78-3.76 (m, 1H), 3.56-3.53 (m, 3H), 3.48 (s, 1H), 3.41-3.38 (m, 1H), 2.74 (d, J=4.8 Hz, 3H), 2.51 (dd, J=9.4, 15.7, 1H), 2.40 (dd, J=4.3, 15.7, 1H.

To a solution of 2-((2R,3R,4R,5R)-3,4-bis(benzyloxy)-5-((benzyloxy)methyl)pyrrolidin-2-yl)-N-methylacetamide (1.40 g, 2.95 mmol) in DCM (100 mL) at −78° C. was added BCl$_3$ (1.0 M, 17.7 mL, 17.7 mmol), and the solution was stirred at room temperature for 16 h. After cooling at −78° C. the solution was quenched with MeOH. After concentration under reduced pressure the residue (2-((2R,3R,4R,5R)-3,4-dihydroxy-5-(hydroxymethyl)pyrrolidin-2-yl)-N-methylacetamide) as an impure HCl salt (0.87 g) was obtained. The residue (0.30 g) was dissolved in MeOH (10 mL), and to which hydrocinnamaldehyde (0.334 g, 2.50 mmol), NaBH$_3$CN (0.20 g, 3.0 mmol) was added. The mixture was stirred at room temperature for 16 h, and then concentrated under reduced pressure. The residue was purified on silica gel by flash column chromatography (EtOAc; then MeOH/DCM, 1:5) to afford 2-((2R,3R,4R,5R)-3,4-dihydroxy-5-(hydroxymethyl)-1-(3-phenylpropyl)pyrrolidin-2-yl)-N-methylacetamide as a white foam (0.310 g, 94%). $^1$H NMR (500 MHz, CD$_3$OD) δ 7.26-7.23 (m, 2H), 7.22-7.20 (m, 2H), 7.16-7.13 (m, 1H), 3.96-3.95 (m, 1H), 3.80-3.79 (m, 1H), 3.71-3.65 (m, 2H), 3.41-3.39 (m, 1H), 2.89-2.87 (m, 1H), 2.73-2.65 (m, 6H), 2.61-2.56 (m, 1H), 2.47 (dd, J=4.9, 14.7 Hz, 1H), 2.36 (dd, J=8.2, 14.7 Hz, 1H), 1.88-1.80 (m, 2H); $^{13}$C NMR (125 MHz, CD$_3$OD) δ 175.06, 143.59, 129.58, 129.46, 126.92, 82.07, 81.10, 71.05, 66.81, 61.07, 47.77, 35.12, 34.71, 30.97, 26.45. MS, (ES, m/z) [M+H]$^+$ 323.2.

Example 11

2-((2R,3R,4R,5R)-3,4-dihydroxy-5-(hydroxymethyl)-1-(3-(4-methoxyphenyl)propyl)pyrrolidin-2-yl)-N-ethylacetamide

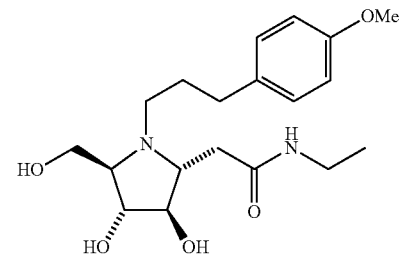 [SMILES: CCNC(=O)C[C@@H]1[C@@H](O)[C@H](O)[C@@H](CO)N1CCCc1ccc(OC)cc1]

2-((2R,3R,4R,5R)-3,4-dihydroxy-5-(hydroxymethyl)pyrrolidin-2-yl)-N-ethylacetamide was prepared from 2-((2R,3R,4R,5R)-3,4-bis(benzyloxy)-5-((benzyloxy)methyl)-1-(tert-butoxycarbonyl)pyrrolidin-2-yl)acetic acid using procedures analagous to those described for Example 10. 2-((2R,3R,4R,5R)-3,4-dihydroxy-5-(hydroxymethyl)pyrrolidin-2-yl)-N-ethylacetamide (50 mg, 0.2 mmol) was dissolved in MeOH (3 mL), to which 3-(4-methoxyphenyl)propionaldehyde (65 mg, 0.40 mmol) and NaBH$_3$CN (25 mg, 0.40 mmol) were added. The mixture was stirred at room temperature for 16 h, and then concentrated under reduced pressure. The residue was purified on silica gel by flash column chromatography to afford product as white foam (36 mg, 55%). $^1$H NMR (500 MHz, CD$_3$OD) δ 7.13 (d, J=9.0 Hz, 2H), 6.83 (d, J=9.0 Hz, 2H), 3.99-3.96 (br, 1H), 3.84-3.81 (br, 1H), 3.77 (s, 3H), 3.73-3.66 (m, 2H), 3.44-3.39 (m, 1H), 3.21 (q, J=7.0 Hz, 2H), 2.92-2.87 (m, 1H), 2.75-2.62 (m, 3H), 2.60-2.52 (m, 1H), 2.51-2.45 (m, 1H), 2.40-2.33 (m, 1H), 1.90-1.75 (m, 2H)), 1.13 (t, J=7.2 Hz, 3H); MS (ES, m/z) [M+H]$^+$ 367.2.

Example 12

2-((2R,3R,4R,5R)-1-(3,3-diphenylpropyl)-3,4-dihydroxy-5-(hydroxymethyl)pyrrolidin-2-yl)-N-ethylacetamide

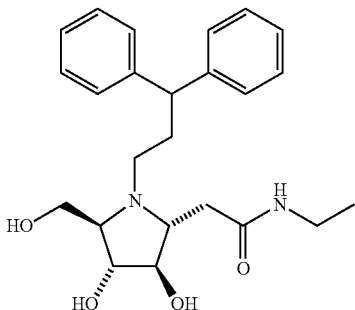 [SMILES: CCNC(=O)C[C@@H]1[C@@H](O)[C@H](O)[C@@H](CO)N1CCC(c1ccccc1)c1ccccc1]

2-((2R,3R,4R,5R)-1-(3,3-diphenylpropyl)-3,4-dihydroxy-5-(hydroxymethyl)pyrrolidin-2-yl)-N-ethylacetamide was prepared from 2-((2R,3R,4R,5R)-3,4-dihydroxy-5-(hydroxymethyl)pyrrolidin-2-yl)-N-ethylacetamide and 3,3-diphenylpropanal using procedures analogous to those described for Example 11. $^1$H NMR (500 MHz, CD$_3$OD) δ 7.35-7.24 (m, 8H), 7.18-7.13 (m, 2H), 4.08-4.03 (m, 1H), 3.99-3.96 (br, 1H), 3.84-3.78 (br, 1H), 3.63-3.55 (m, 2H), 3.47-3.42 (m, 1H), 3.35-3.32 (m, 1H), 3.24-3.12 (m, 2H), 2.86-2.82 (m, 1H), 2.65-2.58 (m, 2H), 2.43-2.33 (m, 2H), 2.32-2.20 (m, 2H), 1.11 (t, J=7.2 Hz, 3H); $^{13}$C NMR (125 MHz, CD$_3$OD) δ 172.7, 145.2, 144.7, 128.1, 128.0, 127.7, 127.4, 125.8, 125.7, 80.5, 79.6, 69.6, 65.1, 59.6, 48.9, 45.1, 33.8, 33.7, 33.5, 13.4; MS (ES, m/z) [M+H]$^+$ 413.2.

Example 13

2-((2R,3S,4R,5R)-3,4-dihydroxy-5-(hydroxymethyl)-1-(3-phenylpropyl)pyrrolidin-2-yl)-N-methylacetamide

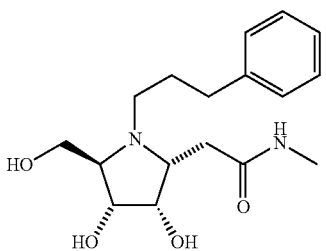 [SMILES: CNC(=O)C[C@@H]1[C@H](O)[C@H](O)[C@@H](CO)N1CCCc1ccccc1]

A suspension of (2R,3R,4R,5R)-tert-butyl 3,4-bis(benzyloxy)-2-((benzyloxy)methyl)-5-(2-(methylamino)-2-oxoethyl)pyrrolidine-1-carboxylate (1.35 g, 2.35 mmol) and Pd on carbon (10% Pd by weight, 0.320 g, 0.301 mmol) in MeOH (25 mL) was shaken at room temperature under hydrogen (40 psi) for 16 h. The suspension was then filtered through a celite cake, and the filtrate was concentrated to afford pure (2R,3R,4R,5R)-tert-butyl 3,4-dihydroxy-2-(hydroxymethyl)-5-(2-(methylamino)-2-oxoethyl)pyrrolidine-1-carboxylate as a white solid (0.72 g, 100%). This compound exists as two conformational rotamers in CD$_3$OD and gives a complicated $^1$H NMR pattern. MS, (ES, m/z) [M+H]$^+$ 305.2, [M+Na]$^+$ 327.2.

To a solution of (2R,3R,4R,5R)-tert-butyl 3,4-dihydroxy-2-(hydroxymethyl)-5-(2-(methylamino)-2-oxoethyl)pyrrolidine-1-carboxylate (0.300 g, 0.982 mmol) and imidazole (0.20 g, 3.0 mmol) in anhydrous pyridine (15 mL), at 0° C., was added 1,3-dichloro-1,1,3,3-tetraisopropyldisiloxane mixture (TIPDSCl) (0.370 g, 1.17 mmol), and the mixture was stirred at room temperature for 5 h. The mixture was diluted with brine (50 mL) and extracted with EtOAc (3×30 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 2:3 to 3:2) to afford (6aR,8R,9R,9aR)-tert-butyl 9-hydroxy-2,2,4,4-tetraisopropyl-8-(2-(methylamino)-2-oxoethyl)tetrahydro-[1,3,5,2,4]trioxadisilocino[7,6-b]pyrrole-7(8H)-carboxylate as a white solid (0.44 g, 82%). This compound exists as two conformational rotamers in CDCl$_3$ and gives a complicated $^1$H NMR pattern. MS, (ES, m/z) [M+H]$^+$ 547.3.

A mixture of (6aR,8R,9R,9aR)-tert-butyl 9-hydroxy-2,2,4,4-tetraisopropyl-8-(2-(methylamino)-2-oxoethyl)tetrahydro-[1,3,5,2,4]trioxadisilocino[7,6-b]pyrrole-7(8H)-carboxylate (0.440 g, 0.805 mmol) and Dess-Martin periodinane (DMP) (0.636 g, 1.50 mmol) in DCM (60 mL) was stirred at room temperature for 1 h. The mixture was diluted with Et$_2$O (60 mL) and filtered through a celite cake. The filtrate was concentrated and treated with saturated aqueous NaHCO$_3$ (20 mL). The mixture was extracted with EtOAc (2×20 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 1:2 to 1:1) to afford (6aR,8R,9aR)-tert-butyl 2,2,4,4-tetraisopropyl-8-(2-(methylamino)-2-oxoethyl)-9-oxotetrahydro-[1,3,5,2,4]trioxadisilocino[7,6-b]pyrrole-7(8H)-carboxylate as a white solid (0.35 g, 80%). This compound exists as two conformational rotamers in CDCl$_3$ and gives a complicated $^1$H NMR pattern. MS, (ES, m/z) [M+H]$^+$ 545.3.

To a solution of (6aR,8R,9aR)-tert-butyl 2,2,4,4-tetraisopropyl-8-(2-(methylamino)-2-oxoethyl)-9-oxotetrahydro-[1,3,5,2,4]trioxadisilocino[7,6-b]pyrrole-7(8H)-carboxylate (0.830 g, 1.52 mmol), at 0° C., was added NaBH$_4$ (0.114 g, 3.00 mmol), and the mixture was stirred at 0° C. for 20 min. The mixture was quenched with water and concentrated. The residue was diluted with saturated aqueous NaHCO$_3$ (20 mL) and extracted with DCM (3×40 mL). The combined filtrate was dried over anhydrous Na$_2$SO$_4$. After filtration the solvent was evaporated under reduced pressure, and the residue was purified on silica gel by automatic flash column chromatography (EtOAc/hexanes, 2:3 to 3:2) to afford (6aR,8R,9S,9aR)-tert-butyl 9-hydroxy-2,2,4,4-tetraisopropyl-8-(2-(methylamino)-2-oxoethyl)tetrahydro-[1,3,5,2,4]trioxadisilocino[7,6-b]pyrrole-7(8H)-carboxylate as a white solid (0.80 g, 95%). This compound exists as two conformational rotamers in CDCl$_3$ and gives a complicated $^1$H NMR pattern. MS, (ES, m/z) [M+H]$^+$ 547.3.

To a solution of (6aR,8R,9S,9aR)-tert-butyl 9-hydroxy-2,2,4,4-tetraisopropyl-8-(2-(methylamino)-2-oxoethyl)tetrahydro-[1,3,5,2,4]trioxadisilocino[7,6-b]pyrrole-7(8H)-carboxylate (0.590 g, 1.08 mmol), at 0° C., was added TBAF (1.0 M, 3.5 mL, 3.5 mmol), and the mixture was stirred at room temperature for 3 h. After concentration under reduced pressure the residue was purified on silica gel by automatic flash column chromatography (MeOH/EtOAc, 1:20 to 1:10)

to afford (2R,3R,4S,5R)-tert-butyl 3,4-dihydroxy-2-(hydroxymethyl)-5-(2-(methylamino)-2-oxoethyl)pyrrolidine-1-carboxylate as a white solid (0.300 g, 91%). This compound exists as two conformational rotamers in CD$_3$OD and gives a complicated $^1$H NMR pattern. MS, (ES, m/z) [M+H]$^+$ 306.2.

To a solution of (2R,3R,4S,5R)-tert-butyl 3,4-dihydroxy-2-(hydroxymethyl)-5-(2-(methylamino)-2-oxoethyl)pyrrolidine-1-carboxylate (0.190 g, 0.623 mmol) in methanol (10 mL) was bubbled with HCl gas for 30 seconds. After stirring for 2 h the mixture was concentrated and washed with DCM. The residue was dissolved in MeOH (3 mL), and hydrocinnamaldehyde (0.134 g, 1.00 mmol), NaBH$_3$CN (0.10 g, 1.5 mmol) were added to the resulting solution. The mixture was stirred at room temperature for 16 h, and then concentrated under reduced pressure. The residue was treated with saturated HCl in methanol for 30 min, and then concentrated to dryness. The residue was then neutralized with excess DIPEA and methylamine HCl salt in isopropanol, and heated at reflux for 16 h. After concentration the residue was purified on silica gel by flash column chromatography (EtOAc; then MeOH/DCM, 1:6) to afford 2-((2R,3S,4R,5R)-3,4-dihydroxy-5-(hydroxymethyl)-1-(3-phenylpropyl)pyrrolidin-2-yl)-N-methylacetamide as an off-white foam (0071 g, 36%). $^1$H NMR (500 MHz, CD$_3$OD) δ 7.30-7.27 (m, 2H), 7.24-7.22 (m, 2H), 7.20-7.17 (m, 1H), 4.23-4.19 (m, 2H), 4.00-3.98 (m, 1H), 3.88-3.80 (m, 2H), 3.53-3.51 (m, 1H), 3.29-3.28 (m, 1H), 3.22-3.18 (m, 1H), 2.89-2.84 (m, 1H), 2.76-2.67 (m, 6H), 2.11-2.09 (m, 1H), 2.02-1.97 (m, 1H); $^{13}$C NMR (125 MHz, CD$_3$OD) δ 172.48, 141.95, 129.74, 129.57, 127.47, 73.07, 72.45, 72.25, 66.31, 59.70, 52.60, 33.87, 31.86, 28.88, 26.58. MS, (ES, m/z) [M+H]$^+$ 323.2.

The following examples are synthesized according to procedures analogous to the schemes and examples outlined herein.

TABLE 3

| Example | Name | Structure |
|---|---|---|
| 14 | 2-((2R,3R,4R,5R)-1-(3-([1,1'-biphenyl]-4-yl)propyl)-3,4-dihydroxy-5-(hydroxymethyl)pyrrolidin-2-yl)-N-ethylacetamide | 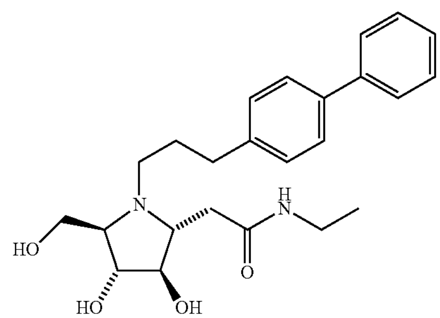 [SMILES: CCNC(=O)C[C@@H]1[C@@H](O)[C@H](O)[C@@H](CO)N1CCCc1ccc(-c2ccccc2)cc1] |
| 15 | 2-((2R,3R,4R,5R)-3,4-dihydroxy-5-(hydroxymethyl)-1-(3-(4'-sulfamoyl-[1,1'-biphenyl]-4-yl)propyl)pyrrolidin-2-yl)-N-methylacetamide | 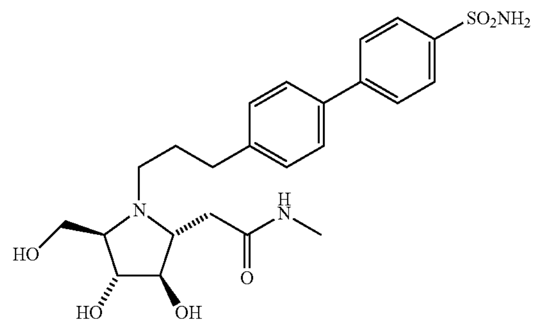 [SMILES: CNC(=O)C[C@@H]1[C@@H](O)[C@H](O)[C@@H](CO)N1CCCc1ccc(-c2ccc(S(N)(=O)=O)cc2)cc1] |
| 16 | 2-((2R,3R,4R,5R)-3,4-dihydroxy-5-(hydroxymethyl)-1-phenethylpyrrolidin-2-yl)-N-ethylacetamide | 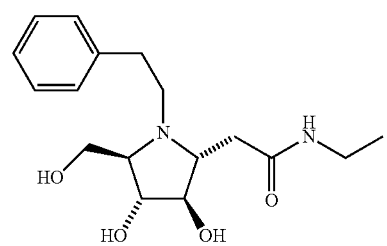 [SMILES: CCNC(=O)C[C@@H]1[C@@H](O)[C@H](O)[C@@H](CO)N1CCc1ccccc1] |
| 17 | (2S,3R,4R,5R)-3,4-dihydroxy-5-(hydroxymethyl)-1-phenethyl-N-propylpyrrolidine-2-carboxamide | 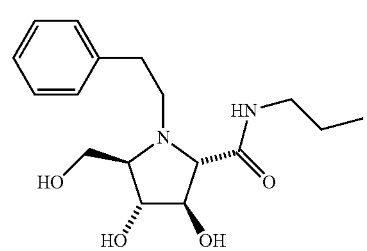 [SMILES: CCCNC(=O)[C@@H]1[C@@H](O)[C@H](O)[C@@H](CO)N1CCc1ccccc1] |

TABLE 3-continued

| Example | Name | Structure |
|---|---|---|
| 18 | N-(((2R,3R,4R,5R)-3,4-dihydroxy-5-(hydroxymethyl)-1-phenethylpyrrolidin-2-yl)methyl)propionamide | 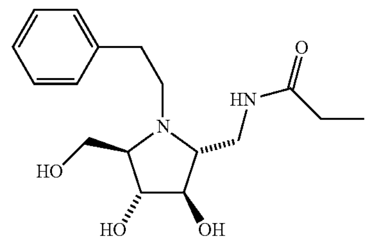 [SMILES: CCC(=O)NC[C@@H]1[C@@H](O)[C@H](O)[C@@H](CO)N1CCc1ccccc1] |
| 19 | N-ethyl-2-((2R,3R,4R,5S)-5-(fluoromethyl)-3,4-dihydroxy-1-phenethylpyrrolidin-2-yl)acetamide | 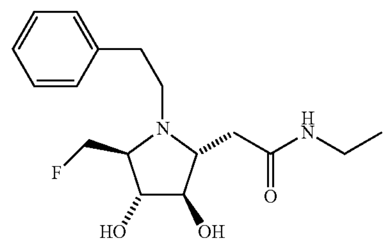 [SMILES: CCNC(=O)C[C@@H]1[C@@H](O)[C@H](O)[C@@H](CF)N1CCc1ccccc1] |
| 20 | N-ethyl-2-((2R,3R,4R,5R)-3-fluoro-4-hydroxy-5-(hydroxymethyl)-1-phenethylpyrrolidin-2-yl)acetamide | 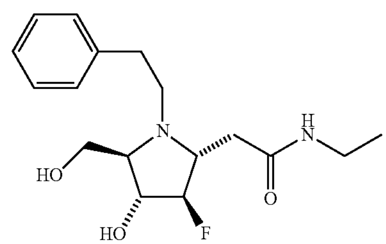 [SMILES: CCNC(=O)C[C@@H]1[C@@H](F)[C@H](O)[C@@H](CO)N1CCc1ccccc1] |
| 21 | N-ethyl-2-((2R,3S,4R,5R)-3-fluoro-4-hydroxy-5-(hydroxymethyl)-1-phenethylpyrrolidin-2-yl)acetamide | 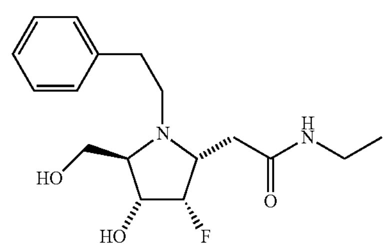 [SMILES: CCNC(=O)C[C@@H]1[C@H](F)[C@H](O)[C@@H](CO)N1CCc1ccccc1] |
| 22 | 2-((2R,3R,4R,5S)-5-(difluoromethyl)-3,4-dihydroxy-1-phenethylpyrrolidin-2-yl)-N-ethylacetamide | 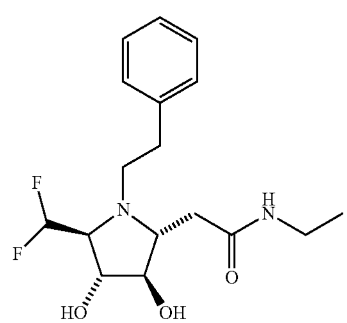 [SMILES: CCNC(=O)C[C@@H]1[C@@H](O)[C@H](O)[C@@H](C(F)F)N1CCc1ccccc1] |
| 23 | 2-((2R,3R,4R,5R)-3-fluoro-4-hydroxy-5-(hydroxymethyl)-1-(3-phenylpropyl)pyrrolidin-2-yl)-N-methylacetamide | 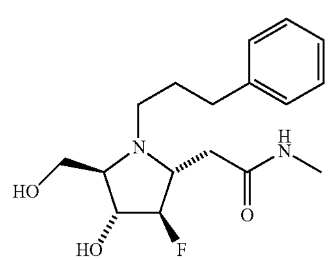 [SMILES: CNC(=O)C[C@@H]1[C@@H](F)[C@H](O)[C@@H](CO)N1CCCc1ccccc1] |

TABLE 3-continued

| Example | Name | Structure |
|---|---|---|
| 24 | 2-((2R,3R,4R,5R)-4-fluoro-3-hydroxy-5-(hydroxymethyl)-1-(3-phenylpropyl)pyrrolidin-2-yl)-N-methylacetamide | 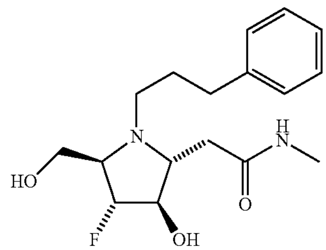 [SMILES: CNC(=O)C[C@@H]1[C@@H](O)[C@H](F)[C@@H](CO)N1CCCc1ccccc1] |
| 25 | 2-((2R,3S,4R,5R)-3-fluoro-4-hydroxy-5-(hydroxymethyl)-1-(3-phenylpropyl)pyrrolidin-2-yl)-N-methylacetamide | 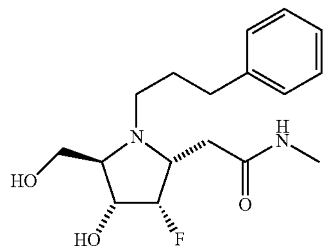 [SMILES: CNC(=O)C[C@@H]1[C@H](F)[C@H](O)[C@@H](CO)N1CCCc1ccccc1] |
| 26 | 2-((2R,3R,4S,5R)-4-fluoro-3-hydroxy-5-(hydroxymethyl)-1-(3-phenylpropyl)pyrrolidin-2-yl)-N-methylacetamide | 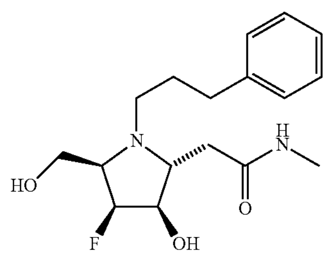 [SMILES: CNC(=O)C[C@@H]1[C@@H](O)[C@@H](F)[C@@H](CO)N1CCCc1ccccc1] |
| 27 | 2-((2R,3R,4R,5S)-5-(fluoromethyl)-3,4-dihydroxy-1-(3-phenylpropyl)pyrrolidin-2-yl)-N-methylacetamide | 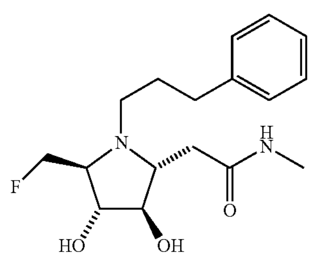 [SMILES: CNC(=O)C[C@@H]1[C@@H](O)[C@H](O)[C@@H](CF)N1CCCc1ccccc1] |
| 28 | 2-((2R,3R,4R,5S)-5-(difluoromethyl)-3,4-dihydroxy-1-(3-phenylpropyl)pyrrolidin-2-yl)-N-methylacetamide | 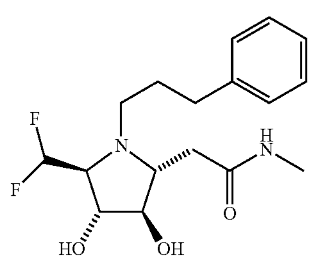 [SMILES: CNC(=O)C[C@@H]1[C@@H](O)[C@H](O)[C@@H](C(F)F)N1CCCc1ccccc1] |
| 29 | 2-((2R,3R,4R,5R)-3,4-dihydroxy-5-methyl-1-(3-phenylpropyl)pyrrolidin-2-yl)-N-methylacetamide | 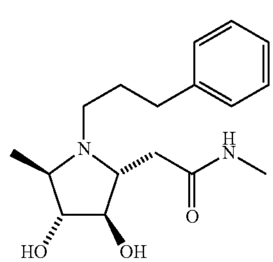 [SMILES: CNC(=O)C[C@@H]1[C@@H](O)[C@H](O)[C@@H](C)N1CCCc1ccccc1] |

TABLE 3-continued

| Example | Name | Structure |
|---|---|---|
| 30 | 2-((2S,4S,5R)-4-hydroxy-5-(hydroxymethyl)-1-(3-phenylpropyl)pyrrolidin-2-yl)-N-methylacetamide | 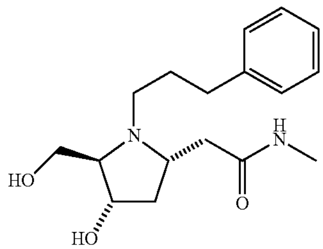 [SMILES: CNC(=O)C[C@@H]1C[C@H](O)[C@@H](CO)N1CCCc1ccccc1] |
| 31 | 2-((2R,3S,5S)-3-hydroxy-5-(hydroxymethyl)-1-(3-phenylpropyl)pyrrolidin-2-yl)-N-methylacetamide | 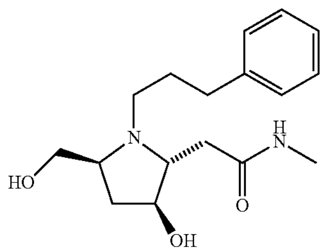 [SMILES: CNC(=O)C[C@@H]1[C@@H](O)C[C@@H](CO)N1CCCc1ccccc1] |
| 32 | 2-((2R,3R,4R)-3,4-dihydroxy-1-(3-phenylpropyl)pyrrolidin-2-yl)-N-methylacetamide | 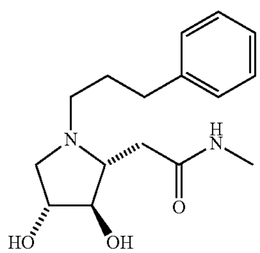 [SMILES: CNC(=O)C[C@@H]1[C@@H](O)[C@H](O)CN1CCCc1ccccc1] |
| 33 | 2-((2R,3R,4R,5S)-3-fluoro-5-(fluoromethyl)-4-hydroxy-1-(3-phenylpropyl)pyrrolidin-2-yl)-N-methylacetamide | 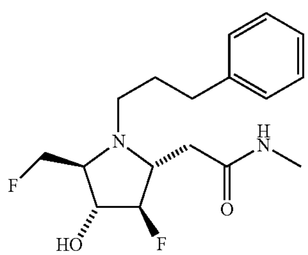 [SMILES: CNC(=O)C[C@@H]1[C@@H](F)[C@H](O)[C@@H](CF)N1CCCc1ccccc1] |
| 34 | 2-((2R,3S,4R,5S)-5-(difluoromethyl)-3-fluoro-4-hydroxy-1-(3-phenylpropyl)pyrrolidin-2-yl)-N-methylacetamide | 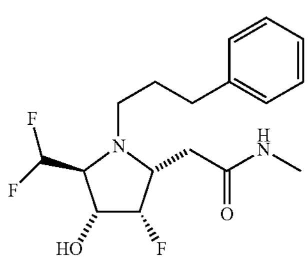 [SMILES: CNC(=O)C[C@@H]1[C@H](F)[C@H](O)[C@@H](C(F)F)N1CCCc1ccccc1] |
| 35 | N-(((2R,3R,4R,5R)-3-fluoro-4-hydroxy-5-(hydroxymethyl)-1-(3-phenylpropyl)pyrrolidin-2-yl)methyl)propionamide | 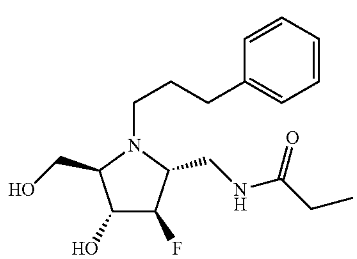 [SMILES: CCC(=O)NC[C@@H]1[C@@H](F)[C@H](O)[C@@H](CO)N1CCCc1ccccc1] |

TABLE 3-continued

| Example | Name | Structure |
|---|---|---|
| 36 | N-(((2R,3R,4R,5R)-4-fluoro-3-hydroxy-5-(hydroxymethyl)-1-(3-phenylpropyl)pyrrolidin-2-yl)methyl)propionamide | 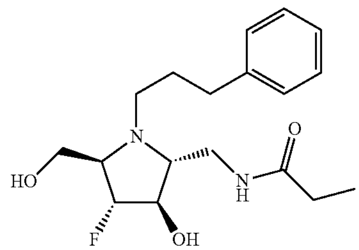 [SMILES: CCC(=O)NC[C@@H]1[C@@H](O)[C@H](F)[C@@H](CO)N1CCCc1ccccc1] |
| 37 | N-(((2R,3S,4R,5R)-3-fluoro-4-hydroxy-5-(hydroxymethyl)-1-(3-phenylpropyl)pyrrolidin-2-yl)methyl)propionamide | 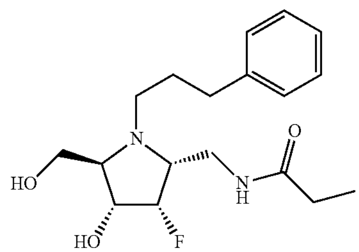 [SMILES: CCC(=O)NC[C@@H]1[C@H](F)[C@H](O)[C@@H](CO)N1CCCc1ccccc1] |
| 38 | N-(((2R,3R,4S,5R)-4-fluoro-3-hydroxy-5-(hydroxymethyl)-1-(3-phenylpropyl)pyrrolidin-2-yl)methyl)propionamide | 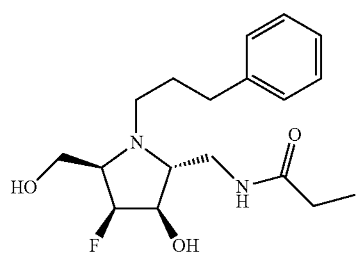 [SMILES: CCC(=O)NC[C@@H]1[C@@H](O)[C@@H](F)[C@@H](CO)N1CCCc1ccccc1] |
| 39 | N-(((2R,3R,4R,5S)-5-(fluoromethyl)-3,4-dihydroxy-1-(3-phenylpropyl)pyrrolidin-2-yl)methyl)propionamide | 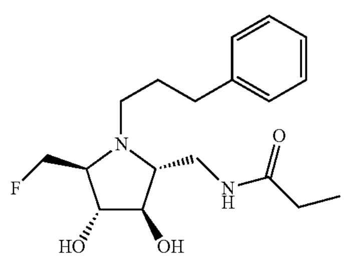 [SMILES: CCC(=O)NC[C@@H]1[C@@H](O)[C@H](O)[C@@H](CF)N1CCCc1ccccc1] |
| 40 | N-(((2R,3R,4R,5S)-5-(difluoromethyl)-3,4-dihydroxy-1-(3-phenylpropyl)pyrrolidin-2-yl)methyl)propionamide | 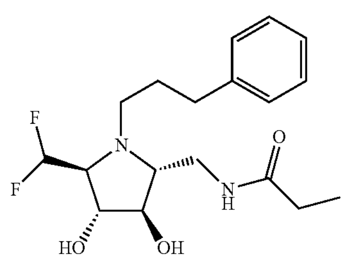 [SMILES: CCC(=O)NC[C@@H]1[C@@H](O)[C@H](O)[C@@H](C(F)F)N1CCCc1ccccc1] |
| 41 | N-(((2S,4S,5R)-4-hydroxy-5-(hydroxymethyl)-1-(3-phenylpropyl)pyrrolidin-2-yl)methyl)propionamide | 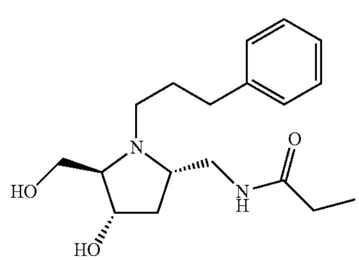 [SMILES: CCC(=O)NC[C@@H]1C[C@H](O)[C@@H](CO)N1CCCc1ccccc1] |

TABLE 3-continued

| Example | Name | Structure |
|---|---|---|
| 42 | N-(((2R,3S,5S)-3-hydroxy-5-(hydroxymethyl)-1-(3-phenylpropyl)pyrrolidin-2-yl)methyl)propionamide | 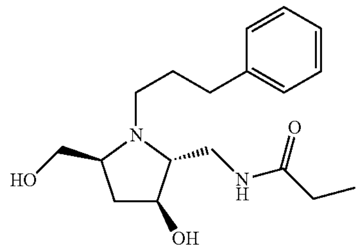 [SMILES: CCC(=O)NC[C@@H]1[C@@H](O)C[C@@H](CO)N1CCCc1ccccc1] |
| 43 | N-(((2R,3R,4R,5R)-3,4-dihydroxy-5-methyl-1-(3-phenylpropyl)pyrrolidin-2-yl)methyl)propionamide | 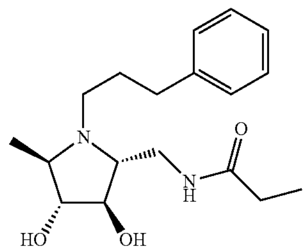 [SMILES: CCC(=O)NC[C@@H]1[C@@H](O)[C@H](O)[C@@H](C)N1CCCc1ccccc1] |
| 44 | N-(((2R,3R,4R)-3,4-dihydroxy-1-(3-phenylpropyl)pyrrolidin-2-yl)methyl)propionamide | 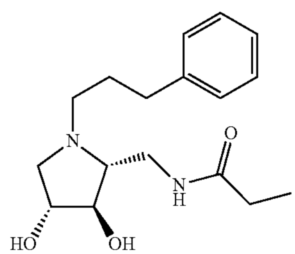 [SMILES: CCC(=O)NC[C@@H]1[C@@H](O)[C@H](O)CN1CCCc1ccccc1] |
| 45 | N-(((2R,3R,4R,5S)-3-fluoro-5-(fluoromethyl)-4-hydroxy-1-(3-phenylpropyl)pyrrolidin-2-yl)methyl)propionamide | 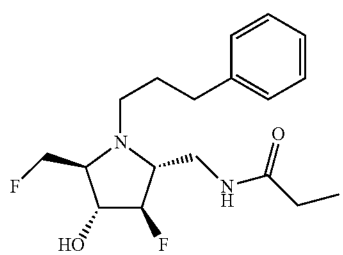 [SMILES: CCC(=O)NC[C@@H]1[C@@H](F)[C@H](O)[C@@H](CF)N1CCCc1ccccc1] |
| 46 | N-(((2R,3S,4R,5S)-5-(difluoromethyl)-3-fluoro-4-hydroxy-1-(3-phenylpropyl)pyrrolidin-2-yl)methyl)propionamide | 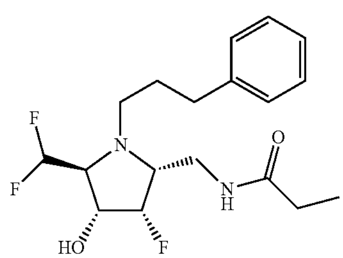 [SMILES: CCC(=O)NC[C@@H]1[C@H](F)[C@H](O)[C@@H](C(F)F)N1CCCc1ccccc1] |
| 47 | N-(((2R,3R,4R,5R)-3,4-dihydroxy-5-(hydroxymethyl)-1-(3-phenylpropanoyl)pyrrolidin-2-yl)methyl)propionamide | 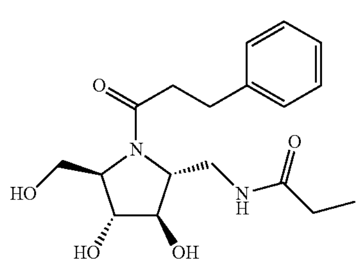 [SMILES: CCC(=O)NC[C@@H]1[C@@H](O)[C@H](O)[C@@H](CO)N1C(=O)CCc1ccccc1] |

TABLE 3-continued

| Example | Name | Structure |
|---|---|---|
| 48 | N-(((2R,3R,4R,5R)-1-(3-(6-fluoropyridin-3-yl)propyl)-3,4-dihydroxy-5-(hydroxymethyl)pyrrolidin-2-yl)methyl)propionamide | 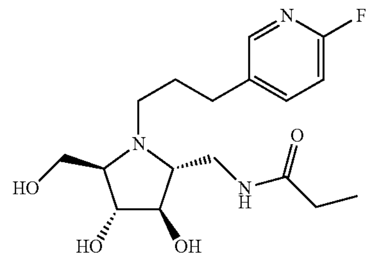 [SMILES: CCC(=O)NC[C@@H]1[C@@H](O)[C@H](O)[C@@H](CO)N1CCCc1ccc(F)nc1] |
| 49 | N-(((2R,3R,4R,5R)-3,4-dihydroxy-5-(hydroxymethyl)-1-(4,4,4-trifluorobutyl)pyrrolidin-2-yl)methyl)propionamide | 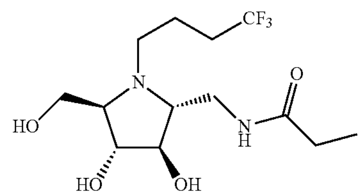 [SMILES: CCC(=O)NC[C@@H]1[C@@H](O)[C@H](O)[C@@H](CO)N1CCCC(F)(F)F] |
| 50 | N-(((2R,3R,4R,5R)-3,4-dihydroxy-5-(hydroxymethyl)-1-(3-(5-(trifluoromethoxy)benzo[d]thiazol-2-yl)propyl)pyrrolidin-2-yl)methyl)propionamide | 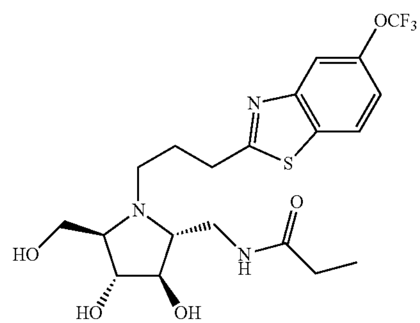 [SMILES: CCC(=O)NC[C@@H]1[C@@H](O)[C@H](O)[C@@H](CO)N1CCCc1nc2cc(OC(F)(F)F)ccc2s1] |
| 51 | 2-((2R,3R,4R,5R)-3,4-dihydroxy-5-(hydroxymethyl)-1-((Z)-5,5,5-trifluoropent-3-en-1-yl)pyrrolidin-2-yl)-N-methylacetamide | 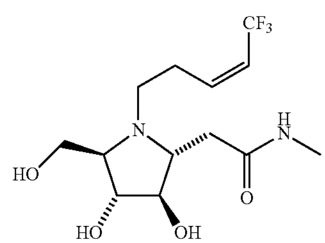 |
| 52 | 2-((2R,3R,4R,5R)-3,4-dihydroxy-5-(hydroxymethyl)-1-(pent-4-yn-1-yl)pyrrolidin-2-yl)-N-methylacetamide | 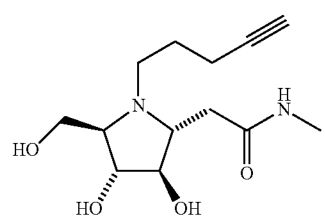 |
| 53 | 2-((2R,3R,4R,5R)-1-butyryl-3,4-dihydroxy-5-(hydroxymethyl)pyrrolidin-2-yl)-N-methylacetamide | 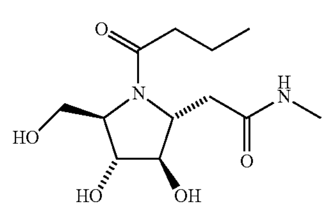 |

TABLE 3-continued

| Example | Name | Structure |
|---------|------|-----------|
| 54 | 2-((2R,3R,4R,5R)-1-(3-(6-fluoropyridin-3-yl)propanoyl)-3,4-dihydroxy-5-(hydroxymethyl)pyrrolidin-2-yl)-N-methylacetamide | 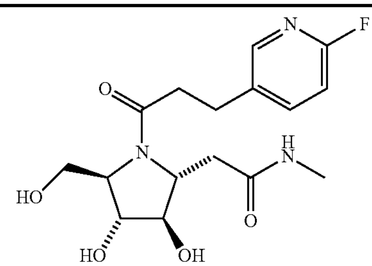 |
| 55 | 2-((2R,3R,4R,5R)-1-cinnamyl-3,4-dihydroxy-5-(hydroxymethyl)pyrrolidin-2-yl)-N-methylacetamide | 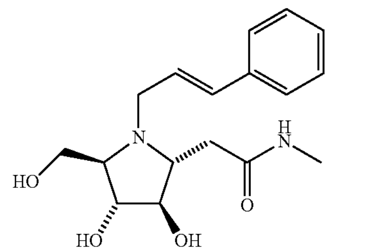 |
| 56 | 2-((2R,3R,4R,5R)-3,4-dihydroxy-5-(hydroxymethyl)-1-(3-phenylprop-2-yn-1-yl)pyrrolidin-2-yl)-N-methylacetamide | 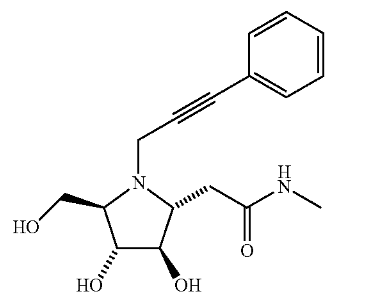 |
| 57 | 2-((2R,3R,4R,5R)-1-((E)-3-(6-fluoropyridin-3-yl)allyl)-3,4-dihydroxy-5-(hydroxymethyl)pyrrolidin-2-yl)-N-methylacetamide | 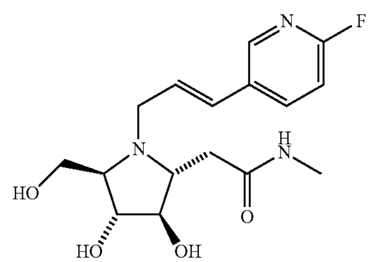 |
| 58 | 2-((2R,3R,4R,5R)-1-(3-(6-fluoropyridin-3-yl)prop-2-yn-1-yl)-3,4-dihydroxy-5-(hydroxymethyl)pyrrolidin-2-yl)-N-methylacetamide | 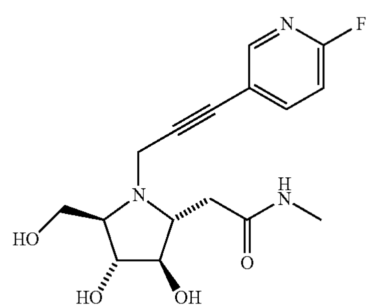 |

Biological Activity

Assay for Determination of $K_I$ Values for Inhibition of O-GlcNAcase Activity

Experimental Procedure for Kinetic Analyses:

Enzymatic reactions were carried out in a reaction containing 50 mM NaH$_2$PO$_4$, 100 mM NaCl and 0.1% BSA (pH 7.0) using 2 mM 4-Methylumbelliferyl N-acetyl-β-D-glucosaminide dihydrate (Sigma M2133) dissolved in ddH$_2$O, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_I$ values were determined using the Cheng-Prusoff equation; the $K_m$ of O-GlcNAcase for substrate was 0.2 mM.

Many compounds of the invention exhibit $K_I$ values for inhibition of O-GlcNAcase in the range 0.1 nM-50 μM.

Assay for Determination of $K_I$ Values for Inhibition of β-Hexosaminidase Activity Experimental Procedure for Kinetic Analyses:

Enzymatic reactions were carried out in a reaction containing 50 mM $NaH_2PO_4$, 100 mM NaCl and 0.1% BSA (pH 7.0) using 2 mM 4-Methylumbelliferyl N-acetyl-β-D-glucosaminide dihydrate (Sigma M2133) dissolved in $ddH_2O$, as a substrate. The amount of purified human β-hexosaminidase enzyme used in the reaction was 24 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_I$ values were determined using the Cheng-Prusoff equation.

When tested in this assay, many of the compounds described herein exhibit $K_I$ values for inhibition of β-hexosaminidase in the range 10 nM to greater than 100 uM.

The selectivity ratio for inhibition of O-GlcNAcase over β-hexosaminidase is defined here as:

$$K_I(\beta\text{-hexosaminidase})/K_I(\text{O-GlcNAcase})$$

In general, many of the compounds described herein exhibit a selectivity ratio in the range of about 10 to 100000. Thus, many compounds of the invention exhibit high selectivity for inhibition of O-GlcNAcase over β-hexosaminidase.

Assay for Determination of Cellular Activity for Compounds that Inhibit O-GlcNAcase Activity Inhibition of O-GlcNAcase, which removes O-GlcNAc from cellular proteins, results in an increase in the level of O-GlcNAcylated protein in cells. An increase in O-GlcNAcylated protein can be measured by an antibody, such as RL-2, that binds to O-GlcNAcylated protein. The amount of O-GlcNAcylated protein:RL2 antibody interaction can be measured by enzyme linked immunosorbant assay (ELISA) procedures.

A variety of tissue culture cell lines, expressing endogenous levels of O-GlcNAcase, can be utilized; examples include rat PC-12, and human U-87, or SK—N—SH cells. In this assay, rat PC-12 cells are plated in 96-well plates with approximately 10,000 cells/well. Compounds to be tested are dissolved in DMSO, either 2 or 10 mM stock solution, and then diluted with DMSO and water in a two-step process using a Tecan workstation. Cells are treated with diluted compounds for 24 h (5.4 μL into 200 μL 1 well volume) to reach a final concentration of inhibitor desired to measure a compound concentration dependent response, typically, ten 3 fold dilution steps, starting at 10 μM are used to determine a concentration response curve. To prepare a cell lysate, the media from compound treated cells is removed, the cells are washed once with phosphate buffered saline (PBS) and then lysed for 5 minutes at room temperature in 50 μL of Phosphosafe reagent (Novagen Inc, Madison, Wis.) with protease inhibitors and PMSF. The cell lysate is collected and transferred to a new plate, which is then either coated to assay plates directly or frozen −80° C. until used in the ELISA procedure. If desired, the total protein concentration of samples is determined using 20 μL of the sample using the BCA method.

The ELISA portion of the assay is performed in a black Maxisorp 96-well plate that is coated overnight at 4° C. with 100 μL/well of the cell lysate (1:10 dilution of the lysate with PBS containing protease inhibitors, phosphatase inhibitors, and PMSF). The following day the wells are washed 3 times with 300 μL/well of Wash buffer (Tris-buffered saline with 0.1% Tween 20). The wells are blocked with 100 μL/well Blocking buffer (Tris buffered saline w/0.05% Tween 20 and 2.5% Bovine serum albumin). Each well is then washed two times with 300 μL/well of wash buffer. The anti O-GlcNAc antibody RL-2 (Abcam, Cambridge, Mass.), diluted 1:1000 in blocking buffer, is added at 100 μL/well. The plate is sealed and incubated at 37° C. for 2 h with gentle shaking. The wells are then washed 3-times with 300 μL/well wash buffer. To detect the amount of RL-2 bound horse-radish peroxidase (HRP) conjugated goat anti-mouse secondary antibody (diluted 1:3000 in blocking buffer) is added at 100 μL/well. The plate is incubated for 60 min at 37° C. with gentle shaking. Each well is then washed 3-times with 300 μL/well wash buffer. The detection reagent is added, 100 μL/well of Amplex Ultra RED reagent (prepared by adding 30 μL of 10 mM Amplex Ultra Red stock solution to 10 mL PBS with 18 μL 3% hydrogen peroxide, $H_2O_2$). The detection reaction is incubated for 15 minutes at room temperature and then read with excitation at 530 nm and emission at 590 nm.

The amount of O-GlcNAcylated protein, as detected by the ELISA assay, is plotted for each concentration of test compound using standard curve fitting algorithms for sigmoidal dose response curves. The values for a four parameter logistic curve fit of the data are determined, with the inflection point of the curve being the potency value for the test compound.

Assay for Determination of Apparent Permeability ($P_{app}$)

Bi-directional transport is evaluated in LLC-PK1 cells in order to determine apparent permeability ($P_{app}$). LLC-PK1 cells can form a tight monolayer and therefore can be used to assess vectorial transport of compounds from basolateral to apical (B→A) and from apical to basolateral (A→B).

To determine $P_{app}$, LLC-PK1 cells are cultured in 96-well transwell culture plates (Millipore). Solutions containing the test compounds (1 μM) are prepared in Hank's Balanced Salt Solution with 10 mM HEPES. Substrate solution (150 μL) is added to either the apical (A) or the basolateral (B)

compartment of the culture plate, and buffer (150 μL) is added to the compartment opposite to that containing the compound. At t=3 h, 50 μL samples are removed from both sides of monolayers dosed with test compound and placed in 96 well plates, scintillant (200 μL) or internal standard (100 μL labetolol 1 μM) is added to the samples and concentration is determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 μM) is used as the positive control. The experiment is performed in triplicate.

The apparent permeability, $P_{app}$, is calculated by the following formula for samples taken at t=3 h:

$$P_{app} = \frac{\text{Volume of Receptor Chamber (mL)}}{[\text{Area of membrane (cm}^2\text{)}][\text{Initial Concentration (}\mu\text{M)}]} \times \frac{\Delta \text{ in Concentration (}\mu\text{M)}}{\Delta \text{ in Time (s)}}$$

Where: Volume of Receptor Chamber is 0.15 mL; Area of membrane is 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). $P_{app}$ is expressed as $10^{-6}$ cm/s. The $P_{app}$ (LLC-PK1 cells) are the average of the $P_{app}$ for transport from A to B and $P_{app}$ for transport from B to A at t=3 h:

$$P_{app}(LLC-PK1\,Cells) = \frac{P_{app}(A \to B) + P_{app}(B \to A)}{2}$$

Representative data from the binding, cell-based, and permeability assays described above are shown in the following table. Certain compounds of the invention exhibit superior potency or permeability in one or more of these assays.

TABLE 4

| Example | Structure | Cell-based ELISA EC$_{50}$ (nM) | Fluorescence-based hOGA Ki (nM) | Papp LLC-PK1 cells (10$^{-6}$ cm/s) |
|---|---|---|---|---|
| — | (structure) | ND | 108 | ND |
| — | (structure) | ND | 2020 | ND |
| — | (structure) | ND | 1030 | ND |
| — | (structure) | ND | 619 | <1.6 |

TABLE 4-continued

| Example | Structure | Cell-based ELISA EC$_{50}$ (nM) | Fluorescence-based hOGA Ki (nM) | Papp LLC-PK1 cells (10$^{-6}$ cm/s) |
|---|---|---|---|---|
| — | (phenethyl pyrrolidine acetamide) | ND | 343 | ND |
| 1 | (3-phenylpropyl pyrrolidine acetamide) | ND | 369 | ND |
| 2 | (3-(4-methoxyphenyl)propyl pyrrolidine acetamide) | ND | 106 | 2.6 |
| 3 | (3-(biphenyl-4-yl)propyl pyrrolidine acetamide) | 665 | 16 | 5.0 |
| 4 | (2-(biphenyl-4-yl)ethyl pyrrolidine acetamide) | ND | 79 | 4.4 |

TABLE 4-continued

| Example | Structure | Cell-based ELISA EC$_{50}$ (nM) | Fluorescence-based hOGA Ki (nM) | Papp LLC-PK1 cells ($10^{-6}$ cm/s) |
|---|---|---|---|---|
| 5 | 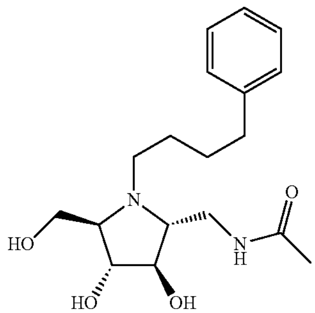 [SMILES: CC(=O)NC[C@@H]1[C@@H](O)[C@H](O)[C@@H](CO)N1CCCCc1ccccc1] | ND | 172 | <1.6 |
| 6 | 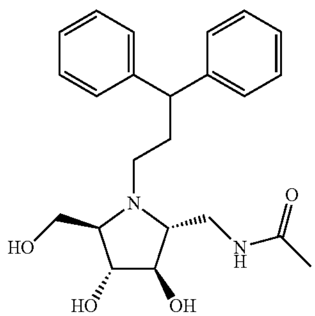 [SMILES: CC(=O)NC[C@@H]1[C@@H](O)[C@H](O)[C@@H](CO)N1CCC(c1ccccc1)c1ccccc1] | ND | 41 | ND |
| 7 | 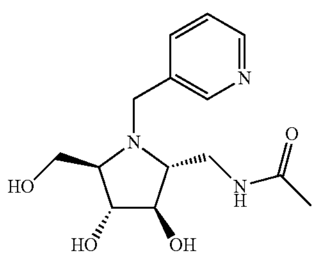 [SMILES: CC(=O)NC[C@@H]1[C@@H](O)[C@H](O)[C@@H](CO)N1Cc1cccnc1] | ND | 2690 | ND |
| 8 | 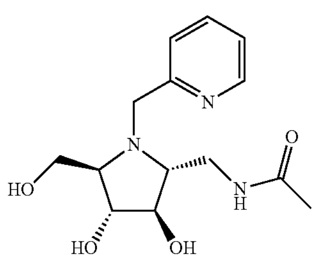 [SMILES: CC(=O)NC[C@@H]1[C@@H](O)[C@H](O)[C@@H](CO)N1Cc1ccccn1] | ND | 3020 | ND |
| 9 | 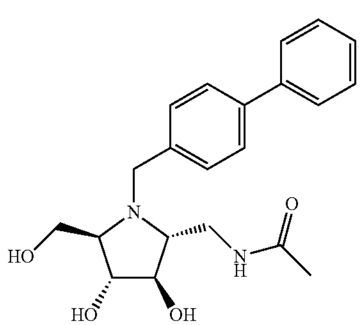 [SMILES: CC(=O)NC[C@@H]1[C@@H](O)[C@H](O)[C@@H](CO)N1Cc1ccc(-c2ccccc2)cc1] | ND | 4560 | ND |

TABLE 4-continued

| Example | Structure | Cell-based ELISA EC$_{50}$ (nM) | Fluorescence-based hOGA Ki (nM) | Papp LLC-PK1 cells (10$^{-6}$ cm/s) |
|---|---|---|---|---|
| 10 | 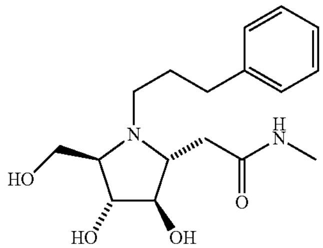 | ND | 55 | ND |
| 11 | 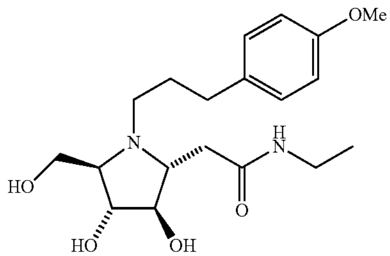 | ND | 132 | ND |
| 12 | 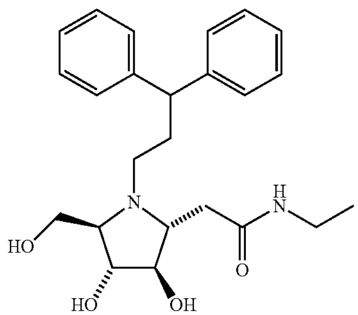 | ND | 60 | ND |
| 13 | 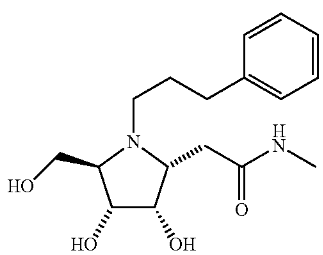 | ND | 8.3 | ND |

The present invention has been described with regard to one or more embodiments. However, it will be apparent to persons skilled in the art that a number of variations and modifications can be made without departing from the scope of the invention as defined in the claims.

REFERENCES

1. C. R. Torres, G. W. Hart, *J Biol Chem* 1984, 259, 3308-17.
2. R. S. Haltiwanger, G. D. Holt, and G. W. Hart, *J Biol Chem* 1990, 265, 2563-8.
3. L. K. Kreppel, M. A. Blomberg, and G. W. Hart, *J Biol Chem* 1997, 272, 9308-15.
4. W. A. Lubas, et al., *J Biol Chem* 1997, 272, 9316-24.
5. W. A. Lubas, J. A. Hanover, *J Biol Chem* 2000, 275, 10983-8.
6. D. L. Dong, G. W. Hart, *J Biol Chem* 1994, 269, 19321-30.
7. Y. Gao, et al., *J Biol Chem* 2001, 276, 9838-45.
8. E. P. Roquemore, et al., *Biochemistry* 1996, 35, 3578-86.
9. S. P. Jackson, R. Tjian, *Cell* 1988, 55, 125-33.
10. W. G. Kelly, M. E. Dahmus, and G. W. Hart, *J Biol Chem* 1993, 268, 10416-24.
11. M. D. Roos, et al., *Mol Cell Biol* 1997, 17, 6472-80.
12. N. Lamarre-Vincent, L. C. Hsieh-Wilson, *J Am Chem Soc* 2003, 125, 6612-3.
13. F. Zhang, et al., *Cell* 2003, 115, 715-25.
14. K. Vosseller, et al., *Proc Natl Acad Sci USA* 2002, 99, 5313-8.
15. W. A. Lubas, et al., *Biochemistry* 1995, 34, 1686-94.
16. L. S. Griffith, B. Schmitz, *Biochem Biophys Res Commun* 1995, 213, 424-31.
17. R. N. Cole, G. W. Hart, *J Neurochem* 1999, 73, 418-28.
18. I. Braidman, et al., *Biochem J* 1974, 143, 295-301.
19. R. Ueno, C. S. Yuan, *Biochim Biophys Acta* 1991, 1074, 79-84.

20. C. Toleman, et al., *J Biol Chem* 2004, 279, 53665-73.
21. F. Liu, et al., *Proc Natl Acad Sci USA* 2004, 101, 10804-9.
22. T. Y. Chou, G. W. Hart, *Adv Exp Med Biol* 2001, 491, 413-8.
23. M. Goedert, et al., *Neuron* 1992, 8, 159-68.
24. M. Goedert, et al., *Neuron* 1989, 3, 519-26.
25. E. Kopke, et al., *J Biol Chem* 1993, 268, 24374-84.
26. H. Ksiezak-Reding, W. K. Liu, and S. H. Yen, *Brain Res* 1992, 597, 209-19.
27. P. V. Arriagada, et al., *Neurology* 1992, 42, 631-9.
28. K. P. Riley, D. A. Snowdon, and W. R. Markesbery, *Ann Neurol* 2002, 51, 567-77.
29. I. Alafuzoff, et al., *Acta Neuropathol* (Berl) 1987, 74, 209-25.
30. C. X. Gong, et al., *J Neural Transm* 2005, 112, 813-38.
31. K. Iqbal, et al., *J Neural Transm Suppl* 2002, 309-19.
32. K. Iqbal, et al., *J Mol Neurosci* 2003, 20, 425-9.
33. W. Noble, et al., *Proc Natl Acad Sci USA* 2005, 102, 6990-5.
34. S. Le Corre, et al., *Proc Natl Acad Sci USA* 2006, 103, 9673-8.
35. S. J. Liu, et al., *J Biol Chem* 2004, 279, 50078-88.
36. G. Li, H. Yin, and J. Kuret, *J Biol Chem* 2004, 279, 15938-45.
37. T. Y. Chou, G. W. Hart, and C. V. Dang, *J Biol Chem* 1995, 270, 18961-5.
38. X. Cheng, G. W. Hart, *J Biol Chem* 2001, 276, 10570-5.
39. X. Cheng, et al., *Biochemistry* 2000, 39, 11609-20.
40. L. S. Griffith, B. Schmitz, *Eur J Biochem* 1999, 262, 824-31.
41. K. Kamemura, G. W. Hart, *Prog Nucleic Acid Res Mol Biol* 2003, 73, 107-36.
42. L. Wells, et al., *J Biol Chem* 2004, 279, 38466-70.
43. L. Bertram, et al., *Science* 2000, 290, 2302-3.
44. S. Hoyer, et al., *Journal of Neural Transmission* 1998, 105, 423-438.
45. C. X. Gong, et al., *Journal of Alzheimers Disease* 2006, 9, 1-12.
46. W. J. Jagust, et al., *Journal of Cerebral Blood Flow and Metabolism* 1991, 11, 323-330.
47. S. Hoyer, *Experimental Gerontology* 2000, 35, 1363-1372.
48. S. Hoyer, in *Frontiers in Clinical Neuroscience: Neurodegeneration and Neuroprotection*, Vol. 541, 2004, 135-152.
49. R. N. Kalaria, S. I. Harik, *Journal of Neurochemistry* 1989, 53, 1083-1088.
50. I. A. Simpson, et al., *Annals of Neurology* 1994, 35, 546-551.
51. S. M. de la Monte, J. R. Wands, *Journal of Alzheimers Disease* 2005, 7, 45-61.
52. X. W. Zhu, G. Perry, and M. A. Smith, *Journal of Alzheimers Disease* 2005, 7, 81-84.
53. J. C. de la Torre, *Neurological Research* 2004, 26, 517-524.
54. S. Marshall, W. T. Garvey, and R. R. Traxinger, *Faseb J* 1991, 5, 3031-6.
55. S. P. Iyer, Y. Akimoto, and G. W. Hart, *J Biol Chem* 2003, 278, 5399-409.
56. K. Brickley, et al., *J Biol Chem* 2005, 280, 14723-32.
57. S. Knapp, C. H. Yang, and T. Haimowitz, *Tetrahedron Letters* 2002, 43, 7101-7104.
58. S. P. Iyer, G. W. Hart, *J Biol Chem* 2003, 278, 24608-16.
59. M. Jinek, et al., *Nat Struct Mol Biol* 2004, 11, 1001-7.
60. K. Kamemura, et al., *J Biol Chem* 2002, 277, 19229-35.
61. Y. Deng, et al., *FASEB J.* 2007, fj.07-8309com.
62. L. F. Lau, et al., *Curr Top Med Chem* 2002, 2, 395-415.
63. M. P. Mazanetz, P. M. Fischer, *Nature Reviews Drug Discovery* 2007, 6, 464-479.
64. S. A. Yuzwa, et al., *Nat Chem Biol* 2008, 4, 483-490.
65. P. Bounelis, et al., *Shock* 2004, 21 170 *Suppl.* 2, 58-58.
66. N. Fulop, et al., *Circulation Research* 2005, 97, E28-E28.
67. J. Liu, R. B. Marchase, and J. C. Chatham, *Faseb Journal* 2006, 20, A317-A317.
68. R. Marchase, et al., *PCT Int. Appl.* WO 2006016904 2006.
69. N. Fulop, et al., *Journal of Molecular and Cellular Cardiology* 2004, 37, 286-287.
70. N. Fulop, et al., *Faseb Journal* 2005, 19, A689-A690.
71. J. Liu, R. B. Marchase, and J. C. Chatham, *Journal of Molecular and Cellular Cardiology* 2007, 42, 177-185.
72. L. G. Not, et al., *Faseb Journal* 2006, 20, A1471-A1471.
73. S. L. Yang, et al., *Shock* 2006, 25, 600-607.
74. L. Y. Zou, et al., *Faseb Journal* 2005, 19, A1224-A1224.
75. R. B. Marchase, et al., *Circulation* 2004, 110, 1099-1099.
76. J. Liu, et al., *Journal of Molecular and Cellular Cardiology* 2006, 40, 303-312.
77. J. Liu, J. C. Chatham, and R. B. Marchase, *Faseb Journal* 2005, 19, A691-A691.
78. T. Nagy, et al., *American Journal of Physiology-Cell Physiology* 2006, 290, C57-C65.
79. N. Fulop, R. B. Marchase, and J. C. Chatham, *Cardiovascular Research* 2007, 73, 288-297.
80. T. Lefebvre, et al., *Expert Review of Proteomics* 2005, 2, 265-275.
81. B. Henrissat, A. Bairoch, *Biochem J* 1993, 293 (Pt 3), 781-8.
82. B. Henrissat, A. Bairoch, *Biochem J* 1996, 316 (Pt 2), 695-6.
83. L. Wells, K. Vosseller, and G. W. Hart, *Science* 2001, 291, 2376-8.
84. J. A. Hanover, *FASEB J* 2001, 15, 1865-76.
85. D. A. McClain, et al., *Proc Natl Acad Sci USA* 2002, 99, 10695-9.
86. P. J. Yao, P. D. Coleman, *J Neurosci* 1998, 18, 2399-411.
87. W. H. Yang, et al., *Nature Cell Biology* 2006, 8, 1074-U53.
88. B. Triggs-Raine, D. J. Mahuran, and R. A. Gravel, *Adv Genet* 2001, 44, 199-224.
89. D. Zhou, et al., *Science* 2004, 1786-89.
90. G. Legler, et al., *Biochim Biophys Acta* 1991, 1080, 89-95.
91. M. Horsch, et al., *Eur J Biochem* 1991, 197, 815-8.
92. J. Liu, et al., *Chem Biol* 2001, 8, 701-11.
93. S. Knapp, et al., *J Am. Chem. Soc.* 1996, 118, 6804-6805.
94. V. H. Lillelund, et al., *Chem Rev* 2002, 102, 515-53.
95. R. J. Konrad, et al., *Biochem J* 2001, 356, 31-41.
96. K. Liu, et al., *J Neurochem* 2004, 89, 1044-55.
97. G. Parker, et al., *J Biol Chem* 2004, 279, 20636-42.
98. E. B. Arias, J. Kim, and G. D. Cartee, *Diabetes* 2004, 53, 921-30.
99. A. Junod, et al., *Proc Soc Exp Biol Med* 1967, 126, 201-5.
100. R. A. Bennett, A. E. Pegg, *Cancer Res* 1981, 41, 2786-90.
101. K. D. Kroncke, et al., *Biol Chem Hoppe Seyler* 1995, 376, 179-85.
102. H. Yamamoto, Y. Uchigata, and H. Okamoto, *Nature* 1981, 294, 284-6.
103. K. Yamada, et al., *Diabetes* 1982, 31, 749-53.
104. V. Burkart, et al., *Nat Med* 1999, 5, 314-9.

105. M. D. Roos, et al., *Proc Assoc Am Physicians* 1998, 110, 422-32.
106. Y. Gao, G. J. Parker, and G. W. Hart, *Arch Biochem Biophys* 2000, 383, 296-302.
107. R. Okuyama, M. Yachi, *Biochem Biophys Res Commun* 2001, 287, 366-71.
108. N. E. Zachara, et al., *J Biol Chem* 2004, 279, 30133-42.
109. J. A. Hanover, et al., *Arch Biochem Biophys* 1999, 362, 38-45.
110. K. Liu, et al., *Mol Cell Endocrinol* 2002, 194, 135-46.
111. M. S. Macauley, et al., *J Biol Chem* 2005, 280, 25313-22.
112. B. L. Mark, et al., *J Biol Chem* 2001, 276, 10330-7.
113. R. S. Haltiwanger, K. Grove, and G. A. Philipsberg, *J Biol Chem* 1998, 273, 3611-7.
114. D. J. Miller, X. Gong, and B. D. Shur, *Development* 1993, 118, 1279-89.
115. L. Y. Zou, et al., *Shock* 2007, 27, 402-408.
116. J. B. Huang, A. J. Clark, and H. R. Petty, *Cellular Immunology* 2007, 245, 1-6.
117. N. E. Zachara, et al., *Abstract* 418 in *Joint Meeting of the Society for Glycobiology and the Japanese Society of Carbohydrate Research*. Honolulu, Hi., 2004.
118. L. Y. Zou, et al., *Faseb Journal* 2006, 20, A1471-A1471.
119. V. Champattanachai, R. B. Marchase, and J. C. Chatham, *American Journal of Physiology-Cell Physiology* 2007, 292, C178-C187.
120. V. Champattanachai, R. B. Marchase, and J. C. Chatham, *American Journal of Physiology-Cell Physiology* 2008, 294, C1509-C1520.
121. I. Khlistunova, et al., *Current Alzheimer Research* 2007, 4, 544-546.
122. P. Friedhoff, et al., *Biochemistry* 1998, 37, 10223-10230.
123. M. Pickhardt, et al., *Journal of Biological Chemistry* 2005, 280, 3628-3635.

What is claimed is:

1. A compound of Formula (I) or a pharmaceutically acceptable salt thereof:

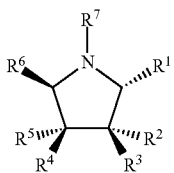

(I)

wherein $R^1$ is selected from the group consisting of: $CH_2NR^8R^9$, wherein $R^8$ is H and $R^9$ is $C_{1-6}$ acyl, and $(CH_2)_nC(O)NR^{10}_2$, wherein n is 1, and one $R^{10}$ is H and the other $R^{10}$ is $C_{1-6}$ alkyl;

$R^2$ is H and $R^3$ is OH, or $R^2$ is H and $R^3$ is H, or $R^2$ is H and $R^3$ is F, or $R^2$ is F and $R^3$ is H, or $R^2$ is F and $R^3$ is F, or $R^2$ is OH and $R^3$ is H;

$R^4$ is H and $R^5$ is OH, or $R^4$ is H and $R^5$ is H, or $R^4$ is H and $R^5$ is F, or $R^4$ is F and $R^5$ is H, or $R^4$ is F and $R^5$ is F, or $R^4$ is OH and $R^5$ is H;

$R^6$ is selected from the group consisting of: $CH_3$, $CH_2F$, and $CHF_2$; and $R^7$ is selected from the group consisting of: $C_{1-18}$ alkyl, $C_{2-10}$ alkenyl, $C_{2-10}$ alkynyl, $C_{7-20}$ arylalkyl, $C_{8-20}$ arylalkenyl, and $C_{8-20}$ arylalkynyl, each optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl, with the proviso that the compound excludes N-(((2R,3R,4R,5R)-3,4-dihydroxy-5-methylpyrrolidin-2-yl)methyl)acetamide.

2. The compound of claim 1 wherein the compound is selected from the following group:

N-ethyl-2-((2R,3R,4R,5S)-5-(fluoromethyl)-3,4-dihydroxy-1-phenethylpyrrolidin-2-yl)acetamide;

2-((2R,3R,4R,5S)-5-(difluoromethyl)-3,4-dihydroxy-1-phenethylpyrrolidin-2-yl)-N-ethylacetamide;

2-((2R,3R,4R,5S)-5-(fluoromethyl)-3,4-dihydroxy-1-(3-phenylpropyl)pyrrolidin-2-yl)-N-methylacetamide;

2-((2R,3R,4R,5S)-5-(difluoromethyl)-3,4-dihydroxy-1-(3-phenylpropyl)pyrrolidin-2-yl)-N-methylacetamide;

2-((2R,3R,4R,5R)-3,4-dihydroxy-5-methyl-1-(3-phenylpropyl)pyrrolidin-2-yl)-N-methylacetamide;

2-((2R,3R,4R,5S)-3-fluoro-5-(fluoromethyl)-4-hydroxy-1-(3-phenylpropyl)pyrrolidin-2-yl)-N-methylacetamide;

2-((2R,3S,4R,5S)-5-(difluoromethyl)-3-fluoro-4-hydroxy-1-(3-phenylpropyl)pyrrolidin-2-yl)-N-methylacetamide;

N-(((2R,3R,4R,5S)-5-(fluoromethyl)-3,4-dihydroxy-1-(3-phenylpropyl)pyrrolidin-2-yl)methyl)propionamide;

N-(((2R,3R,4R,5S)-5-(difluoromethyl)-3,4-dihydroxy-1-(3-phenylpropyl)pyrrolidin-2-yl)methyl)propionamide;

N-(((2R,3R,4R,5R)-3,4-dihydroxy-5-methyl-1-(3-phenylpropyl)pyrrolidin-2-yl)methyl)propionamide;

N-(((2R,3R,4R,5S)-3-fluoro-5-(fluoromethyl)-4-hydroxy-1-(3-phenylpropyl)pyrrolidin-2-yl)methyl)propionamide;

N-(((2R,3S,4R,5S)-5-(difluoromethyl)-3-fluoro-4-hydroxy-1-(3-phenylpropyl)pyrrolidin-2-yl)methyl)propionamide;

or a pharmaceutically acceptable salt of any of the foregoing compounds.

3. A pharmaceutical composition comprising the compound of claim 1 or a pharmaceutically acceptable salt thereof in combination with a pharmaceutically acceptable carrier.

4. A pharmaceutical composition comprising a compound of claim 2 or a pharmaceutically acceptable salt thereof in combination with a pharmaceutically acceptable carrier.

5. The compound of claim 1 wherein the compound is selected from the following group:

N-ethyl-2-((2R,3R,4R,5S)-5-(fluoromethyl)-3,4-dihydroxy-1-phenethylpyrrolidin-2-yl)acetamide;

2-((2R,3R,4R,5S)-5-(difluoromethyl)-3,4-dihydroxy-1-phenethylpyrrolidin-2-yl)-N-ethylacetamide;

2-((2R,3R,4R,5S)-5-(fluoromethyl)-3,4-dihydroxy-1-(3-phenylpropyl)pyrrolidin-2-yl)-N-methylacetamide;

2-((2R,3R,4R,5S)-5-(difluoromethyl)-3,4-dihydroxy-1-(3-phenylpropyl)pyrrolidin-2-yl)-N-methylacetamide;

N-(((2R,3R,4R,5S)-5-(fluoromethyl)-3,4-dihydroxy-1-(3-phenylpropyl)pyrrolidin-2-yl)methyl)propionamide;

N-(((2R,3R,4R,5S)-5-(difluoromethyl)-3,4-dihydroxy-1-(3-phenylpropyl)pyrrolidin-2-yl)methyl)propionamide;

or a pharmaceutically acceptable salt of any of the foregoing compounds.

6. A pharmaceutical composition comprising a compound of claim 5 or a pharmaceutically acceptable salt thereof in combination with a pharmaceutically acceptable carrier.

* * * * *